United States Patent [19]

Altchuler

[11] Patent Number: 5,468,222
[45] Date of Patent: Nov. 21, 1995

[54] PROCESS FOR DETERMINING DRUG TAPER SCHEDULES

[75] Inventor: Steven I. Altchuler, Rochester, Minn.

[73] Assignee: Mayo Foundation for Medical Education & Research, Rochester, Minn.

[21] Appl. No.: 25,890

[22] Filed: Apr. 21, 1993

Related U.S. Application Data

[63] Continuation of Ser. No. 518,519, May 3, 1990, abandoned.

[51] Int. Cl.[6] .................................................. A61M 31/00
[52] U.S. Cl. .................................................. 604/49
[58] Field of Search .................. 364/413.02, 413.01; 604/131, 19, 97, 49; 128/DIG. 13

[56] References Cited

U.S. PATENT DOCUMENTS

| | | | |
|---|---|---|---|
| 4,373,527 | 2/1983 | Fischell | 128/260 |
| 4,624,661 | 11/1986 | Arimond | 604/151 |
| 4,731,051 | 3/1988 | Fischell | 604/67 |
| 4,731,725 | 3/1988 | Suto et al. | 364/413.01 |
| 4,785,799 | 11/1988 | Schoon et al. | 128/53 |
| 4,839,822 | 6/1989 | Dormond et al. | 364/413.02 |
| 4,898,578 | 2/1990 | Rubalcaba, Jr. | 364/188 |
| 5,025,374 | 6/1991 | Roizen et al. | 364/413.02 |
| 5,104,374 | 4/1992 | Bishko et al. | 604/31 |

OTHER PUBLICATIONS

Wilson et al., "Designing a Guideline–Based Utilization Management Program," *Benefits Quarterly*, 1991, pp. 42–47.

Greenes, "Computer–Aided Diagnostic Strategy Selection," *Radiologic Clinics of North America*, vol. 24, No. 1, Mar. 1986, pp. 105–120.

*Primary Examiner*—Robert A. Weinhardt
*Assistant Examiner*—Jennifer L. Hazard
*Attorney, Agent, or Firm*—Hugh D. Jaeger

[57] ABSTRACT

Process for calculating decreasing doses of a drug a patient needs to take to be able to finally stop taking the drug algorithm. The process is based on an exponential drug taper. This is particularly useful for a drug which a patient is either physically or psychologically dependent, and for a drug where there are potentially serious side effects (for example, seizures) if the drug is rapidly discontinued. The program calculates the amount of drug and provides the clinician the opportunity to look at several different possible drug taper schedules, both numerically and graphically, and to aid the clinician in choosing the appropriate drug taper. The process can calculate a drug taper based upon actual clinical response of a patient. The process corrects for actual dosage sizes available, and calculates administration schedules for the patient and nurse.

1 Claim, 24 Drawing Sheets

Drug Taper Schedule April 11,

| Date | Total Dose |
|---|---|
| 10 Apr 90 | 500.000 |
| 11 Apr 90 | 320.000 |
| 12 Apr 90 | 260.000 |
| 13 Apr 90 | 210.000 |
| 14 Apr 90 | 165.000 |
| 15 Apr 90 | 135.000 |
| 16 Apr 90 | 110.000 |
| 17 Apr 90 | 85.000 |
| 18 Apr 90 | 70.000 |
| 19 Apr 90 | 55.000 |
| 20 Apr 90 | 45.000 |
| 21 Apr 90 | 35.000 |
| 22 Apr 90 | 30.000 |
| 23 Apr 90 | 25.000 |
| 24 Apr 90 | 20.000 |
| 25 Apr 90 | 15.000 |
| 26 Apr 90 | 10.000 |
| 27 Apr 90 | 10.000 |
| 28 Apr 90 | 10.000 |
| 29 Apr 90 | 5.000 |
| 30 Apr 90 | 5.000 |

FIG. 6

Drug Taper Schedule    April 11,

|  | 7 am | 12 noon | 5 pm | 10 pm |
|---|---|---|---|---|
| 10 Apr 90 | 125.000 | 125.000 | 125.000 | 125.000 |
| 11 Apr 90 | 80.000 | 80.000 | 80.000 | 80.000 |
| 12 Apr 90 | 65.000 | 65.000 | 65.000 | 65.000 |
| 13 Apr 90 | 55.000 | 50.000 | 50.000 | 55.000 |
| 14 Apr 90 | 40.000 | 40.000 | 40.000 | 45.000 |
| 15 Apr 90 | 35.000 | 30.000 | 35.000 | 35.000 |
| 16 Apr 90 | 30.000 | 25.000 | 25.000 | 30.000 |
| 17 Apr 90 | 20.000 | 20.000 | 20.000 | 25.000 |
| 18 Apr 90 | 20.000 | 15.000 | 15.000 | 20.000 |
| 19 Apr 90 | 15.000 | 10.000 | 15.000 | 15.000 |
| 20 Apr 90 | 10.000 | 10.000 | 10.000 | 15.000 |
| 21 Apr 90 | 10.000 | 5.000 | 10.000 | 10.000 |
| 22 Apr 90 | 10.000 | 5.000 | 5.000 | 10.000 |
| 23 Apr 90 | 5.000 | 5.000 | 5.000 | 10.000 |
| 24 Apr 90 | 5.000 | 5.000 | 5.000 | 5.000 |
| 25 Apr 90 | 5.000 | 0.000 | 5.000 | 5.000 |
| 26 Apr 90 | 5.000 | 0.000 | 0.000 | 5.000 |
| 27 Apr 90 | 5.000 | 0.000 | 0.000 | 5.000 |
| 28 Apr 90 | 5.000 | 0.000 | 0.000 | 5.000 |
| 29 Apr 90 | 0.000 | 0.000 | 0.000 | 5.000 |
| 30 Apr 90 | 0.000 | 0.000 | 0.000 | 5.000 |

FUNCTIONS

___ DRAW ___ SKED ___ INFO ( )

___ DRAW ___ DRUG ___ INFO ( )

___ DRAW ___ TECH ___ INFO ( )

___ DRAW ___ TAPER ___ INFO ( )

THESE 4 FUNCTIONS ALL DISPLAY PART OF THE INFORMATION ABOUT THE TAPER FOR THE PROCESSING SCREEN AND THE INPUT SCREEN

P. M-1

FUNCTION __ GET __ INFO ( )

DATA INPUT FUNCTION

PROCESS FOR DETERMINING DRUG TAPER SCHEDULES

This patent application is a continuation of U.S. Ser. No. 07/518,519, filed May 3, 1990, now abandoned, entitled "Process for Determining Drug Taper Schedules", to the same assignee of thee present invention.

BACKGROUND OF THE INVENTION

1. Field of the Invention

The present invention relates to drug administration, and more particularly, pertains to a process for determining drug taper schedules by an algorithm which can be implemented by a computer.

2. Description of the Prior Art

Use of drug tapers is important in many fields. Experience shows routine use in detoxifying patients admitted for chemical dependency, but it also occurs when withdrawing patients from different drugs which they have used for long periods of time. In addition, when patients have been on drugs where rebound effects may be dangerous, drug tapering is necessary.

Previously, drug tapers have been calculated by hand, and they have been typically a "linear" taper. For example, a "10%" taper from 500 mg would go 500, 450, 400, 350, 300, 250, 200, 150, 100, 50. An exponential taper of this program would be, e.g., 500, 450, 405, 365, 329, 296, 266, 239, etc. The other approach that has been used has been to recalculate the drug taper on an almost daily basis, by the "seat of the pants". In other words, the physician may drop the patient from 500 mg to 450 mg one day, observe him the next, and then based on clinical experience, guess what the next drop should be, then continue this process on a daily basis. If a patient encountered difficulties using the "linear taper", such as showing signs of withdrawal or intoxication, then the "seat-of-the-pants" approach was the only approach that could be used.

The literature in the field generally agrees upon the need for a "gradual" taper, but the specifics of such a drug taper are generally not published. The approach usually taken involves either a slow linear taper where a fixed percentage of the starting dose is taken away over every period of time, a stepwise taper where patients are dropped by a fixed percentage and then held at the next step for a period of time before the next reduction, or a combination taper where the patient has an initial large drop followed by a linear taper.

When drug detoxification has been studied, it has been found that the actual requirements for drugs are not easily determined by biochemical parameters. That is, the amount of drug a patient needs is not necessarily reflected by, for example, serum levels. Rather, it appears that a patient's requirement for drugs during detoxification is a complex determination, effected by many physical, psychological, and social factors.

The traditional linear taper chooses a certain percentage of the initial dose, and then reduces the dose by the same absolute amount over each time interval. This is unsatisfactory, as it leads to ever increasing percentage decrements. This same problem occurs in both the step-wise taper and also over the major portion of the combination taper. In addition, the linear taper is inconsistent.

Consider a patient being detoxified from a total daily dose of 500 mg using a 10% linear taper. This patient will have his dose reduced by 50 mg every twenty-four hours. When this patient reaches a level of 100 mg, he will then be reduced to 50 mg, then none over the next two days. However, if this same patient were being detoxified from a total daily dose of 200 mg using a 10% taper (i.e., a reduction of 20 mg every twenty-four hours), the reduction from 100 mg to none would take two and one-half times as long (FIG. 2).

Clinically, experience has shown that linear tapers have not been appropriate for patients. The Mayo Clinic's experience has shown that linear tapers do not work in the patients whom they see. Rather, one finds that patients do best when they have larger decrements earlier in the drug taper schedule, and smaller decrements later.

The present invention overcomes the disadvantages of the prior art by providing drug tapers to give the patient the minimum amount of drug required at any given time and to prevent the emergence of any type of abstinence syndrome or rebound effect.

SUMMARY OF THE INVENTION

The general purpose of the present invention is for three specific areas of drug tapering. The first is the specific mathematical calculation through an algorithm of a drug detoxification taper by other than a simple linear scheme. In specific, the current approach uses an exponentially-declining drug taper, although as the program advances and develops with further research, more complicated drug tapering formulas can be developed. The second is the use of a computer to present to the clinician several different drug tapers simultaneously, and to allow him to see what the drug tapers would look like to assist the physician in choosing one that would be most appropriate for a given patient. For example, the use of a program allows the physician to see and compare a 95% taper, a 90% taper, an 85% taper, etc. This provides the physician with a direct, head-to-head comparison of the drug tapers before the physician decides which is appropriate for the patient to use. The third is a program which will also automatically calculate drug administration schedules, simplifying use for patients, nurses, pharmacists, and the physician. For example, if a patient has to take 125 mg of a drug per day, that needs to be taken four times a day, the program automatically will calculate how much to take at each time.

According to one embodiment of the present invention, there is provided a process through an algorithm for quantifying a drug taper, allowing a clinician to view alternative drug tapers to facilitate choosing the most appropriate clinical drug taper, and automating the calculation and printing of drug administration schedules for nursing, pharmacy and patient usage.

Significant aspects and features of the present invention include a quantitative approach to drug detoxification in place of the current approach, which is either "seat of the pants" or a simplistic linear taper.

Another significant aspect and feature of the present invention is the opportunity to see several drug tapers simultaneously and in comparison before choosing one to use.

A further significant aspect and feature of the present invention is the calculation of actual drug administration schedules.

An additional significant aspect and feature of the present invention is if a patient has difficulty and either goes into withdrawal or suffers a rebound effect as the patient is not receiving enough medication or becomes intoxicated as the patient is receiving too much, the computerized approach allows recalculation of the drug taper based on the patient's known response. Specifically, the physician knows the starting dose the patient was stable on, and now knows another dose at a different point in time (for example, how much the patient took with additional doses to stabilize the withdrawal signs), and the physician can extrapolate through those two points using the formulas and calculate a new drug taper. This new drug taper would be based on the actual patient's responses.

Still another significant aspect and feature of the present invention is an algorithm which allows for recalculation of a taper based on actual clinical response.

Having thus described the embodiments of the present invention, it is a principal object hereof to provide an algorithm for determining a drug taper schedule.

One object of the present invention is to calculate a drug taper schedule with an algorithm. A computer expedites the algorithm calculations.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 6 illustrates a table of drug taper schedules;

FIG. 7 illustrates a table of drug taper schedules and drug administration schedule; and, FIG. 8A–8Q illustrates a flow chart of a drug tapering algorithm.

DESCRIPTION OF THE PREFERRED EMBODIMENTS

Figure 1:
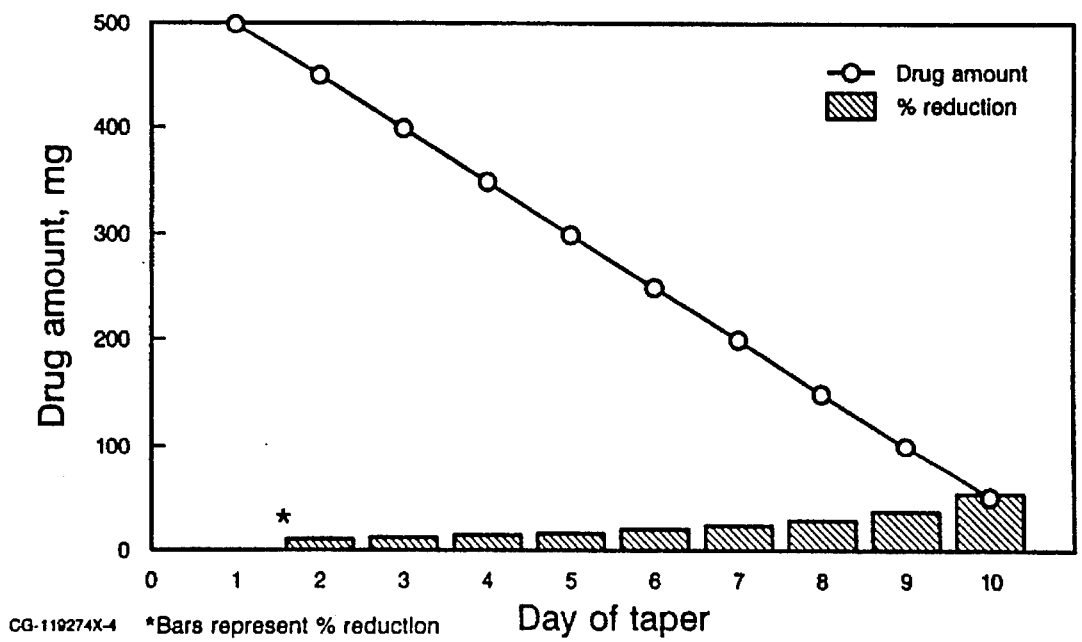
FIG. 1 illustrates prior art drug tapering process.
Figure 2:
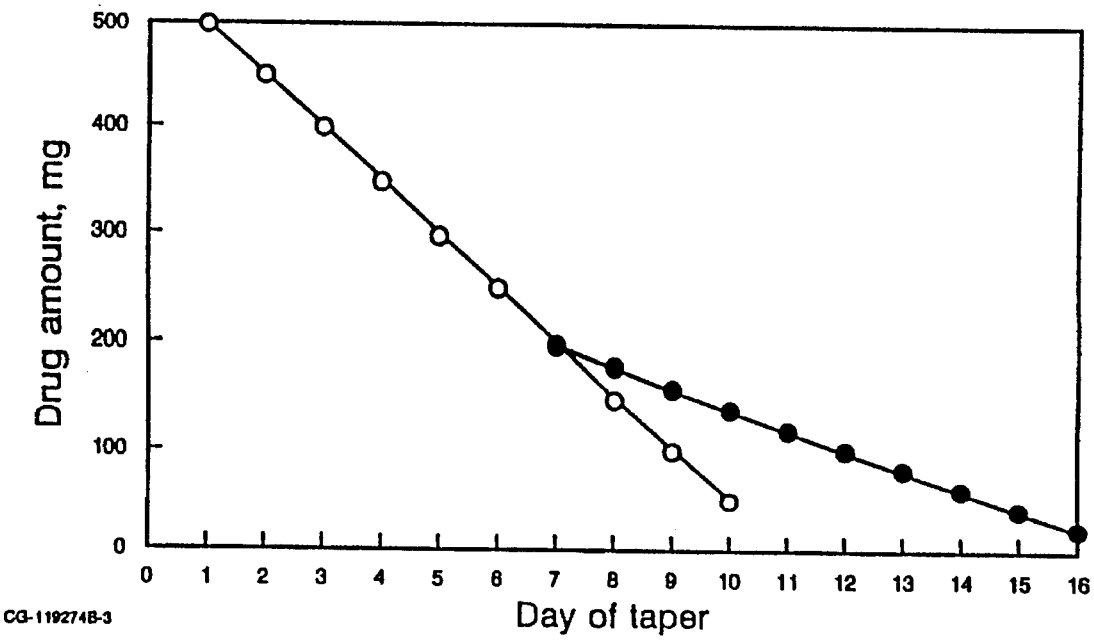
FIG. 2 illustrates prior art drug tapering process.
Figure 3:
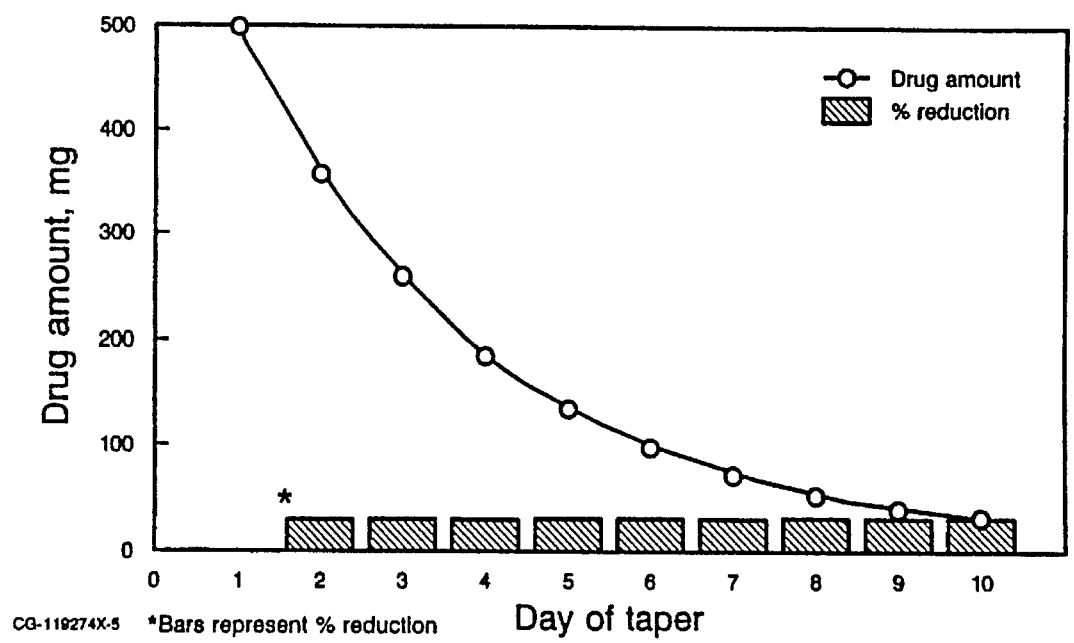
FIG. 3 illustrates a drug tapering decreasing exponential curve.

The preferred drug tapering process does not use a constant value for the drug decrement, but rather keeps the decrement from one time period to another as a constant percentage of the previous dose. The process should be constant in a drug taper as the percentage decrease in dose from one time period to the next. Although this is straightforward to calculate mathematically, it is a time consuming calculation as illustrated in FIG. 3. It is only with the widespread distribution of computers to clinical facilities that this type of process can now be easily implemented. The constant percentage decreases yields on exponential drug taper.

Mathematically, the drug taper algorithm can be defined as follows:

Symbols $k_1$ Initial dose at time 0

$k_2$ Decrement, as a value between 0 and 1

$t$ Time $G(t)$ Amount of drug given at time $t$ $Rnd(a,b)$ Rounding function, which rounds a to the nearest multiple of b $Min(a,b)$ Minimum function, which chooses the minimum of a or b M Minimum Dosage Size Available $y, y', y''$ Intermediate functions, defined below.

Theoretically, the shape of the exponential drug taper is:

$$y''(t) = k_1 k_2^t \qquad \text{(Equation 1)}$$

However, in reality one needs to correct for the fact that drugs cannot be administered in infinitely-dividable quantities, but rather are given in discrete doses. Thus, in practice, one sums up the total theoretical amount which should have been given at this time, and subtract the amount actually given to date:

$$y(t) = \sum_{i=1}^{t} y''(i) - \sum_{i=1}^{t-1} G(i) \qquad \text{(Equation 2)}$$

(Valid only for $t > 1$)

One then sets a condition that one cannot give a higher dose than previously given; that is, the doses are continually decreasing:

$$y'(t) = Min [y(t), G(t-1)] \qquad \text{(Equation 3)}$$

Next, one calculates the amount to be given to the nearest available dose size:

$$G(t) = Rnd(k_1 k_2^t, M) \text{ (for } t=1\text{, or) } Rnd [y'(t), M] \text{ (for } t>1) \qquad \text{(Equation 4)}$$

where M represents the minimum dosage size available. In reality, this function (Equation 4) is not necessarily so simple, as drugs may have sizes that are not multiples of each other, such as 2 and 25 mg, so that the drugs can be multiples of 1 mg.

The basic process of the algorithm used equation 1, in combination with equation 4. If desired, equations 2 and 3 can also be used, although in practice, one finds that equations 2 and 3 really offer little additional advantage. The reason for this is that the rounding errors created by rounding to the nearest dose size actually available overestimates and underestimates the true cover about equally.

Equation 4 is restated as:

$$G(t) = Rnd[y''(t), M] \qquad \text{(Equation 5)}$$

when only using equations 1 and 4; and it remains:

$$G(t) = Rnd[y(t), M] \qquad \text{(Equation 6)}$$

when using equations 1, 2, and 4.

In preferred order of the algorithm implementation, equations are utilized in the following combinations:

1. Equations 1 and 5.
2. Equations 1, 2, and 6.
3. Equations 1, 2, 3, and 4.
4. Equation 1

Figure 8A:
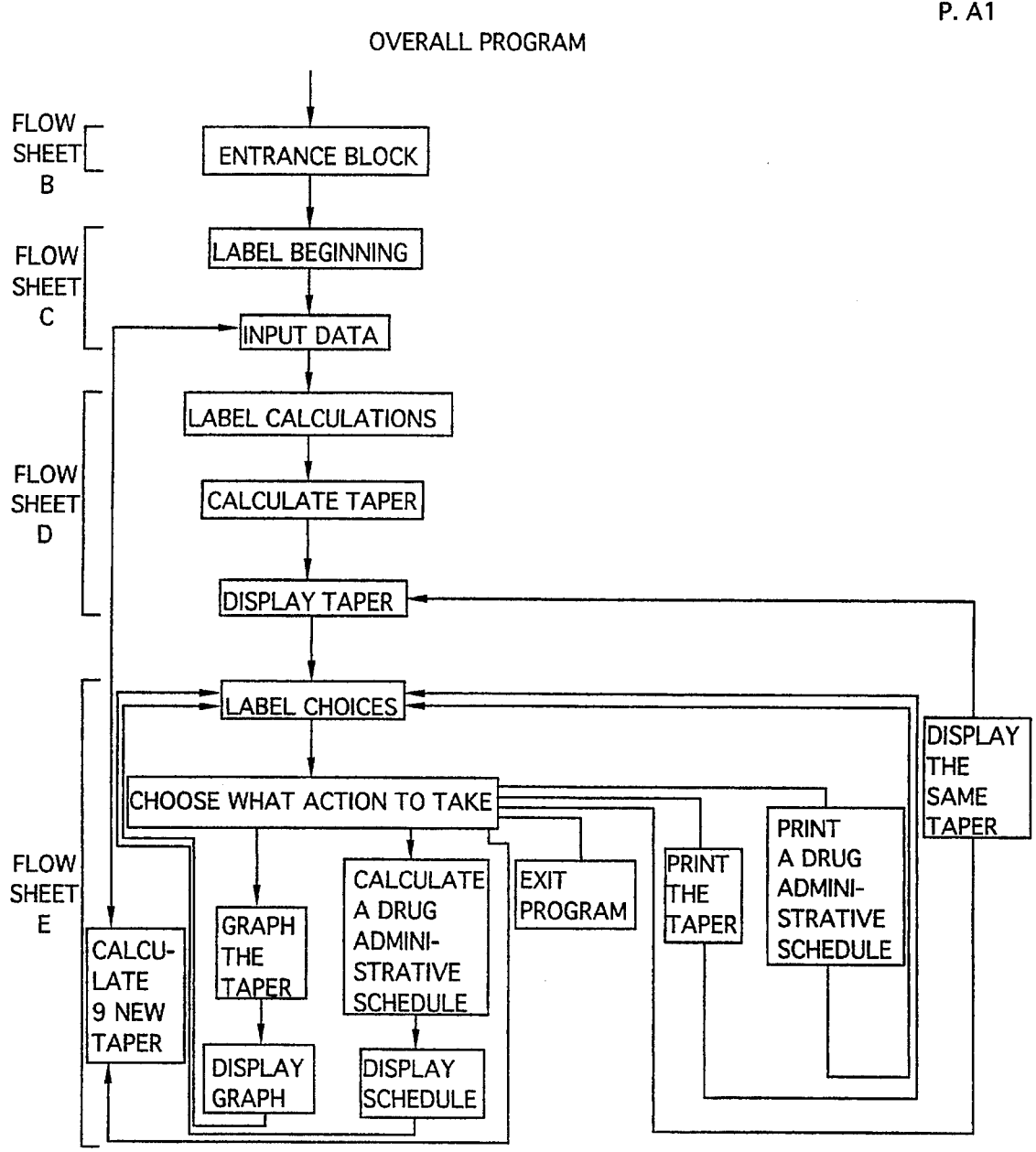
Figure 8B:
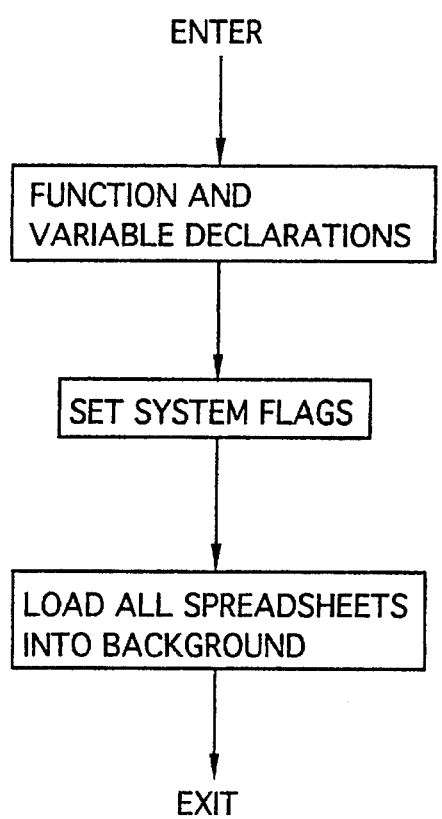
Figure 8C:
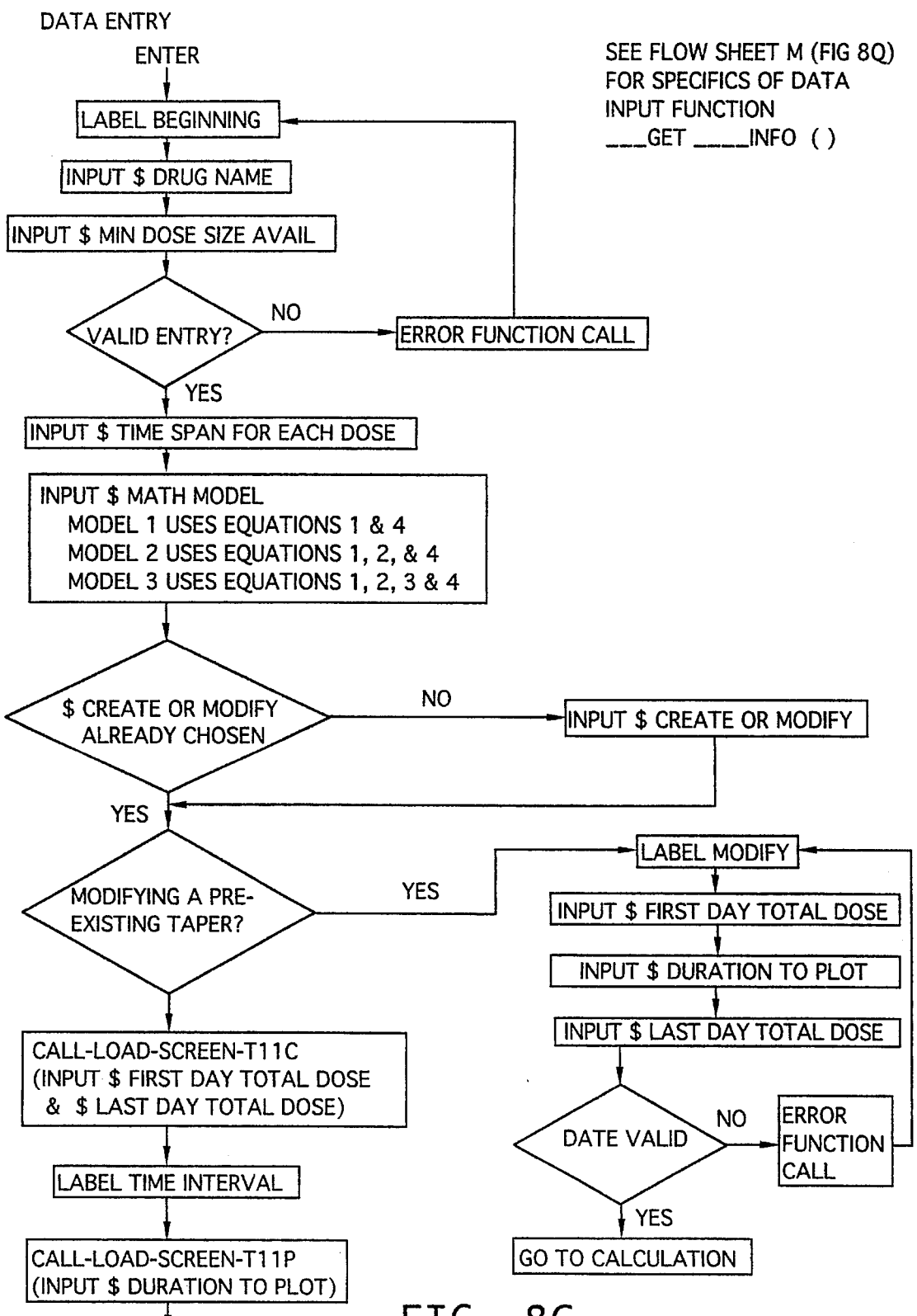
Figure 8D:
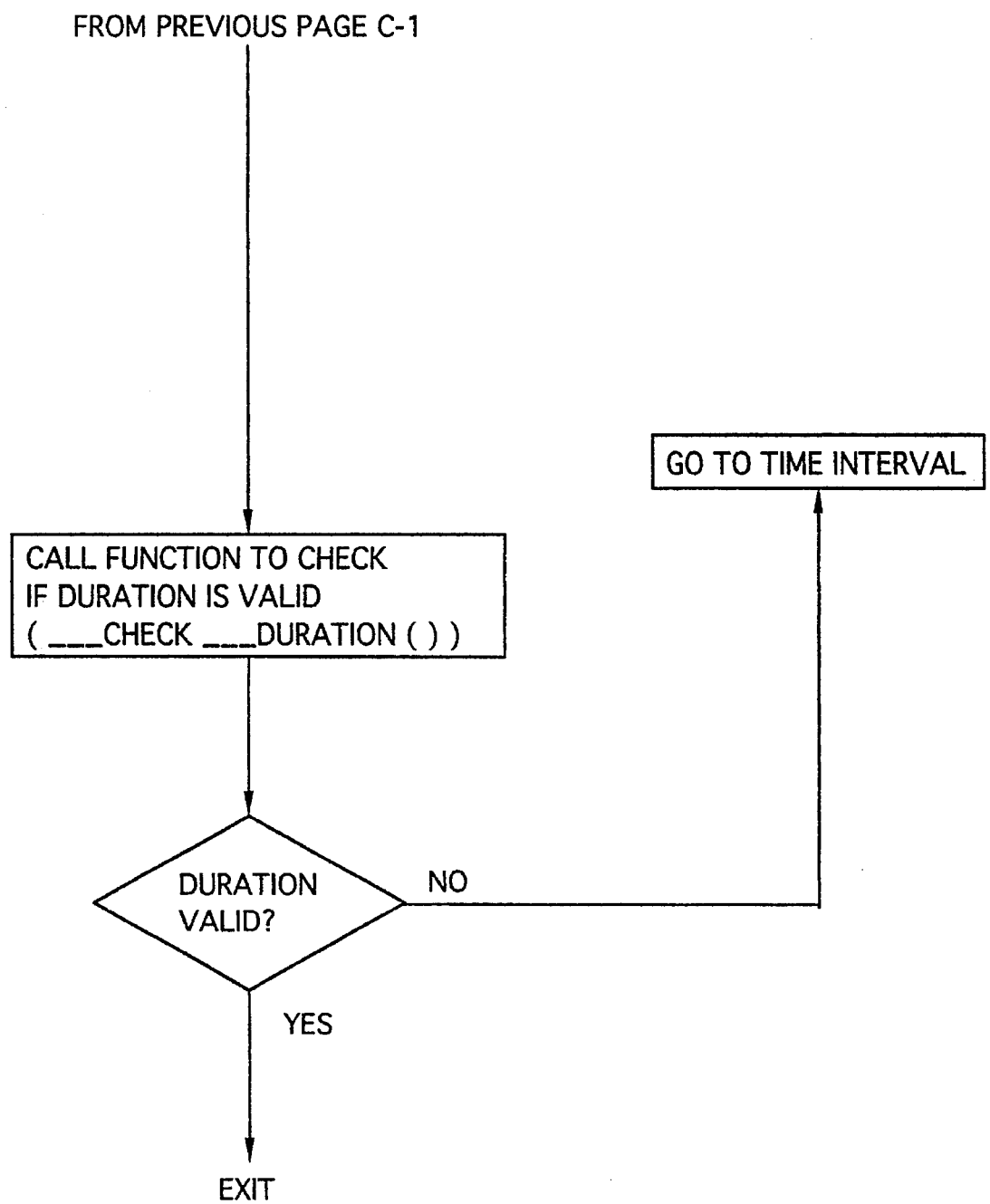
Figure 8E:
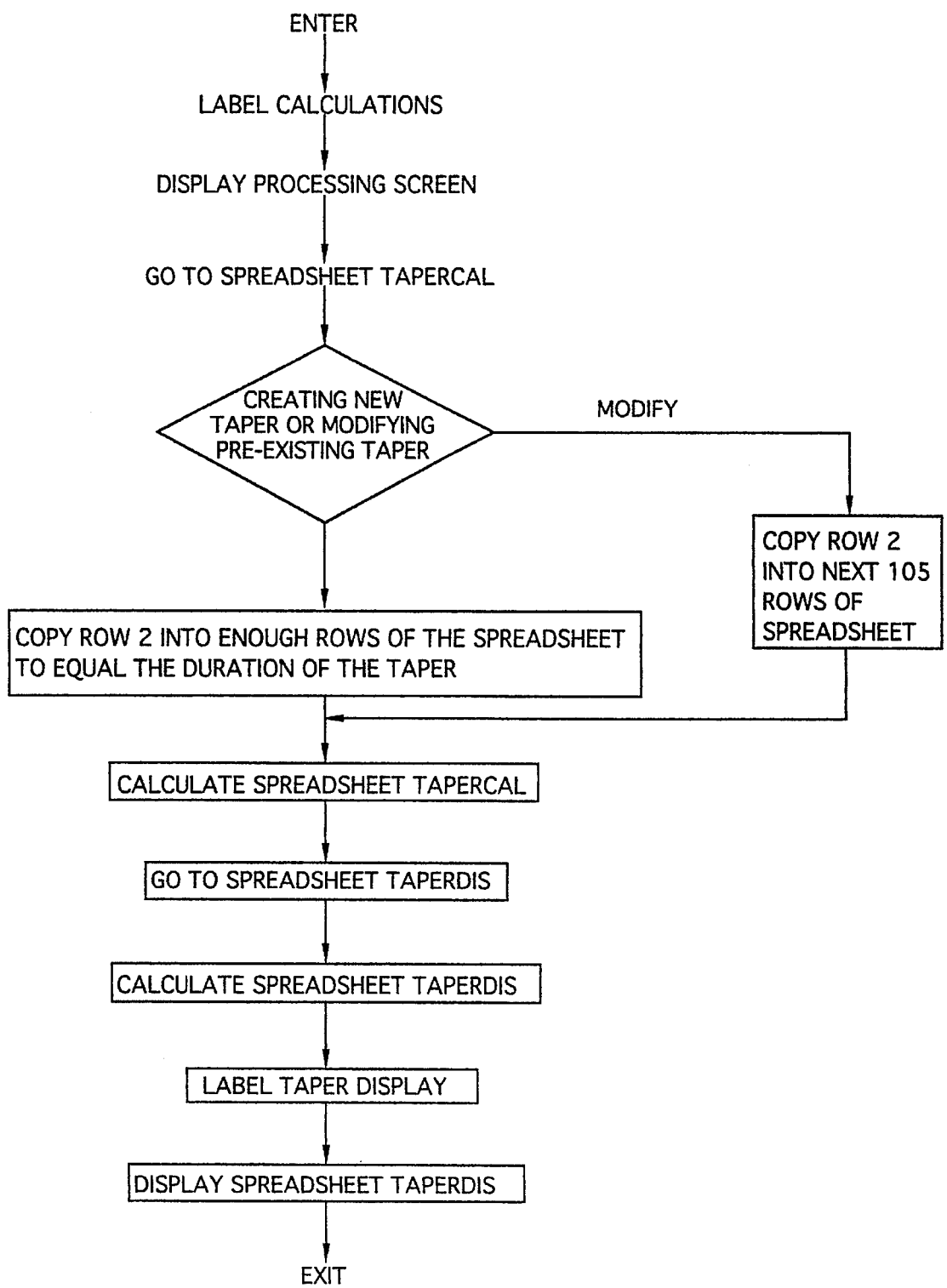
Figure 8F:
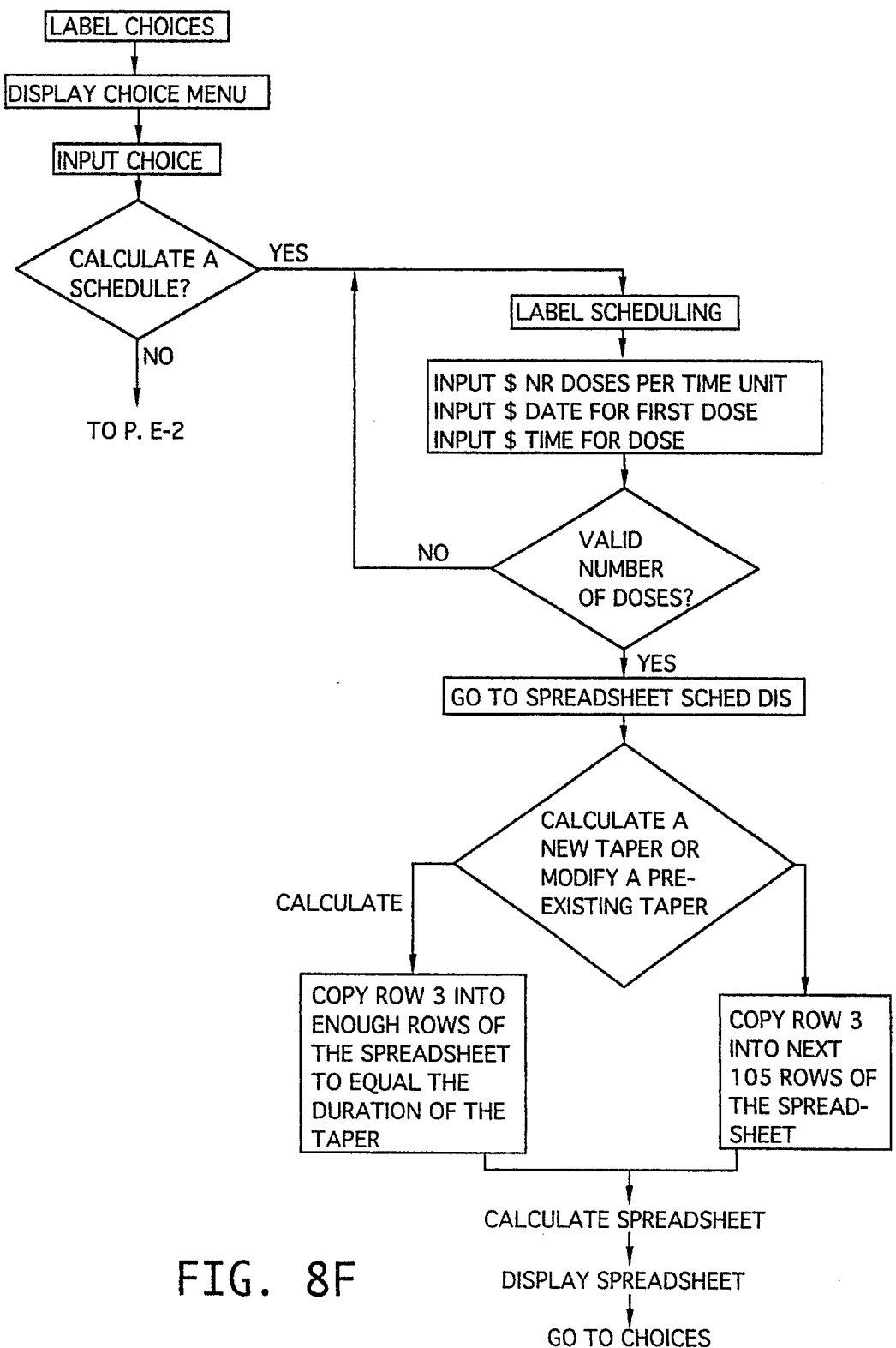
Figure 8G:
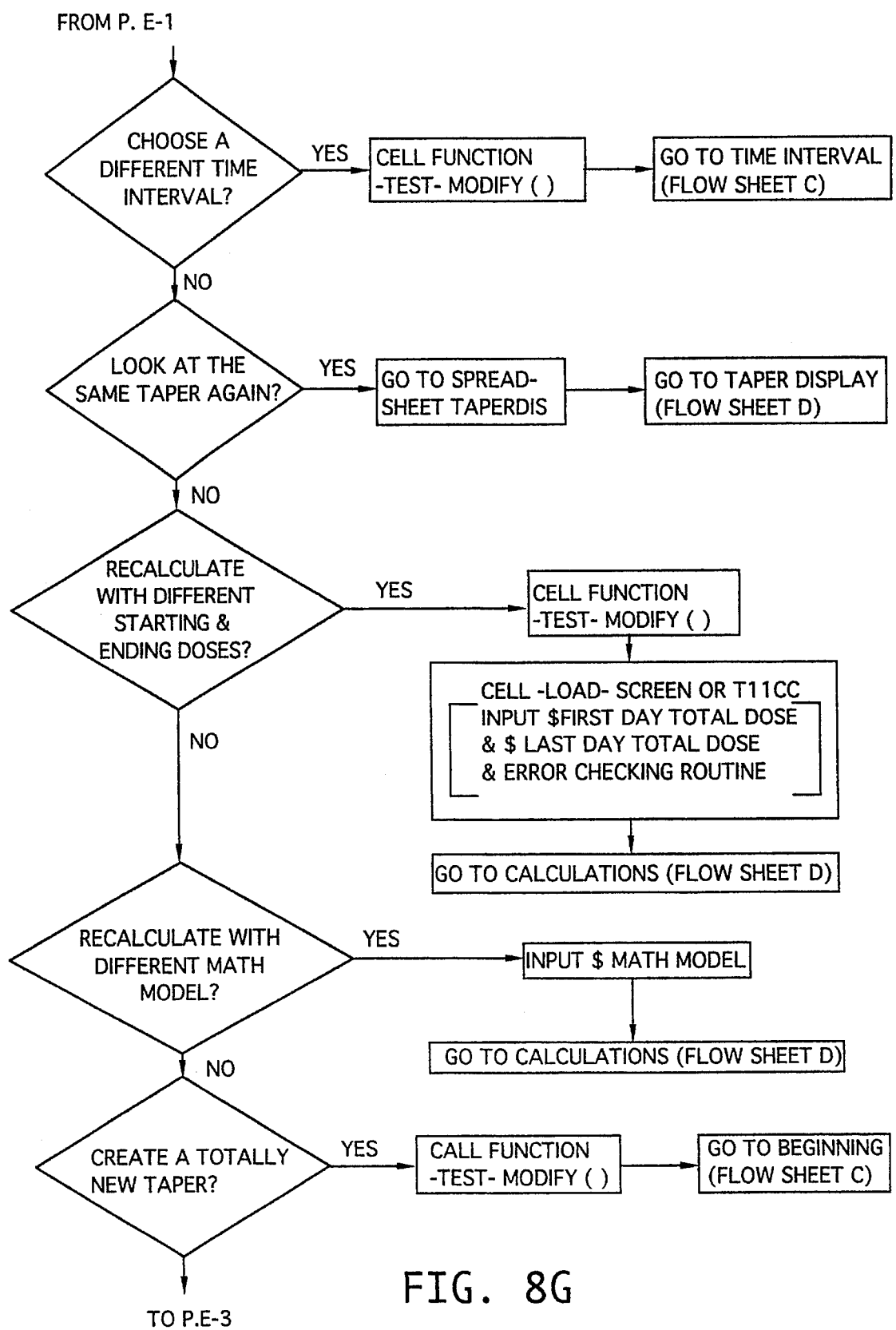
Figure 8H:
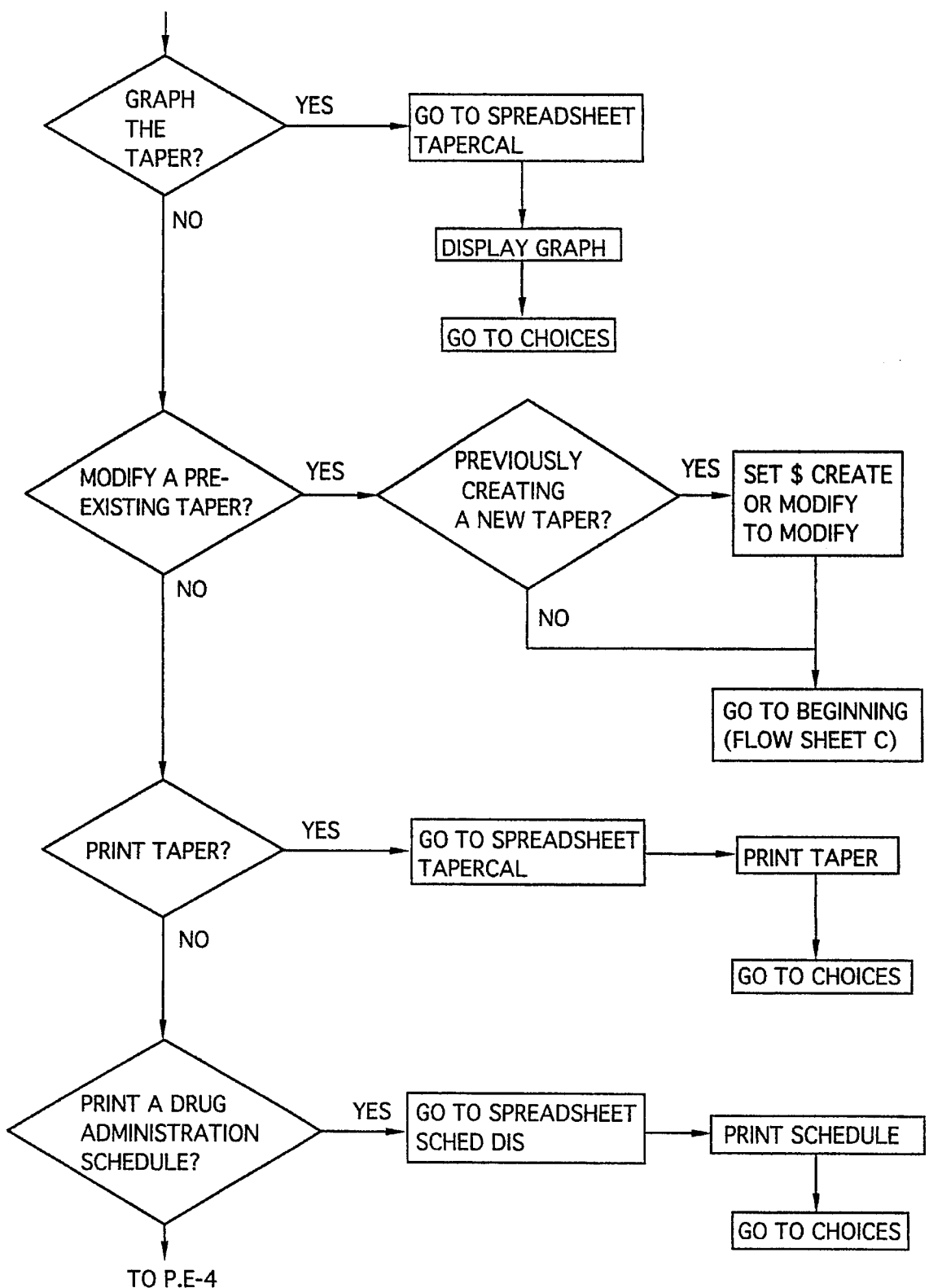
Figure 8I:
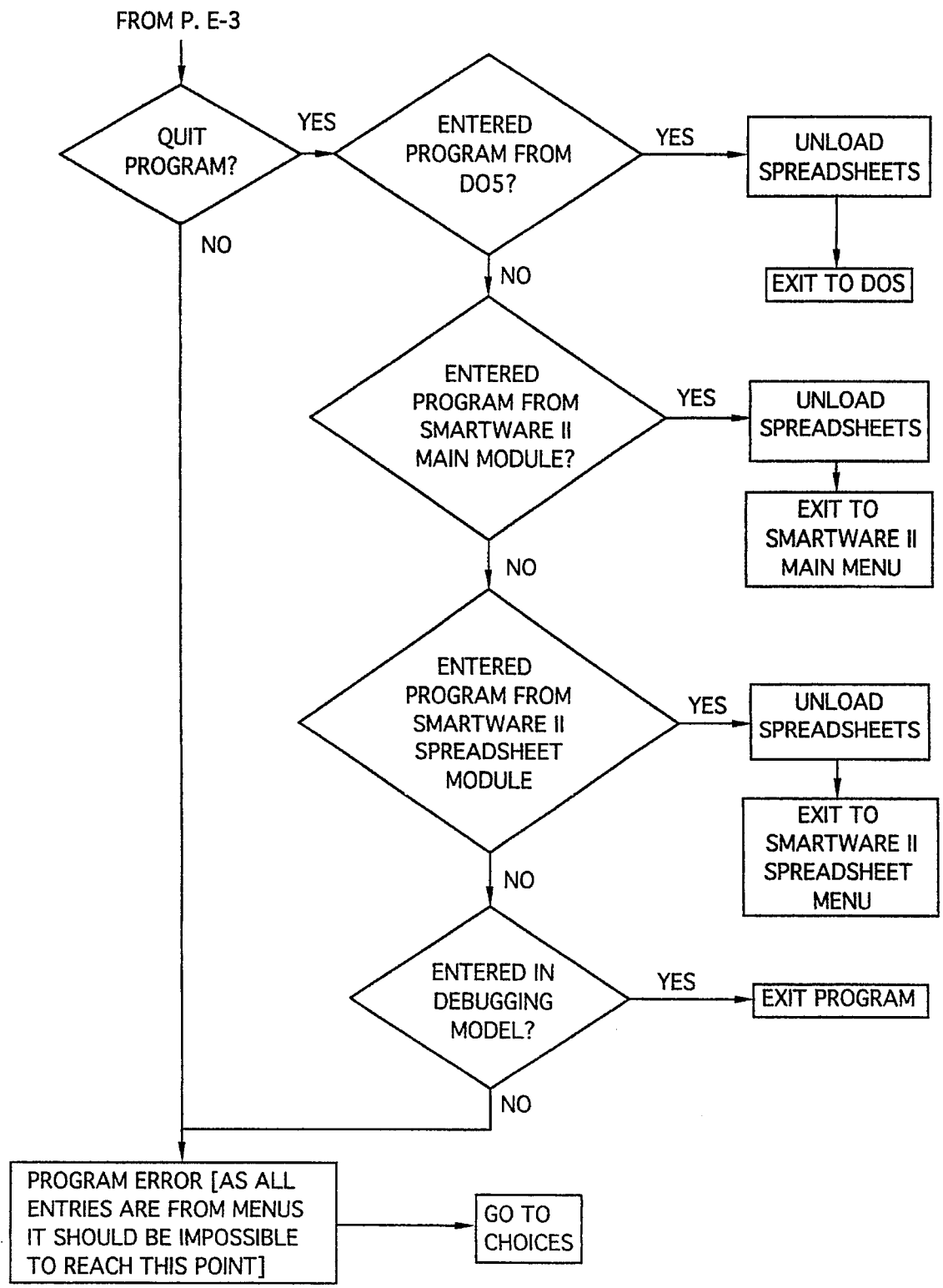
Figure 8J:
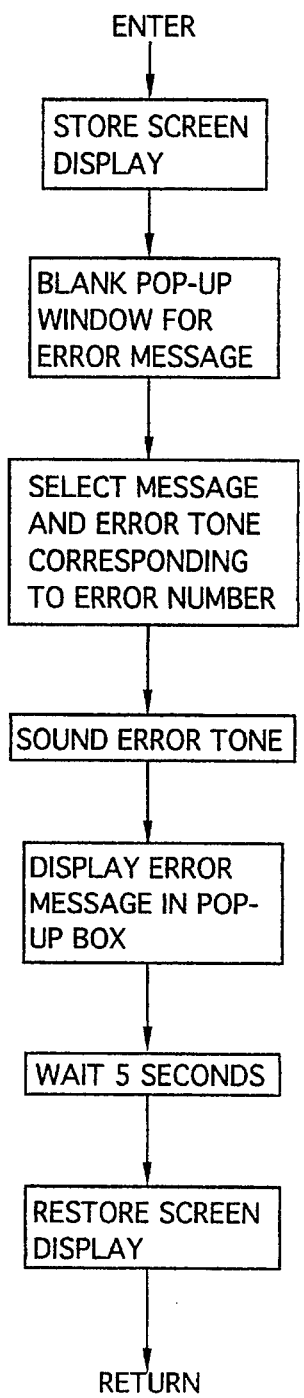
Figure 8K:
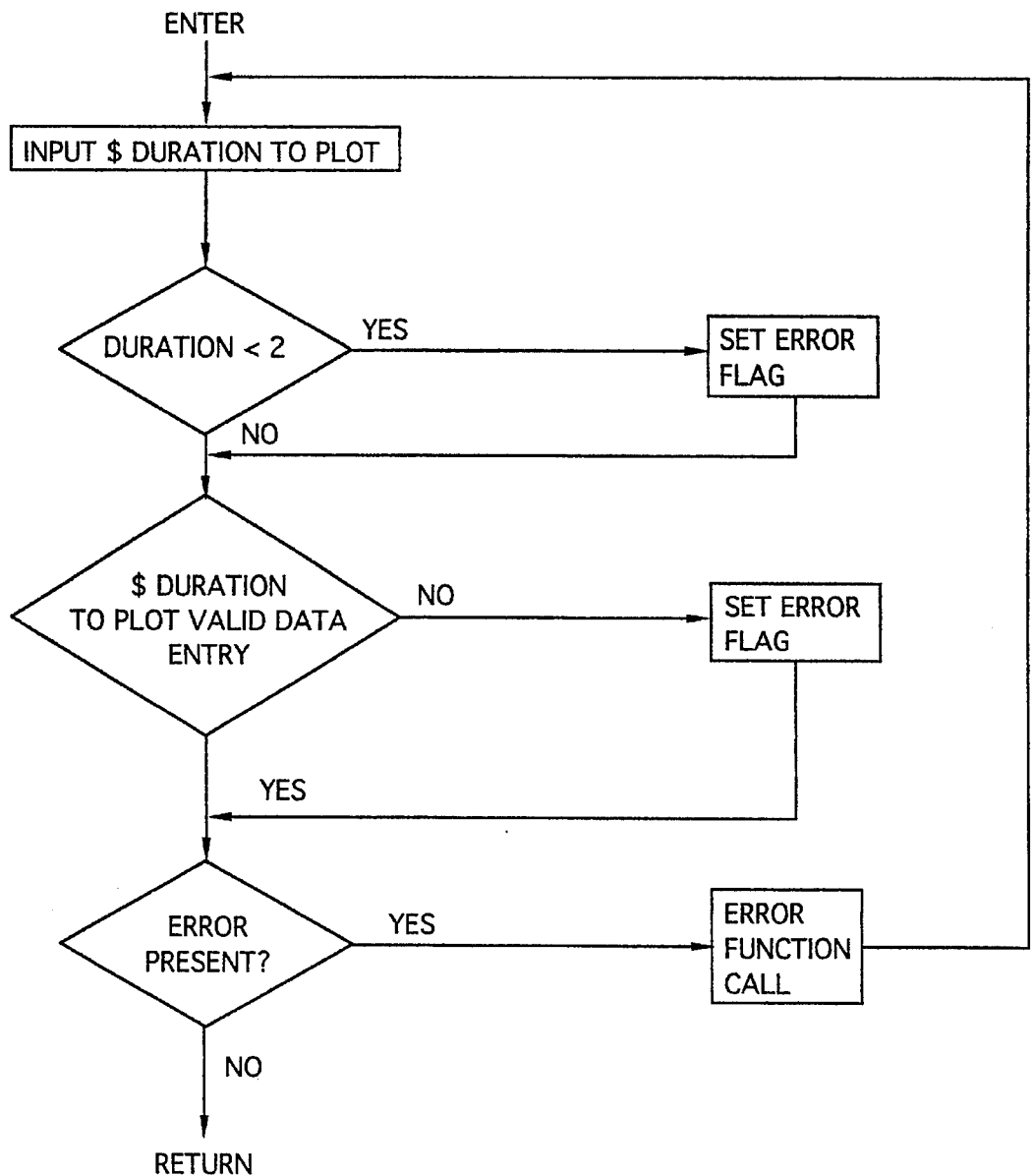
Figure 8L:
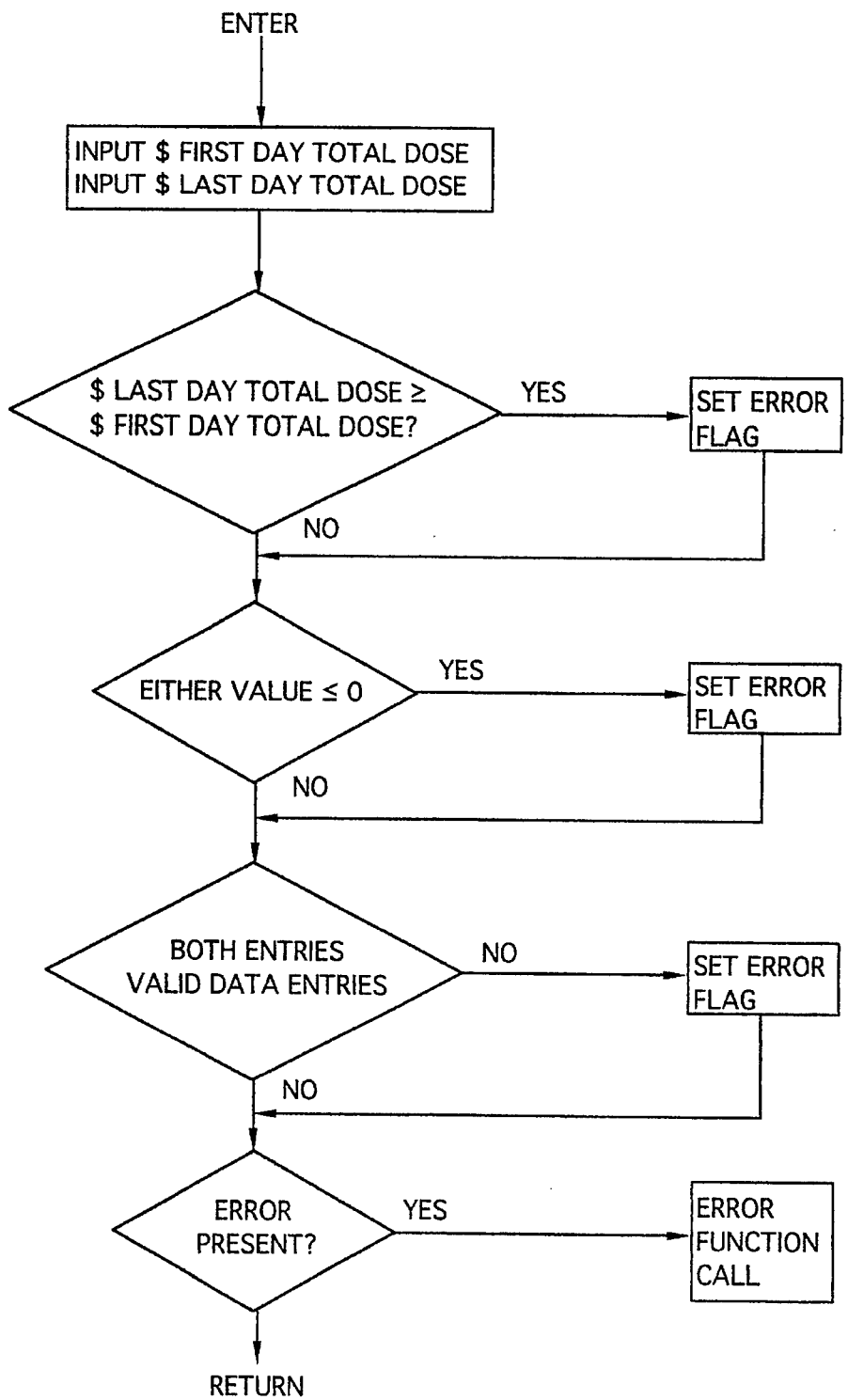
Figure 8M:
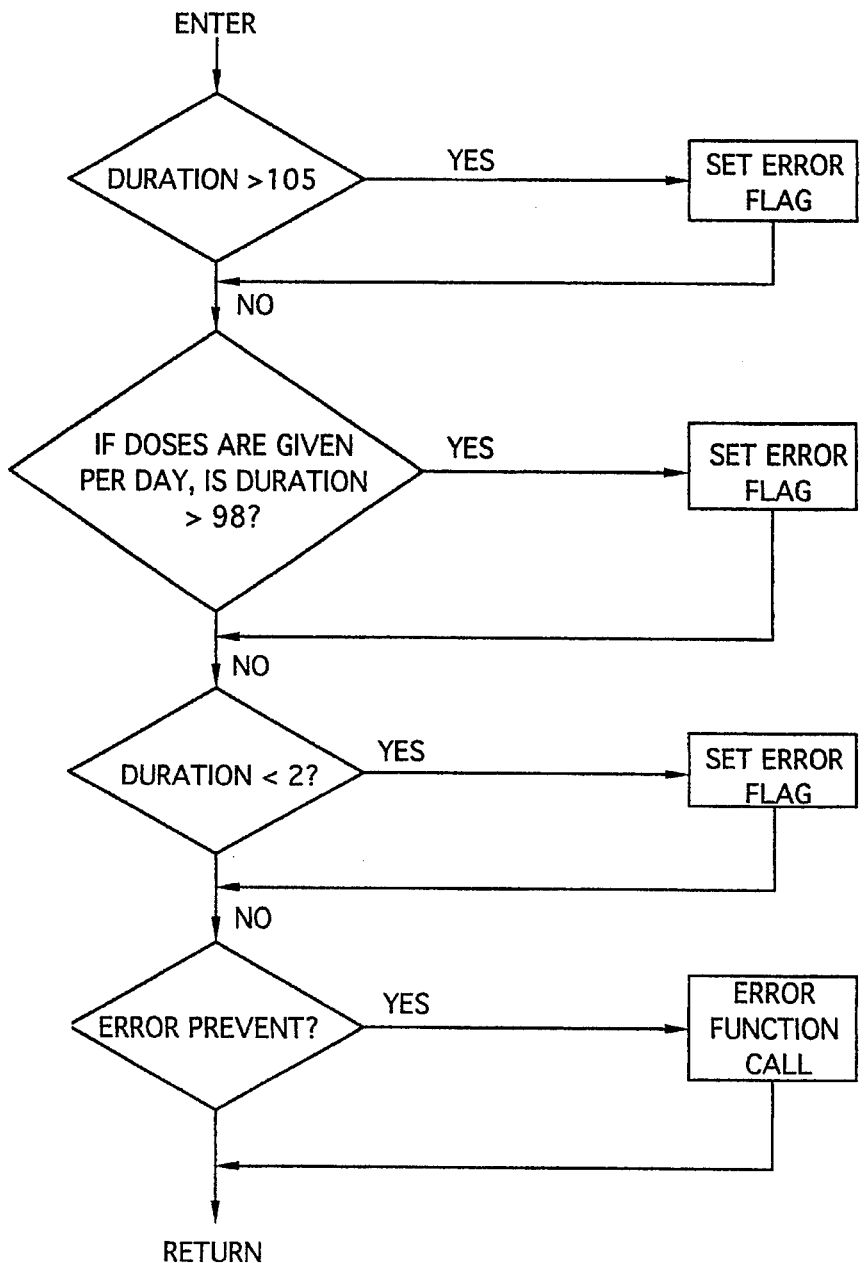
Figure 8N:
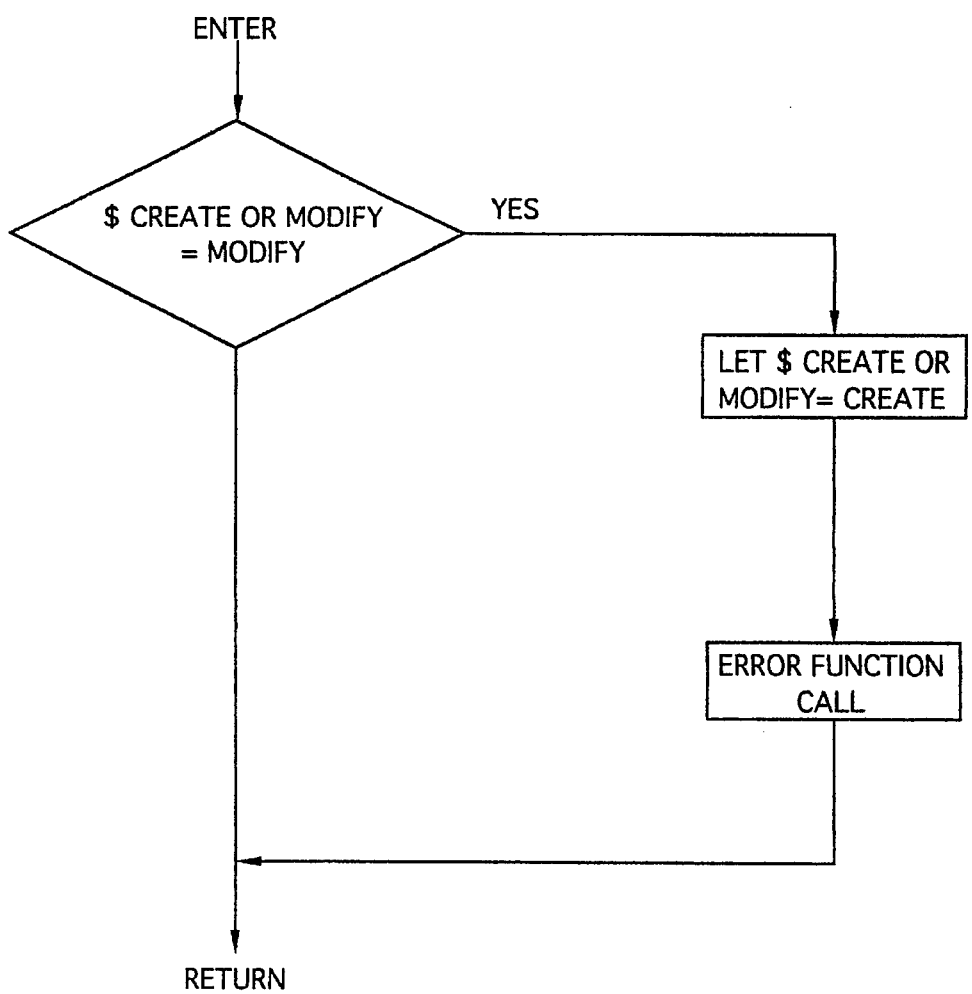
Figure 80:
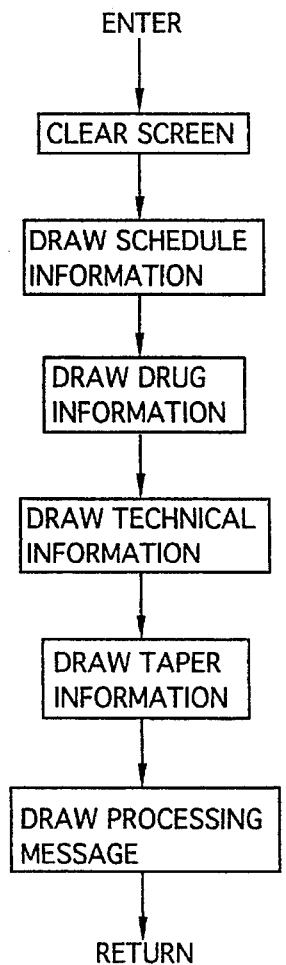
Figure 8P:
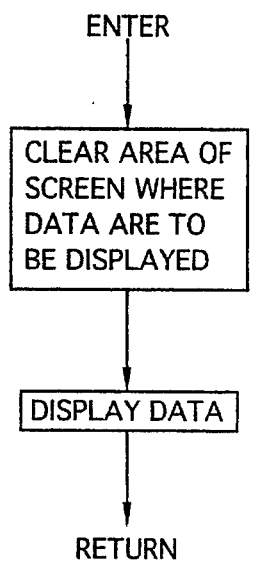
Figure 8Q:
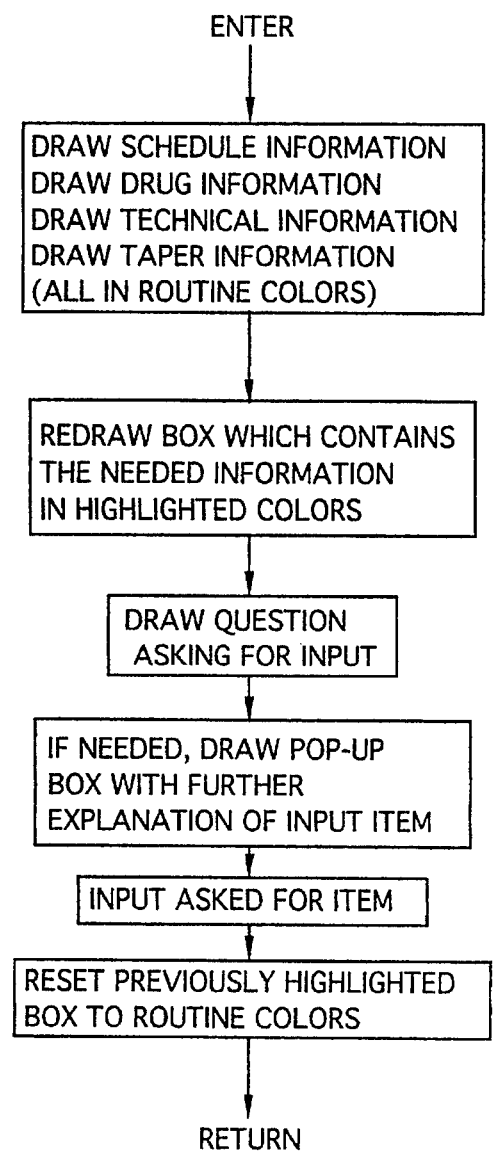

FIG. 8E, box "Calculate Spreadsheet Tapercal", incorporates equations 1–6 of the algorithm as described in the Description of the Preferred Embodiments and the Appendix, pages A17–A22 entitled "Formulas for Worksheet Tapercal".

MODE OF OPERATION

This algorithm was tested in sixteen patients needing detoxification from psychoactive drugs. Initial doses and durations for detoxification were chosen by physicians using the same criteria as applied in the inpatient Alcoholism and Drug Dependence Unit of the Mayo Clinic in Rochester, Minn. Exponential drug tapers were then calculated using the model. Doses were not given if the patients showed signs of intoxication, or extra doses were given if the patients were in withdrawal.

All sixteen patients were successfully tapered from their medications. More so, there was a significant ($p<0.01$) reduction in the total amount of drug needed for detoxification compared to a traditional linear taper. Mathematically quantifiable drug reduction schedule can be used to successfully taper patients from psychoactive medications. In addition, this technique provides for lower total doses of drugs (the "area under the curve") than does a more typical approach.

The teaching of the process of the present invention provides three new, specific advantages over previous techniques of calculating drug tapers:

a. The process mathematically determines a quantifiable, reproducible drug taper.
 b. The process uses the computer to provide the practitioner with alternative drug tapers.
 c. The process uses the computer to calculate an actual drug administration schedule.

The mathematical drug taper algorithm is reproducible from patient to patient. Because the drug taper can be calculated from two points, it also allows for a drug taper to be corrected if a patient needs extra medication or less medication than originally thought. By using two known doses the patient required, such as the first dose and the most recent, a new drug taper can be calculated based upon the patient's actual need.

Figure 4:
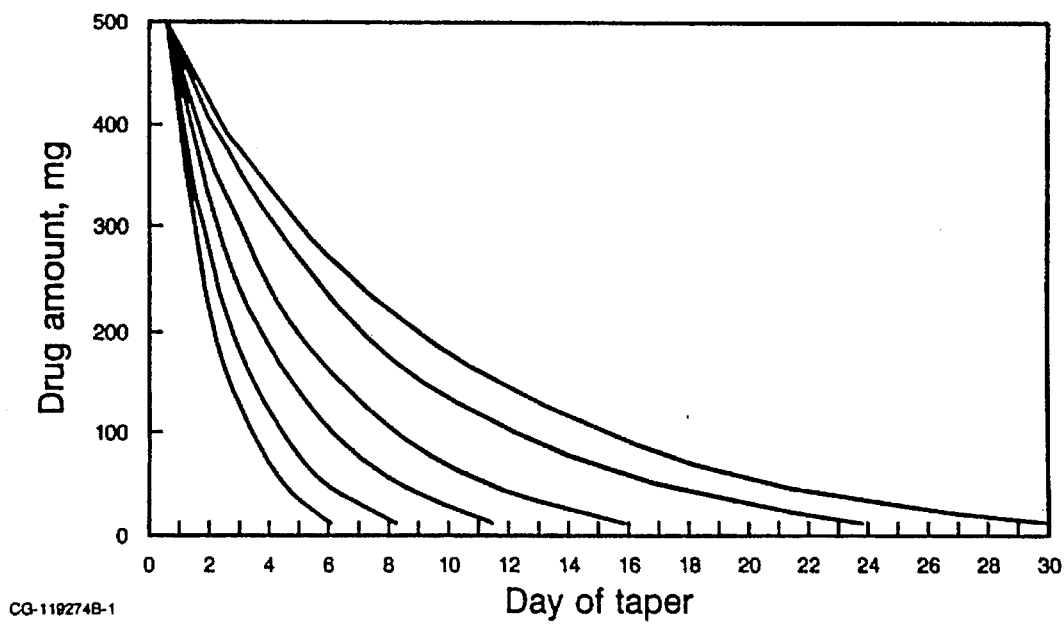
FIG. 4 illustrates alternative drug tapers.
Figure 5:
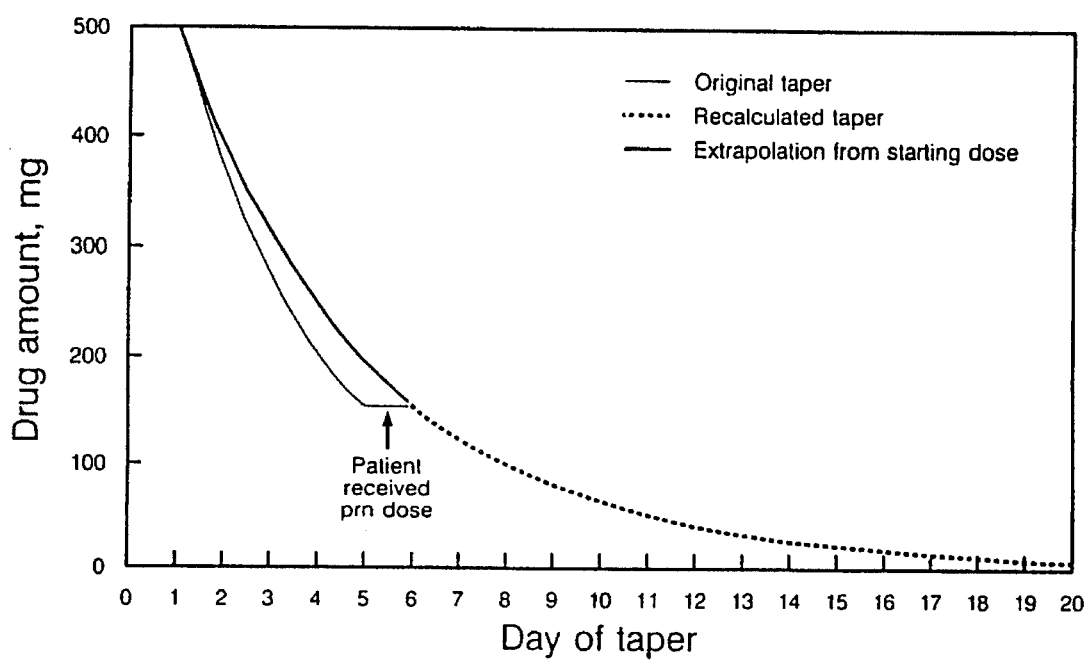
FIG. 5 illustrates a recalculated drug taper.

In practice, the physician must consider many factors to determine the proper drug taper schedule for a patient: the patient's overall health, the risk of the patient experiencing drug-withdrawal symptoms, the pharmacokinetics of the drug in use, etc. By using the computer, the physician can be shown several alternative drug tapers, either in tabular or graphic form (FIG. 4), and from these may chose the most appropriate drug taper for his patient. At present, most physicians currently decide upon a drug taper without comparing what the actual drug tapers would look like.

Once a drug taper is chosen, it must then be converted into what is administered to the patient. In many drugs, doses are determined as total dose over a 24-hour period, and then the dose is divided and several, smaller doses given during that 24-hour period. This calculation may involve several unequal doses over that 24-hour period, adjusted to match an individual's daily pattern. Currently, the calculation of these doses is typically done by hand, and can require as much as fifteen to thirty minutes for a complicated schedule. This schedule must also be transcribed into a written form for use by both the hospital pharmacy and the nursing service for hospitalized patients. For outpatients, the schedule must be converted into a form usable by the patient, such as "Take 2 pills at 3 p.m." Using the computer to do these calculations not only speeds the process, but also eliminates human error in copying and transcription.

Currently, the program utilizes the following as input:

1. The two drug parameters which can be utilized:
  a. Initial dose and duration of taper;
  b. Initial dose and final dose;
  c. Any two specific doses; or
  d. One dose and percent decrement
 2. Drug Name.
 3. Patient identification.

and offers as output:

4. Calculated taper
  a. Tabular form.
  b. Graphic form.
 5. Option for recalculation of taper.
 6. Comparison of two tapers.
 7. Drug administration schedule with appropriate identification, and times for pharmacy and nursing usage.
 8. Drug schedule for patient usage, listed in dosage multiples (such as number of pills), for outpatient use.

Alternative functions might include certain decision making functions, such as offering suggested schedules based on the drug, or suggested drug taper durations based on the drug, the patient status, the length of time the patient has used the drug, etc. In addition, alternative functions might consider drug interactions when patients are taking multiple drugs.

Drug tapers are used in clinical medicine in a variety of situations. Not only do drug tapers occur routinely when taking patients off psychoactive medications, but they are also used whenever there is concern of how the patient will react without the medication. A simple example would be when a patient needs to be taken off an anticonvulsant. Thus far, the common advice is to proceed with drug tapers "slowly," and nobody has presented a quantifiable technique for calculating drug tapers. One describes such a method, utilizing an exponential drug taper. Initial research with this process shows that not only does it work well, and that it actually uses less medication than does a standard drug taper. This process only recently has become useful, for it requires ready access to computers for the clinician. However, our approach has utilized computers for at least four new functions not commonly used previously; quantifying a drug taper, allowing a clinician to view alternative drug tapers to facilitate choosing the most appropriate clinical drug taper, automating the calculation and printing of drug administration schedules for nursing, pharmacy, and patient usage, and recalculating a drug tapering if required based on a patient's actual clinical response.

EXAMPLE

Appendix 1 illustrates various supplements comprising one application of the algorithm on a computer, and provided output. This particular program runs as several spreadsheets, on a commercially available package, SmartWareII by Informix Software, Inc., Lenexa, Kans. The sample spreadsheets contain data from the same taper.

1. Copyright statement from SmartWareII.
 2. Macro program which runs the entire taper, run in SmartWareII spreadsheet module. This program is internally documented. The parameters which the program uses are:
  A. $MinDoseSizeAvail: the minimum dosage size of the drug available. This datum is read as a string, MinDoseSize, and then converted to this numeric variable.
  B. $CreateOrModify: whether you want to create a new taper, or modify an already existing taper.
  C. $DurationToPlot: how long the taper should last.
  D. $TimeForDose_1 (through _6): a string indicating what time dose number 1 will be given, to be printed as a heading on the drug administration schedule.
  E. $TimeSpanForEachDose: the units of time in which the taper is calculated.

F. $NrDosesPerTimeUnit: how many doses will be given in each time unit. For example, if the $TimeSpanForEachDose is given in days, $NrDosesPerTimeUnit would be how many doses per day.

G. $LastDayTotalDose: how much drug to give in the last time unit.

H. $FirstDayTotalDose: how much drug is given in the first time unit.

I. $DrugName: a string with the name of the drug.

J. $MathModel: which mathematical model to use. Model 1 uses only equations 1 and 4. Model 2 uses equations 1, 2, and 6. Model 3 uses equations 1, 2, 3, and 4.

K. $DateForFirstDose: what date the first dose will be given, if doses are given per day, per week, or per month, otherwise what time the first dose will be given if doses are given per hour or per minute.

3. Example of an input screen asking for some data for the program, and also showing all of the parameters for which the program asks.

4. Example of spreadsheet Tapercal. This is the spreadsheet which actually calculates the taper. Column 1 contains the percentage decrement. For example, each day's total dosage is 79.43282% of the previous days dosage. Column 2 contains $k_1 k_2^i$. Column three contains:

$$\sum_{i=1}^{t} k_1 k_2^i$$

Column four contains the amount to be given, rounded to multiples of the minimum dosage size. Column five contains the total amount given:

$$\sum_{i=1}^{t} G(i)$$

Column six contains the time interval number. For example, day 1, 2, 3, etc.

5. Formuli comprising spreadsheet Tapercal.

6. Example o# spreadsheet Taperdis. This spreadsheet displays the taper on the computer.

7. Formuli comprising spreadsheet Taperdis.

8. Example of spreadsheet SchedDis. This spreadsheet is 11 columns wide, and is printed on two pages. This spreadsheet calculates and displays the drug administration schedule. Column 1 contains the total dose. Column two contains the time unit, for example, the date in this example. Columns 3 through 8 contain the amount to be given in the first, second, third, fourth, fifth and sixth dose per time unit. In this example, only four doses per day are being given, so columns 7 and 8 remain blank. Column 9 contains the total daily dose in multiples of the minimum dosage size. In this example, how many five milligram doses make up the total daily dose. Column 10 is the average number of minimum doses per time unit. In this example, for each of the four doses per day, it tells how many five milligram doses must be given on average. Column 11 is the remainder of minimum dosage sizes still to be given after the minimum dosage sizes have been given. In this example, it is how many five milligram doses must be given after the average five milligram doses (listed in column 10) have been given at each of the four times per day.

9. Example of how SchedDis looks on the computer screen.

10. Formuli comprising spreadsheet SchedDis.

| Page | Description of Appendix Page |
|---|---|
| 1 | Copyright statement for SmartWareII, the commercial package on which this program runs. |
| 2–14 | Application program which runs the entire taper (see flowsheets A through M) |
| 2 | Entrance Block (flowsheet B) |
| 2–3 | Data Entry (flowsheet C) |
| 3 | Calculations (flowsheet D) |
| 3–6 | Choose Action (flowsheet E) |
| 6 | Data Entry for modifying a pre-existing taper (flowsheet C) |
| 7–14 | Functions (flowsheets F–M) |
| 7–8 | Error Function (flowsheet F) |
| 8 | _Load_Screen_T11D() (flowsheet G) |
| 8 | _Load_Screen_T11C() (flowsheet H) |
| 9 | _Check_Duration() (flowsheet I) |
| 9 | _Test_Modify() (flowsheet J) |
| 9 | Display Processing Screen (flowsheet K) |
| 9 | Draw Schedule Information Box (flowsheet L) |
| 10 | Draw Drug Information (flowsheet L) |
| 10 | Draw Technical Information (flowsheet L) |
| 10–11 | Draw Taper Information (flowsheet L) |
| 11–14 | Input Function (flowsheet M) |
| 15 | Input Screen: The four small boxes at the top are drawn by functions: _Draw_Drug_Info() _Draw_Tech_Info() _Draw_Taper_Info() _Draw_Sked_Info() If this screen were in color, the "Taper Information" box would be highlighted. The entire screen is produced by the _Get_Info() function, which is the date input function. This screen displays the parameters for the sample taper shown throughout this example. |
| 16 | Spreadsheet TaperCal: To save both memory and processing time, only the first two rows are stored in memory. As rows 2 and higher contain identical formulas, row 2 is duplicated during processing to equal the size of the taper. This has two advantages: 1) less memory is used to store the spreadsheet, and 2) less time is used to calculate the spreadsheet as there are no redundant rows. |
| 17–22 | Formulas for spreadsheet TaperCal |
| 23 | Spreadsheet TaperDis: The function of this spreadsheet is solely to take the information in column 4 of spreadsheet TaperCal and display it in an easily readable form. Columns 1, 3, 5, 7, 9, 11 and 13 contain the taper doses in sequential order. Columns 2, 4, 6, 8, 10, 12 and 14 are the lines which divide the columns. Highlights are placed appropriately depending on the time interval. In this example, as doses are given per day, hash marks are placed every seven days. |
| 24–29 | Formulas for spreadsheet TaperDis. |
| 30–31 | Spreadsheet for SchedDis: This spreadsheet both calculates and displays a drug administration schedule. |
| 32 | Spreadsheet SchedDis: This demonstrates how the spreadsheet appears on a computer screen. Only the portion that displays the schedules is visible on the screen. The portions of the spreadsheet only used for calculation are not visible (i.e., columns 9–11 are not visible). The same strategy to save memory processing time as is used in Spreadsheet TaperCal is used with this spreadsheet; it is expanded during processing to equal the size of the taper. |
| 33–43 | Formulas for spreadsheet SchedDis. |

DISCUSSION OF EXAMPLE ON PAGE 15 OF APPENDIX 1

This example is for a hypothetical drug "Sample Drug". The smallest dosage size is a 5 mg capsule. The patient is taking 500 mg/day of the drug and one wants to taper the patient down to only 50 mg/day of the drug, and wants to take 10 days to do it. One wants to do this using only formulas 1 and 5. One is creating, then, a new taper from scratch.

After inputting the data (p.15) the program calculates the taper (p.16). This calculation is not visible to the user. The taper is then displayed (p.23).

The user is shown the Choose Action menu (p.3–6, flowsheet E). If one chooses to create a drug administration schedule, one is asked to input specifics about the schedule (Scheduling Information box on p. 15). In this example, one wants to give "Sample Drug" four times a day, at 7 a.m., 12 noon, 5 p.m., and 10 p.m. The first reduced dose is to be given on Apr. 20, 1990.

The actual drug administration schedule is shown on spreadsheet SchedDis (p.32). The total daily dose (column 1) is divided into 4 doses (columns 3, 4, 5 and 6) to be given at 7 a.m., 12 noon, 5 a.m., and 10 p.m. For example, on the first day of the taper, Apr. 28, 1990, the patient will receive a total of 50 mg of "Sample Drug"; 15 mg at 7 a.m., 10 mg at 12 noon, 10 mg at 5 p.m., and 15 mg at 10 p.m. Note that all doses are in sizes that can actually be given. If the 50 mg were merely averaged over all 4 times to 12.5 mg, it would be impossible to administer, as "Sample Drug" comes only in 5 mg multiples. Instead the program divides the 50 mg in multiples of 5 mg.

After viewing drug administration schedule, the user is again shown the Choose Action menu to let him either print the output, do some more calculating, or leave the program.

Mechanically, this example program runs as an application program on a commercially available integrated package, SmartWareII (p.1) The Macro program (pp.2–14) can be entered directly from DOS, in which case the use of SmartWareII is transparent to the user, or from the SmartWareII main and spreadsheet modules. The macro program gets all input for use by the three spreadsheets, TaperCal (pp.16–22), TaperDis (pp.23–29), and SchedDis (pp. 30–43).

The user does not know he is working with spreadsheets. The program controls which data goes into the spreadsheet and which spreadsheet is being used at any given moment. All calculations are done in the background, and only the results are displayed on the screen.

The program also does error checking so invalid entries are not placed in the spreadsheets. Rather, the user is told what his mistake was and how to correct it, and then asked to reenter correct data. In cases where the program knows what the correct entry should be, it will use it, notifying the user it is doing so.

Various modifications can be made to the present invention without departing from the apparent scope hereof.

APPENDIX 1

```
/*******************************************************************
/*******************************************************************
' Drug Taper -- Main Module                                        *
'                                                                  *
/*******************************************************************
/*******************************************************************

/*******************************************************************
' Declarations                                                     *
'                                                                  *
/*******************************************************************
/************************************* FUNCTION DECLARATIONS
GLOBAL   _ERROR(), _Load_Screen_T11C(), _Load_Screen_T11D(), _Check_Duration()
GLOBAL   _TEST_MODIFY(),_ProcDply()
GLOBAL   _DRAW_DRUG_INFO(),_DRAW_TECH_INFO(),_DRAW_TAPER_INFO()
GLOBAL   _DRAW_SKED_INFO(),_GET_INFO()

/************************************* VARIABLE NAME DECLARATIONS
GLOBAL   $Error
PUBLIC   $MinDoseSizeAvail,$CreateOrModify, $DurationToPlot
PUBLIC   $TimeForDose_1, $TimeForDose_2, $TimeForDose_3
PUBLIC   $TimeForDose_4, $TimeForDose_5, $TimeForDose_6, $TimeSpanForEachDose
PUBLIC   $NrDosesPerTimeUnit, $LastDayTotalDose, $FirstDayTotalDose
PUBLIC   $DrugName, $MathModel
PUBLIC   TimeUnit, $DateForFirstDose,MinDoseSize,ModifyDur
PUBLIC   Screen_Memory
EXTERNAL QUIT_FLAG
LOCAL    X,Auto_Help_Status,Per1,$OptionChosen,RowNumber /************************************* EXTERNALLY NEEDED VARIABLES
LOCK BOTH  $MinDoseSizeAvail, $CreateOrModify, $DurationToPlot
LOCK BOTH  $TimeForDose_1, $TimeForDose_2, $TimeForDose_3
LOCK BOTH  $TimeForDose_4, $TimeForDose_5, $TimeForDose_6
LOCK BOTH  $TimeSpanForEachDose, $NrDosesPerTimeUnit, $LastDayTotalDose
LOCK BOTH  $FirstDayTotalDose, $DrugName, $MathModel
LOCK BOTH  TimeUnit, $DateForFirstDose, MinDoseSize /*******************************************************************
' Entrance Block                                                   *
'                                                                  *
/*******************************************************************

/************************************* Set Initial values
SINGLE-STEP OFF
_ProcDply("L O A D I N G")
^CBREAK OFF
REPAINT OFF
ON-ERROR OFF
SmartPeek $_auto Auto_Help_Status
AutoHelp Off
Tools Directory New-Directory "C:\SMARTII\TAPER\"
comment QUIET OFF
comment SINGLESTEP ON
/************************************* Load the Spreadsheets
FILE ACTIVATE "SchedDis"
FILE ACTIVATE "TAPERCAL"
FILE ACTIVATE "TAPERDIS"
```

```
      JUMP BEGINNING
END IF
_Get_Info("$TimeSpanForEachDose",FGSTANDARD,BGSTANDARD,FGINVSTANDARD,BGINVSTANDARD)
_Get_Info("$MathModel",FGSTANDARD,BGSTANDARD,FGINVSTANDARD,BGINVSTANDARD)
/************************************** Find out what type of action
/************************************** (only if option not already chosen)
IF (($OptionChosen <> 8) AND ($OptionChosen <> 6))
    _Get_Info("$CreateOrModify",FGSTANDARD,BGSTANDARD,FGINVSTANDARD,BGINVSTANDARD)
END IF
/************************************** If modifying a taper,
/************************************** Jump to the modify block
IF $CreateOrModify == "MODIFY"
    JUMP MODIFY
END IF
/************************************** Here to create a new taper
/************************************** Here to find time intervals
_Load_Screen_T11C()
LABEL TIMEINTERVAL
_Load_Screen_T11D()
/************************************** Checks too long duration
_Check_Duration()
IF ($Error)
    JUMP TIMEINTERVAL
END IF
/************************************** Here to calculate new taper
LABEL CALCULATIONS
_ProcDply("P R O C E S S I N G")
AT r1c1
 SHEET GOTO SHEET "tapercal"
LET per1 = $DurationToPlot - 2
AT r3c1
 EDIT DELETE ROWS 120
AT r3c4
  EDIT COPY DOWN SINGLE-CELL COPIES 105

/************************************** Copy Spreadsheet Cells

IF ($CreateOrModify == "CREATE")
    AT R2C1
     EDIT COPY DOWN ROW LENGTH 6 COPIES per1
END IF
SINGLE-STEP OFF
DEBUG OFF IF ($CreateOrModify == "MODIFY")
    AT r2c1
     EDIT COPY DOWN ROW LENGTH 6 COPIES 105
END IF
AT r1c1 recalc
AT r18c1
 SHEET GOTO SHEET "taperdis"
recalc
LABEL TAPERDISPLAY
REPAINT
/************************************** This line clears the bottom of
/************************************** the screen
```

```
SCREEN CLEAR BOX 13 1 SCRHEIGHT SCRWIDTH FGSTANDARD BGSTANDARD
SCREEN PRINT SCRHEIGHT 2 FGSTANDARD BGSTANDARD \
    "Drug Taper  == Copyright (c) 1989 Mayo Foundation"
SCREEN SAVE 3 3 SCRHEIGHT (SCRWIDTH-3) Screen_Memory
SCREEN CLEAR BOX 3 3 (SCRHEIGHT-1) (SCRWIDTH-3) FGPLEASING BGPLEASING SCREEN PRINT 4 4 FGPLEASING BGPLEASING "Choose what to do next:"
SCREEN CLEAR BOX SCRHEIGHT-5 4 SCRHEIGHT-2 SCRWIDTH-4 BGPLEASING FGPLEASING
SCREEN PRINT SCRHEIGHT-4 6 BGPLEASING FGPLEASING\
    "Use the space bar to move between choices"
SCREEN PRINT SCRHEIGHT-3 6 BGPLEASING FGPLEASING\
    "Push RETURN when finished"
SCREEN PRINT 5 10 FGPLEASING BGPLEASING "Calculate a drug administration schedule"
SCREEN PRINT 6 10 FGPLEASING BGPLEASING "Calculate a taper for a different time duration"
SCREEN PRINT 7 10 FGPLEASING BGPLEASING "View the same taper again"
SCREEN PRINT 8 10 FGPLEASING BGPLEASING "View a taper with different starting and ending doses"
SCREEN PRINT 9 10 FGPLEASING BGPLEASING "Recalculate a taper with a different mathematical model"
SCREEN PRINT 10 10 FGPLEASING BGPLEASING "Recalculate a taper with completely new parameters"
SCREEN PRINT 11 10 FGPLEASING BGPLEASING "Graph the current taper"
SCREEN PRINT 12 10 FGPLEASING BGPLEASING "Modify an already existing taper"
SCREEN PRINT 13 10 FGPLEASING BGPLEASING "Print out the current taper"
SCREEN PRINT 14 10 FGPLEASING BGPLEASING "Print out a drug administration schedule for the current taper"
SCREEN PRINT 15 10 FGPLEASING BGPLEASING "Exit the drug taper program"

SCREEN MENU 5 4 15 9 FGSTANDARD BGSTANDARD FGINVSTANDARD BGINVSTANDARD \
1 "--->  --->  --->  --->  --->  --->  --->  --->  --->  --->  --->" $OptionChosen
SCREEN SHORTRESTORE Screen_Memory
_ProcDply("P R O C E S S I N G")
CASE ($OptionChosen)
/************************************************ Here to calculate a schedule
WHEN(1)
    LABEL SCHEDULING
        LET $TimeForDose_1 = " "
        LET $TimeForDose_2 = " "
        LET $TimeForDose_3 = " "
        LET $TimeForDose_4 = " "
        LET $TimeForDose_5 = " "
        LET $TimeForDose_6 = " "
        _Get_Info("$NrDosesPerTimeUnit",\
           FGSTANDARD,BGSTANDARD,FGINVSTANDARD,BGINVSTANDARD)
        IF ($TimeSpanForEachDose = "minute")
            Let TimeUnit = "time"
        ELSEIF ($TimeSpanForEachDose = "hour")
            Let TimeUnit = "time"
        ELSE
            Let TimeUnit = "date"
        END IF
        _Get_Info("$DateForFirstDose",\
           FGSTANDARD,BGSTANDARD,FGINVSTANDARD,BGINVSTANDARD)
        _Get_Info("$TimeForDose",\
           FGSTANDARD,BGSTANDARD,FGINVSTANDARD,BGINVSTANDARD)
/************************************************* Error Checking Routines
        LET $Error = 0
        IF ($NrDosesPerTimeUnit > 6 OR $NrDosesPerTimeUnit < 1 )
            _ERROR(10)
            JUMP SCHEDULING
        END IF
```

Page 4

```
        REPAINT
/************************************** This clears the screen bottom
        SCREEN CLEAR BOX (SCRHEIGHT-3) 1 (SCRHEIGHT) (SCRWIDTH) \
              FGSTANDARD BGSTANDARD NO-BORDER
        MESSAGE "Push any key to continue."
        JUMP CHOICES
/************************************** Here to choose a diff. time dur.
WHEN(2)
        _TEST_MODIFY()
        JUMP TIMEINTERVAL
/************************************** Here to see the same taper
WHEN( 3)
        AT r1c1
        SHEET GOTO SHEET "taperdis"
        AT r18c1
        JUMP TAPERDISPLAY
/************************************** To change start & end doses
WHEN(4)
        _TEST_MODIFY()
        _Load_Screen_I11C()
        JUMP CALCULATIONS
/************************************** Here to change math model
WHEN(5)
        _Get_Info("$MathModel",\
            FGSTANDARD,BGSTANDARD,FGINVSTANDARD,BGINVSTANDARD)
        JUMP CALCULATIONS
/************************************** Here for a totally new taper
WHEN (6)
        _TEST_MODIFY()
        JUMP BEGINNING
/************************************** Here to graph the taper
WHEN(7)
        SHEET GOTO SHEET "TaperCal"
        GRAPH GENERATE "Taper" PREVIEW
        JUMP CHOICES
/************************************** Here to modify a taper
WHEN(8)
        IF ($CreateOrModify = "CREATE")
            LET $CreateOrModify = "MODIFY"
            _ERROR(5)
        END IF
        LET $DurationToPlot = 98
        JUMP BEGINNING
/************************************** Here to print the taper
WHEN(9)
        AT R1C1
        SHEET GOTO SHEET "TaperCal"
        PRINT REPORT EXECUTE "TAPER.RDF" PRINTER COPIES 1
        JUMP CHOICES
/************************************** Here to print a schedule
WHEN(10)
        AT R1C1
        SHEET GOTO SHEET "SchedDis"
        FOR RowNumber = 3 to 150
            IF CellText (MakeCell(RowNumber,1)) = ""
                Jump Print_Spot
            End If
        End For
        Label Print Spot
```

```
'************************************* Reset the AutoHelp Flag
         IF (Auto_Help_Status)
              AutoHelp On
         End If
'************************************* Return to module from which
'************************************* the program was entered
         CASE (QUIT_FLAG)
'************************************* Here if entered from DOS
              WHEN 0
                  FILE UNLOAD "All"
                  QUIT QUIT
'************************************* Here if entered from main menu
              WHEN 1
                  FILE UNLOAD "All"
                  QUIT MAIN-MENU
'************************************* Here if entered from spreadsheet
              WHEN 2
                  FILE UNLOAD "All"
                  EXIT MAIN
'************************************* Here for debugging purposes
'************************************* Exit without unloading files
              WHEN 3
                  EXIT MAIN
              END CASE
END CASE
'************************************* Here if unacceptable choice
' Here if an unacceptable choice occurs.  This should not happen
' as the choices are made from a menu.
 _ERROR(3)
JUMP CHOICES '*********************************************************************
' Execution Blocks                                                    *
'                                                                     *
'*********************************************************************
'************************************* Here to modify an existing taper
LABEL MODIFY
LET $DurationToPlot = 98
_Get_Info("$FirstDayTotalDose",\
    FGSTANDARD,BGSTANDARD,FGINVSTANDARD,BGINVSTANDARD)
_Get_Info("$DurationToPlot",\
    FGSTANDARD,BGSTANDARD,FGINVSTANDARD,BGINVSTANDARD)
Let ModifyDur = $DurationToPlot
_Get_Info("$LastDayTotalDose",\
    FGSTANDARD,BGSTANDARD,FGINVSTANDARD,BGINVSTANDARD)
'************************************* Here change text to numeric var.
$FirstDayTotalDose = VALUE($FirstDayTotalDose)
$DurationToPlot = VALUE($DurationToPlot)
$LastDayTotalDose = VALUE($LastDayTotalDose)

'************************************* Here to check for errors
LET $Error = 0
IF ($LastDayTotalDose >= $FirstDayTotalDose)
    LET $Error = 9
END IF
IF (($FirstDayTotalDose <= 0) OR ($LastDayTotalDose <= 0))
    LET $Error =7
END IF
IF ( (NOT (ISNUMBER ($DurationToPlot))) OR (NOT (ISNUMBER ($FirstDayTotalDose))) OR (NOT (ISNUMBER ($LastDayTotalDose))))
    LET $Error = 2
END IF
IF ($Error)
    _Error($Error)
    JUMP MODIFY
    END IF
_Check_Duration()
IF ($Error )
    JUMP MODIFY
END IF
JUMP CALCULATIONS
END MAIN '*********************************************************************
' Here Begin The Procedures                                           *
```

```
'
'*****************************************************
'*****************************************************
' Functions                                           *
'
'*****************************************************
'*****************************************************

'*****************************************************
' Error Function -- This function generates error messages  *
'
'*****************************************************
FUNCTION _ERROR($Error)
LOCAL Screen_Memory
SCREEN SAVE 5 10 15 70 Screen_Memory
SCREEN.CLEAR BOX 5 10 15 70 FGERROR BGERROR
'*********************************** Sound codes:
' 440 Hz -- re-enter date
' 660 Hz -- internal system error
' 880 Hz -- No action required, info only CASE ($Error)
   WHEN ( 1)
      SOUND 440 .75
      SCREEN PRINT 9 11 FGERROR BGERROR FORMAT "H59" "Drug Taper Error (1)"
      SCREEN PRINT 10 11 FGERROR BGERROR FORMAT "H59" "Cannot have more than 98 days."
      SCREEN PRINT 11 11 FGERROR BGERROR FORMAT "H59" "Re-enter data."
   WHEN ( 2)
      SOUND 440 .75
      SCREEN PRINT 9 11 FGERROR BGERROR FORMAT "H59" "Drug Taper Error (2)"
      SCREEN PRINT 10 11 FGERROR BGERROR FORMAT "H59" "Numeric data must only be numeric. Do not include units."
      SCREEN PRINT 11 11 FGERROR BGERROR FORMAT "H59" "For example, enter 25 milligrams as ""25"" "
      SCREEN PRINT 12 11 FGERROR BGERROR FORMAT "H59" "or ""25.0"", NOT ""25mg"""
      SCREEN PRINT 13 11 FGERROR BGERROR FORMAT "H59" "Re-enter data."
   WHEN ( 3)
      SOUND 660 .25
      SCREEN PRINT 9 11 FGERROR BGERROR FORMAT "H59" "Drug Taper Error (3)"
      SCREEN PRINT 10 11 FGERROR BGERROR FORMAT "H59" "Internal Error."
      SCREEN PRINT 11 11 FGERROR BGERROR FORMAT "H59" "You have selected an option not yet programmed."
      SCREEN PRINT 12 11 FGERROR BGERROR FORMAT "H59" "Re-enter data."
   WHEN ( 4)
      SOUND 880 .25
      SCREEN PRINT 9 11 FGERROR BGERROR FORMAT "H59" "System Message (4)"
      SCREEN PRINT 10 11 FGERROR BGERROR FORMAT "H59" "You previously were modifying a pre-existing taper."
      SCREEN PRINT 11 11 FGERROR BGERROR FORMAT "H59" "The program will now assume"
      SCREEN PRINT 12 11 FGERROR BGERROR FORMAT "H59" "you are creating a new taper."
   WHEN ( 5)
      SOUND 880 .25
      SCREEN PRINT 9 11 FGERROR BGERROR FORMAT "H59" "System Message (5)"
      SCREEN PRINT 10 11 FGERROR BGERROR FORMAT "H59" "You were previously creating a new taper."
      SCREEN PRINT 11 11 FGERROR BGERROR FORMAT "H59" "The program will now assume you are"
      SCREEN PRINT 12 11 FGERROR BGERROR FORMAT "H59" "modifying a pre-existing taper."
   WHEN ( 6)
      SOUND 440 .75
      SCREEN PRINT 9 11 FGERROR BGERROR FORMAT "H59" "Drug Taper Error (6)"
      SCREEN PRINT 10 11 FGERROR BGERROR FORMAT "H59" "Cannot have time period greater than 105" & $TimeSpanForEachDose
      SCREEN PRINT 11 11 FGERROR BGERROR FORMAT "H59" "Re-enter data."
   WHEN ( 7)
      SOUND 440 .75
      SCREEN PRINT 9 11 FGERROR BGERROR FORMAT "H59" "Drug Taper Error (7)"
      SCREEN PRINT 10 11 FGERROR BGERROR FORMAT "H59" "Negative or zero values unacceptable."
      SCREEN PRINT 11 11 FGERROR BGERROR FORMAT "H59" "Re-enter data."
   WHEN ( 8)
      SOUND 440 .75
      SCREEN PRINT 9 11 FGERROR BGERROR FORMAT "H59" "Drug Taper Error (8)"
      SCREEN PRINT 10 11 FGERROR BGERROR FORMAT "H59" "Duration must be of at least 2" & $TimeSpanForEachDose | "s."
      SCREEN PRINT 11 11 FGERROR BGERROR FORMAT "H59" "Re-enter data."
   WHEN ( 9)
      SOUND 440 .75
      SCREEN PRINT 9 11 FGERROR BGERROR FORMAT "H59" "Drug Taper Error (9)"
      SCREEN PRINT 10 11 FGERROR BGERROR FORMAT "H59" "Final dose must be less than initial dose."
      SCREEN PRINT 11 11 FGERROR BGERROR FORMAT "H59" "Re-enter data."
   WHEN ( 10)
      SOUND 440 .75
```

```
/*******************************************************************
' Function Check Duration -- This function checks that the length of  *
' the taper is valid                                                   *
/*******************************************************************
FUNCTION _Check_Duration()
LET $Error = 0
IF ($DurationToPlot >105)
        LET $Error = 6
END IF
IF (($DurationToPlot > 98) AND ($TimeSpanForEachDose=="DAY"))
        LET $Error = 1
END IF
IF ($DurationToPlot < 2)
        LET $Error = 8
END IF
IF ($Error)
        _ERROR($Error)
END IF
RETURN
END FUNCTION /*******************************************************************
' Test/Modify Function -- This function checks if you are automatically *
' changing from CREATE to MODIFY or otherwise                          *
/*******************************************************************
FUNCTION _TEST_MODIFY()
IF ($CreateOrModify == "MODIFY")
        LET $CreateOrModify = "CREATE"
        _ERROR(4)
END IF
RETURN
END FUNCTION /*******************************************************************
' ProcDply Function -- This function generates the screen that is displayed*
' when the program is processing or otherwise                          *
/*******************************************************************
FUNCTION _ProcDply(X)
/*********************************** Clear the screen
SCREEN CLEAR FGBACKGROUND BGBACKGROUND
/*********************************** Draw the technical info
_DRAW_SKED_INFO($HrDosesPerTimeUnit,$DateForFirstDose,FGSTANDARD,BGSTANDARD)
_DRAW_DRUG_INFO($DrugName,MinDoseSize,FGSTANDARD,BGSTANDARD)
_DRAW_TECH_INFO($MathModel,$CreateOrModify,$TimeSpanForEachDose,FGSTANDARD,BGSTANDARD)
_DRAW_TAPER_INFO($FirstDayTotalDose,$LastDayTotalDose,$DurationToPlot,FGSTANDARD,BGSTANDARD)
/*********************************** Draw the bottom data box
SCREEN CLEAR BOX 13 1 SCRHEIGHT SCRWIDTH FGSTANDARD BGSTANDARD
SCREEN PRINT SCRHEIGHT 2 FGSTANDARD BGSTANDARD \
        "Drug Taper     Copyright   1989 Mayo Foundation"
/*********************************** Draw the word line in the data box
SCREEN PRINT 16 2 FGINVSTANDARD BGINVSTANDARD FORMAT "H78" X
SCREEN PRINT 15 2 FGINVSTANDARD BGINVSTANDARD FORMAT "H78" " "
SCREEN PRINT 17 2 FGINVSTANDARD BGINVSTANDARD FORMAT "H78" " "
RETURN
END FUNCTION /*******************************************************************
' Draw_Sked_Info Function -- This function generates part of the baseline *
' information screen.                                                  *
/*******************************************************************
FUNCTION _DRAW_SKED_INFO($HrDosesPerTimeUnit,$DateForFirstDose,COLOR1,COLOR2)
SCREEN CLEAR BOX 7 (SCRWIDTH/2 + 1) 12 SCRWIDTH COLOR1 COLOR2
SCREEN PRINT 7 (SCRWIDTH/2 + 3) COLOR1 COLOR2 "Scheduling Information"
SCREEN PRINT 8 (SCRWIDTH/2 + 5) COLOR1 COLOR2 \
        "Doses/" | $TimeSpanForEachDose | ":"
SCREEN PRINT 8 (SCRCOLUMN +1) COLOR1 COLOR2 $HrDosesPerTimeUnit
SCREEN PRINT 9 (SCRWIDTH/2 + 5) COLOR1 COLOR2 \
        "Schedule starts at:" & $DateForFirstDose
RETURN
END FUNCTION

/*******************************************************************
```

```
' Draw_Drug_Info Function -- This function generates part of the baseline  *
' information screen.                                                       *
'***************************************************************************
FUNCTION _DRAW_DRUG_INFO($DrugName,MinDoseSize,COLOR1,COLOR2)
SCREEN CLEAR BOX 1 1 6 (SCRWIDTH/2) COLOR1 COLOR2
SCREEN PRINT 1 3 COLOR1 COLOR2 "Drug Information"
SCREEN PRINT 2 5 COLOR1 COLOR2 "Drug Name:" & $DrugName
SCREEN PRINT 3 5 COLOR1 COLOR2 "Minimum Drug Size:"& MinDoseSize
RETURN
END FUNCTION '***************************************************************************
' Draw_Tech_Info Function -- This function generates part of the baseline  *
' information screen.                                                       *
'***************************************************************************
FUNCTION _DRAW_TECH_INFO($MathModel,$CreateOrModify,$TimeSpanForEachDose,COLOR1,COLOR2)
SCREEN CLEAR BOX 1 (SCRWIDTH/2 +1) 6 SCRWIDTH COLOR1 COLOR2
SCREEN PRINT 1 (SCRWIDTH/2 + 3) COLOR1 COLOR2 "Technical Information"
SCREEN PRINT 2 (SCRWIDTH/2 + 5) COLOR1 COLOR2 "Mathematical Model:" & $MathModel
IF ($CreateOrModify == "CREATE")
     SCREEN PRINT 3 (SCRWIDTH/2 + 5) COLOR1 COLOR2\
         "CREATE a new taper."
   ELSE
     SCREEN PRINT 3 (SCRWIDTH/2 + 5) COLOR1 COLOR2\
         "MODIFY an already existing taper."
   END IF
SCREEN PRINT 4 (SCRWIDTH/2 + 5) COLOR1 COLOR2\
     "Doses given in total per" & $TimeSpanForEachDose
RETURN
END FUNCTION '***************************************************************************
' Draw_Taper_Info Function -- This function generates part of the baseline *
' information screen.                                                       *
'***************************************************************************
FUNCTION _DRAW_TAPER_INFO($FirstDayTotalDose,$LastDayTotalDose,$DurationToPlot,COLOR1,COLOR2)
SCREEN CLEAR BOX 7 1 12 (SCRWIDTH/2) COLOR1 COLOR2
SCREEN PRINT 7 3 COLOR1 COLOR2 "Taper Information"
SCREEN PRINT 8 5 COLOR1 COLOR2 "Initial dose:"
SCREEN PRINT 8 (SCRCOLUMN+1) COLOR1 COLOR2 $FirstDayTotalDose
'******************************************* Display varies for CREATE/MODIFY
IF ($CreateOrModify == "CREATE")\
   SCREEN PRINT 9 5 COLOR1 COLOR2\
       "Dose for last" & $TimeSpanForEachDose | ":"
   SCREEN PRINT 9 (SCRCOLUMN+1) COLOR1 COLOR2 $LastDayTotalDose
   SCREEN PRINT 10 5 COLOR1 COLOR2\
       "Duration:"
   SCREEN PRINT 10 (SCRCOLUMN+1) COLOR1 COLOR2 $DurationToPlot
   SCREEN PRINT 10 (SCRCOLUMN+1) COLOR1 COLOR2 ($TimeSpanForEachDose|"s")
ELSE
'******************************************* Choose suffix for 1st, 2d, etc.
   CASE (RIGHT(ModifyDur,1))
        WHEN ("1")
           SCREEN PRINT 9 5 COLOR1 COLOR2\
               "Dose for"
           SCREEN PRINT 9 (SCRCOLUMN+1) COLOR1 COLOR2 $DurationToPlot
           SCREEN PRINT 9 (SCRCOLUMN) COLOR1 COLOR2 ("st" & $TimeSpanForEachDose | ":")
           SCREEN PRINT 9 (SCRCOLUMN+1) COLOR1 COLOR2 $LastDayTotalDose
        WHEN ("2")
           SCREEN PRINT 9 5 COLOR1 COLOR2\
               "Dose for"
           SCREEN PRINT 9 (SCRCOLUMN+1) COLOR1 COLOR2 $DurationToPlot
           SCREEN PRINT 9 (SCRCOLUMN) COLOR1 COLOR2 ("nd" & $TimeSpanForEachDose | ":")
           SCREEN PRINT 9 (SCRCOLUMN+1) COLOR1 COLOR2 $LastDayTotalDose
        WHEN("3")
           SCREEN PRINT 9 5 COLOR1 COLOR2\
               "Dose for"
           SCREEN PRINT 9 (SCRCOLUMN+1) COLOR1 COLOR2 $DurationToPlot
           SCREEN PRINT 9 (SCRCOLUMN) COLOR1 COLOR2 ("rd" & $TimeSpanForEachDose | ":")
           SCREEN PRINT 9 (SCRCOLUMN+1) COLOR1 COLOR2 $LastDayTotalDose
        OTHERWISE
           SCREEN PRINT 9 5 COLOR1 COLOR2\
               "Dose for"
           SCREEN PRINT 9 (SCRCOLUMN+1) COLOR1 COLOR2 $DurationToPlot
```

```
                SCREEN PRINT 9 (SCRCOLUMN) COLOR1 COLOR2 ("th" & $TimeSpanForEachDose | ":")
                SCREEN PRINT 9 (SCRCOLUMN+1) COLOR1 COLOR2 $LastDayTotalDose
        END CASE
END IF
RETURN
END FUNCTION '*********************************************************************
' Get_Info Function -- This function is what asks for most info in the   *
' program.                                                               *
'*********************************************************************
FUNCTION _GET_INFO(Variable,Color1,Color2,Color3,Color4)
'This function will get information for Variable and put the result
' in a global value. Color1 and Color2 are foreground and background colors
' for the variables NOT being asked. Color3 and Color4 are for the
' group of variables being asked.
LOCAL X
'*********************************** Draw all the boxes
_DRAW_SKED_INFO($HrDosesPerTimeUnit,$DateForFirstDose,Color1,Color2)
_DRAW_DRUG_INFO($DrugName,MinDoseSize,Color1,Color2)
_DRAW_TECH_INFO($MathModel,$CreateOrModify,$TimeSpanForEachDose,Color1,Color2)
_DRAW_TAPER_INFO($FirstDayTotalDose,$LastDayTotalDose,$DurationToPlot,\
        Color1,Color2)
SCREEN CLEAR BOX 13 1 SCRHEIGHT SCRWIDTH Color1 Color2
SCREEN PRINT SCRHEIGHT 2 Color1 Color2 \
        "Drug Taper     Copyright    1989 Mayo Foundation"

'*********************************** Highlight the asked-about box
CASE (Variable)
    WHEN ("$HrDosesPerTimeUnit")
        _DRAW_SKED_INFO($HrDosesPerTimeUnit,$DateForFirstDose,Color3,Color4)
    WHEN ("$DateForFirstDose")
        _DRAW_SKED_INFO($HrDosesPerTimeUnit,$DateForFirstDose,Color3,Color4)
    WHEN ("$DrugName")
        _DRAW_DRUG_INFO($DrugName,MinDoseSize,Color3,Color4)
    WHEN ("$MinDoseSizeAvail")
        _DRAW_DRUG_INFO($DrugName,MinDoseSize,Color3,Color4)
    WHEN ("$MathModel")
        _DRAW_TECH_INFO($MathModel,$CreateOrModify,$TimeSpanForEachDose,\
            Color3,Color4)
    WHEN ("$CreateOrModify")
        _DRAW_TECH_INFO($MathModel,$CreateOrModify,$TimeSpanForEachDose,\
            Color3,Color4)
    WHEN ("$TimeSpanForEachDose")
        _DRAW_TECH_INFO($MathModel,$CreateOrModify,$TimeSpanForEachDose,\
            Color3,Color4)
    WHEN ("$FirstDayTotalDose")
        _DRAW_TAPER_INFO($FirstDayTotalDose,$LastDayTotalDose,$DurationToPlot,\
            Color3,Color4)
    WHEN ("$LastDayTotalDose")
        _DRAW_TAPER_INFO($FirstDayTotalDose,$LastDayTotalDose,$DurationToPlot,\
            Color3,Color4)
    WHEN ("$DurationToPlot")
        _DRAW_TAPER_INFO($FirstDayTotalDose,$LastDayTotalDose,$DurationToPlot,\
            Color3,Color4)
    WHEN ("$TimeForDose")
        _DRAW_TAPER_INFO($FirstDayTotalDose,$LastDayTotalDose,$DurationToPlot,\
            Color3,Color4)
    OTHERWISE
        _ERROR(12)
END CASE '*********************************** Get the information
CASE(Variable)
    WHEN ("$HrDosesPerTimeUnit")
        SCREEN PRINT 15 2 Color1 Color2\
            "How many doses do you want to give for each "\
            |$TimeSpanForEachDose|"?"
        SCREEN INPUT 15 55 Color3 Color4 1 X MASK "[1-6]"
        LET $HrDosesPerTimeUnit = VALUE(X)
    WHEN ("$DateForFirstDose")
        SCREEN PRINT 15 2 Color1 Color2 \
            "What is the "| TimeUnit |" for the first dose?"
'*********************************** Box to show how to enter dates
```

```
        IF TimeUnit = "date"
           LABEL DATE_AGAIN
           SCREEN SAVE 16 5 (SCRHEIGHT-1) (SCRWIDTH-5) Screen_Memory
           SCREEN CLEAR BOX 16 5 (SCRHEIGHT-1) (SCRWIDTH-5) Color1 Color2
           SCREEN PRINT 17 6 Color1 Color2 FORMAT "H65"\
                  "Dates must be in one of two formats:"
           SCREEN PRINT 18 6 Color1 Color2 FORMAT "H65"\
                  """Jan 29, 1959""" or """1/29/59"""
           SCREEN INPUT 15 40 Color1 Color2 15 $DateForFirstDose
           SCREEN SHORTRESTORE Screen_Memory
                  IF (NOT (ISDATE($DateForFirstDose)))
                      _Error(11)
                      Jump DATE_AGAIN
                  END IF
/****************************************** Box to show how to enter times
        ELSE
           SCREEN SAVE 16 5 (SCRHEIGHT-1) (SCRWIDTH-5) Screen_Memory
           SCREEN CLEAR BOX 16 5 (SCRHEIGHT-1) (SCRWIDTH-5) Color1 Color2
           SCREEN PRINT 17 6 Color1 Color2 FORMAT "H65"\
                 "Times may be listed in either 12 or 24 hour format"
           SCREEN PRINT 18 6 Color1 Color2 FORMAT "H65"\
                 "For example, ""12:23"", ""12:23am"", ""00:23"""
           SCREEN INPUT 15 40 Color3 Color4 7 $DateForFirstDose \
                 MASK "[0-9]*2[0-9\:][0-9]([0-9\A\P\a\p])([I\A\P\H\a\p\m])([\H\m])"
           SCREEN SHORTRESTORE Screen_Memory
        END IF
     WHEN ("$DrugName")
        SCREEN PRINT 15 2 Color1 Color2\
           "What is the name of the drug:"
        SCREEN INPUT 15 32 Color3 Color4 15 $DrugName
     WHEN ("$MinDoseSizeAvail")
        SCREEN PRINT 15 2 Color1 Color2 \
           "What is the minimum dose size available for "|$DrugName|"?"
        SCREEN INPUT 15 62 Color3 Color4 5 MinDoseSize MASK\
           "[0-9\.][0-9\.\ ]*3[0-9\ ]"
        LET $MinDoseSizeAvail = VALUE(MinDoseSize)
     WHEN ("$MathModel")
        SCREEN PRINT 15 2 Color1 Color2 \
           "Which mathematical model do you want to use?"
/****************************************** Box to describes math models
        SCREEN SAVE 18 5 (SCRHEIGHT-1) (SCRWIDTH-5) Screen_Memory
        SCREEN CLEAR BOX 18 5 (SCRHEIGHT-1) (SCRWIDTH-5) Color1 Color2
        SCREEN PRINT 19 6 Color1 Color2 FORMAT "H65"\
           "Model 1 is an exact calculation"
        SCREEN PRINT 20 6 Color1 Color2 FORMAT "H65"\
           "Model 2 keeps track of rounding errors"
        SCREEN PRINT 21 6 Color1 Color2 FORMAT "H65"\
           "Model 3 is the same as Model 2, but forces a continual decrease"
        SCREEN MENU 16 2 16 79 Color1 Color2 \
           Color3 Color4 1 "Model_1 Model_2 Model_3" $MathModel
        $MathModel = GROUP("Model_1 Model_2 Model_3",$MathModel)
        SCREEN SHORTRESTORE Screen_Memory
     WHEN ("$CreateOrModify")
        SCREEN PROMPT 15 2 20 79 Color3 Color4 "CREATE MODIFY" \
           $CreateOrModify \
           "Do you want to create a new taper or modify an old one?"
        $CreateOrModify = GROUP("CREATE MODIFY",$CreateOrModify)
     WHEN ("$TimeSpanForEachDose")
        SCREEN PROMPT 15 2 20 79 Color3 Color4 \
           "Minute Hour Day Week Month" $TimeSpanForEachDose \
           "For what time duration do you want to calculate the taper?"
        $TimeSpanForEachDose = GROUP("minute hour day week month",\
           $TimeSpanForEachDose)
     WHEN ("$FirstDayTotalDose")
        SCREEN PRINT 15 2 Color1 Color2\
           "What is the total dose for the first "|$TimeSpanForEachDose|"?"
        SCREEN INPUT 15 50 Color3 Color4 15 $FirstDayTotalDose \
           MASK "[0-9\.][0-9\.\ ]*13[0-9\ ]"
        LET $FirstDayTotalDose = VALUE($FirstDayTotalDose)
     WHEN ("$LastDayTotalDose")
        SCREEN PRINT 15 2 Color1 Color2\
           "What is the total dose for the last "|$TimeSpanForEachDose|"?"
        SCREEN INPUT 15 50 Color3 Color4 15 $LastDayTotalDose \
           MASK "[0-9\.]*14[0-9\ \.]"
```

```
    LET $LastDayTotalDose = VALUE($LastDayTotalDose)
  WHEN ("$DurationToPlot")
    IF ($CreateOrModify = "MODIFY")
        SCREEN PRINT 15 2 Color1 Color2 \
            "What was the last" & $TimeSpanForEachDose & "for which you have dosing information?"
        SCREEN INPUT 15 68 Color3 Color4 3 $DurationToPlot \
            MASK "[1-9]*2[0-9/ ]"
        Let ModifyDur = $DurationToPlot
    ELSE
        SCREEN PRINT 15 2 Color1 Color2\
            "For how many "|$TimeSpanForEachDose|"s should the taper be calculated?"
        SCREEN INPUT 15 55 Color3 Color4 3 $DurationToPlot \
            MASK "[1-9]*3[0-9\ ]"
    END IF
  WHEN ("$TimeForDose")
/************************************ Print out the right # of requests
    SCREEN PRINT 15 2 Color1 Color2 \
        "What is the time for the first dose in each "| $TimeSpanForEachDose |"?"
    If ($NrDosesPerTimeUnit > 1)
        SCREEN PRINT 16 2 Color1 Color2 \
            "What is the time for the second dose in each "| $TimeSpanForEachDose |"?"
    End If
    If ($NrDosesPerTimeUnit > 2)
        SCREEN PRINT 17 2 Color1 Color2 \
            "What is the time for the third dose in each "| $TimeSpanForEachDose |"?"
    End If
    If ($NrDosesPerTimeUnit > 3)
        SCREEN PRINT 18 2 Color1 Color2 \
            "What is the time for the fourth dose in each "| $TimeSpanForEachDose |"?"
    End If
    If ($NrDosesPerTimeUnit > 4)
        SCREEN PRINT 19 2 Color1 Color2 \
            "What is the time for the fifth dose in each "| $TimeSpanForEachDose |"?"
    End If
    If ($NrDosesPerTimeUnit > 5)
        SCREEN PRINT 20 2 Color1 Color2 \
            "What is the time for the sixth dose in each "| $TimeSpanForEachDose |"?"
    End If /************************************ Get the right number of inputs
    SCREEN INPUT 15 55 Color3 Color4 15 $TimeForDose_1
    If ($NrDosesPerTimeUnit > 1)
        SCREEN INPUT 16 55 Color3 Color4 15 $TimeForDose_2
    End If
    If ($NrDosesPerTimeUnit > 2)
        SCREEN INPUT 17 55 Color3 Color4 15 $TimeForDose_3
    End If
    If ($NrDosesPerTimeUnit > 3)
        SCREEN INPUT 18 55 Color3 Color4 15 $TimeForDose_4
    End If
    If ($NrDosesPerTimeUnit > 4)
        SCREEN INPUT 19 55 Color3 Color4 15 $TimeForDose_5
    End If
    If ($NrDosesPerTimeUnit > 5)
        SCREEN INPUT 20 55 Color3 Color4 15 $TimeForDose_6
    End If END CASE
/************************************ Reset the asked-about box
SCREEN CLEAR BOX 13 1 SCRHEIGHT SCRWIDTH Color1 Color2
SCREEN PRINT SCRHEIGHT 2 Color1 Color2 \
    "Drug Taper    Copyright  1989 Mayo Foundation"
/************************************ Reset highlighted box to plain
CASE (Variable)
  WHEN ("$NrDosesPerTimeUnit")
      _DRAW_SKED_INFO($NrDosesPerTimeUnit,$DateForFirstDose,Color1,Color2)
  WHEN ("$DateForFirstDose")
      _DRAW_SKED_INFO($NrDosesPerTimeUnit,$DateForFirstDose,Color1,Color2)
  WHEN ("$DrugName")
      _DRAW_DRUG_INFO($DrugName,MinDoseSize,Color1,Color2)
  WHEN ("$MinDoseSizeAvail")
      _DRAW_DRUG_INFO($DrugName,MinDoseSize,Color1,Color2)
  WHEN ("$MathModel")
      _DRAW_TECH_INFO($MathModel,$CreateOrModify,$TimeSpanForEachDose,\
```

```
FORMULAS FOR WORKSHEET TAPERCAL

ROW  COL   FORMULA 1    1    exp ((ln ($lastdaytotaldose/$firstdaytotaldose))/$durationtoplot)
      2    $firstdaytotaldose
      3    r1c2
      4    if (row <= $durationtoplot)
                then ((round (r1c3 / $mindosesizeavail, 0)) * $mindosesizeavail)
                else " "
      5    r1c4
      6    row
 2    2    @if(($createormodify == "CREATE"),
                (if (row <= $durationtoplot)
                    then ($firstdaytotaldose * (k ^ row))
                    else " "),
                (if (($firstdaytotaldose * (k ^ row)) >= 0.001)
                    then ($firstdaytotaldose * (k ^ row))
                    else " "))
      3    @if(($createormodify == "CREATE"),
                (if (row <= $durationtoplot)
                    then (r1c3 + r2c2)
                    else " "),
                (if r2c2 > 0
                    then (r1c3 + r2c2)
                    else " "))
      4    if ( ($createormodify == "CREATE") and (row <= $durationtoplot)) then
                choose( (val(right($mathmodel,1))),
                " ",
                (round((r2c2/$mindosesizeavail),0)*$mindosesizeavail),
                (round(((r2c3-r1c5)/$mindosesizeavail),0)*$mindosesizeavail),
                (min((r1c4),(round(((r2c3-r1c5)/$mindosesizeavail),0)*$mindosesizeavail)))
                )
                else
                if ( ($createormodify == "MODIFY") and
                    ((r1c4 > 0) or ($mathmodel=="Model_2")) ) then
                    choose( (val(right($mathmodel,1))),
                    " ",
                    (round((r2c2/$mindosesizeavail),0)*$mindosesizeavail),
                    (if ((round(((r2c3-r1c5)/$mindosesizeavail),0)*$mindosesizeavail)> 0) then
                        (round(((r2c3-r1c5)/$mindosesizeavail),0)*$mindosesizeavail)
                        else " "),
                    (min((r1c4),(round(((r2c3-r1c5)/$mindosesizeavail),0)*$mindosesizeavail)))
                    )
                else
                " "
      5    if( (($createormodify == "CREATE") and (row <= $durationtoplot)) or
                (($createormodify == "MODIFY") and (r2c2 >= 0.001)))
                then
                r1c5+r2c4 else " "
      6    if( (($createormodify == "CREATE") and (row <= $durationtoplot)) or
                (($createormodify == "MODIFY") and (r2c2 >= 0.001)))
                then
                row else " "
 3    2    @if(($createormodify == "CREATE"),
                (if (row <= $durationtoplot)
                    then ($firstdaytotaldose * (k ^ row))
                    else " "),
                (if (($firstdaytotaldose * (k ^ row)) >= 0.001)
                    then ($firstdaytotaldose * (k ^ row))
                    else " "))
      3    @if(($createormodify == "CREATE"),
                (if (row <= $durationtoplot)
                    then (r2c3 + r3c2)
                    else " "),
                (if r3c2 > 0
                    then (r2c3 + r3c2)
                    else " "))
      4    if ( ($createormodify == "CREATE") and (row <= $durationtoplot)) then
                choose( (val(right($mathmodel,1))),
                " ",
                (round((r3c2/$mindosesizeavail),0)*$mindosesizeavail),
                (round(((r3c3-r2c5)/$mindosesizeavail),0)*$mindosesizeavail),
```

FORMULAS FOR WORKSHEET TAPERCAL

ROW  COL  FORMULA

```
              (if (($firstdaytotaldose * (k ^ row)) >= 0.001)
                  then ($firstdaytotaldose * (k ^ row))
                  else " "))
     3    @if(($createormodify == "CREATE"),
              (if (row <= $durationtoplot)
                  then (r4c3 + r5c2)
                  else " "),
              (if r5c2 > 0
                  then (r4c3 + r5c2)
                  else " "))
     4    if ( ($createormodify == "CREATE") and (row <= $durationtoplot)) then
              choose( (val(right($mathmodel,1))),
              "",
              (round((r5c2/$mindosesizeavail),0)*$mindosesizeavail),
              (round(((r5c3-r4c5)/$mindosesizeavail),0)*$mindosesizeavail),
              (min((r4c4),(round(((r5c3-r4c5)/$mindosesizeavail),0)*$mindosesizeavail)))
              )
              else
              if ( ($createormodify == "MODIFY") and
                  ((r4c4 > 0) or ($mathmodel=="Model_2")) ) then
                  choose( (val(right($mathmodel,1))),
                  " ",
                  (round((r5c2/$mindosesizeavail),0)*$mindosesizeavail),
                  (if ((round(((r5c3-r4c5)/$mindosesizeavail),0)*$mindosesizeavail)> 0) then
                      (round(((r5c3-r4c5)/$mindosesizeavail),0)*$mindosesizeavail)
                      else " "),
                  (min((r4c4),(round(((r5c3-r4c5)/$mindosesizeavail),0)*$mindosesizeavail)))
                  )
                  else
                  " "
     5    if( (($createormodify == "CREATE") and (row <= $durationtoplot)) or
              (($createormodify == "MODIFY") and (r5c2 >= 0.001)))
              then
              r4c5+r5c4 else " "
     6    if( (($createormodify == "CREATE") and (row <= $durationtoplot)) or
              (($createormodify == "MODIFY") and (r5c2 >= 0.001)))
              then
              row else " "
6    2    @if(($createormodify == "CREATE"),
              (if (row <= $durationtoplot)
                  then ($firstdaytotaldose * (k ^ row))
                  else " "),
              (if (($firstdaytotaldose * (k ^ row)) >= 0.001)
                  then ($firstdaytotaldose * (k ^ row))
                  else " "))
     3    @if(($createormodify == "CREATE"),
              (if (row <= $durationtoplot)
                  then (r5c3 + r6c2)
                  else " "),
              (if r6c2 > 0
                  then (r5c3 + r6c2)
                  else " "))
     4    if ( ($createormodify == "CREATE") and (row <= $durationtoplot)) then
              choose( (val(right($mathmodel,1))),
              "",
              (round((r6c2/$mindosesizeavail),0)*$mindosesizeavail),
              (round(((r6c3-r5c5)/$mindosesizeavail),0)*$mindosesizeavail),
              (min((r5c4),(round(((r6c3-r5c5)/$mindosesizeavail),0)*$mindosesizeavail)))
              )
              else
              if ( ($createormodify == "MODIFY") and
                  ((r5c4 > 0) or ($mathmodel=="Model_2")) ) then
                  choose( (val(right($mathmodel,1))),
                  " ",
                  (round((r6c2/$mindosesizeavail),0)*$mindosesizeavail),
                  (if ((round(((r6c3-r5c5)/$mindosesizeavail),0)*$mindosesizeavail)> 0) then
                      (round(((r6c3-r5c5)/$mindosesizeavail),0)*$mindosesizeavail)
                      else " "),
                  (min((r5c4),(round(((r6c3-r5c5)/$mindosesizeavail),0)*$mindosesizeavail)))
```

FORMULAS FOR WORKSHEET TAPERCAL

ROW  COL  FORMULA

```
                )
             else
                " "
     5    if( (($createormodify == "CREATE") and (row <= $durationtoplot)) or
             ($createormodify == "MODIFY") and (r6c2 >= 0.001))
          then
             r5c5+r6c4 else " "
     6    if( (($createormodify == "CREATE") and (row <= $durationtoplot)) or
             (($createormodify == "MODIFY") and (r6c2 >= 0.001)))
          then
             row else " "
7    2    @if(($createormodify == "CREATE"),
             (if (row <= $durationtoplot)
                then ($firstdaytotaldose * (k ^ row))
                else " "),
             (if (($firstdaytotaldose * (k ^ row)) >= 0.001)
                then ($firstdaytotaldose * (k ^ row))
                else " "))
     3    @if(($createormodify == "CREATE"),
             (if (row <= $durationtoplot)
                then (r6c3 + r7c2)
                else " "),
             (if r7c2 > 0
                then (r6c3 + r7c2)
                else " "))
     4    if ( ($createormodify == "CREATE") and (row <= $durationtoplot)) then
             choose( (val(right($mathmodel,1))),
                "",
                (round((r7c2/$mindosesizeavail),0)*$mindosesizeavail),
                (round(((r7c3-r6c5)/$mindosesizeavail),0)*$mindosesizeavail),
                (min((r6c4),(round(((r7c3-r6c5)/$mindosesizeavail),0)*$mindosesizeavail)))
             )
          else
             if ( ($createormodify == "MODIFY") and
                ((r6c4 > 0) or ($mathmodel=="Model_2")) ) then
                choose( (val(right($mathmodel,1))),
                   " ",
                   (round((r7c2/$mindosesizeavail),0)*$mindosesizeavail),
                   (if ((round(((r7c3-r6c5)/$mindosesizeavail),0)*$mindosesizeavail)> 0) then
                      (round(((r7c3-r6c5)/$mindosesizeavail),0)*$mindosesizeavail)
                      else " "),
                   (min((r6c4),(round(((r7c3-r6c5)/$mindosesizeavail),0)*$mindosesizeavail)))
                )
             else
                " "
     5    if( (($createormodify == "CREATE") and (row <= $durationtoplot)) or
             ($createormodify == "MODIFY") and (r7c2 >= 0.001))
          then
             r6c5+r7c4 else " "
     6    if( (($createormodify == "CREATE") and (row <= $durationtoplot)) or
             (($createormodify == "MODIFY") and (r7c2 >= 0.001)))
          then
             row else " "
8    2    @if(($createormodify == "CREATE"),
             (if (row <= $durationtoplot)
                then ($firstdaytotaldose * (k ^ row))
                else " "),
             (if (($firstdaytotaldose * (k ^ row)) >= 0.001)
                then ($firstdaytotaldose * (k ^ row))
                else " "))
     3    @if(($createormodify == "CREATE"),
             (if (row <= $durationtoplot)
                then (r7c3 + r8c2)
                else " "),
             (if r8c2 > 0
                then (r7c3 + r8c2)
                else " "))
     4    if ( ($createormodify == "CREATE") and (row <= $durationtoplot)) then
             choose( (val(right($mathmodel,1))),
```

FORMULAS FOR WORKSHEET TAPERCAL

| ROW | COL | FORMULA |
|---|---|---|

```
                        "",
                        (round((r8c2/$mindosesizeavail),0)*$mindosesizeavail),
                        (round(((r8c3-r7c5)/$mindosesizeavail),0)*$mindosesizeavail),
                        (min((r7c4),(round(((r8c3-r7c5)/$mindosesizeavail),0)*$mindosesizeavail)))
                        )
                    else
                        if ( ($createormodify == "MODIFY") and
                             (((r7c4 > 0) or ($mathmodel=="Model_2")) ) then
                            choose( (val(right($mathmodel,1))),
                                " ",
                                (round((r8c2/$mindosesizeavail),0)*$mindosesizeavail),
                                (if ((round(((r8c3-r7c5)/$mindosesizeavail),0)*$mindosesizeavail)> 0) then
                                    (round(((r8c3-r7c5)/$mindosesizeavail),0)*$mindosesizeavail)
                                 else " "),
                                (min((r7c4),(round(((r8c3-r7c5)/$mindosesizeavail),0)*$mindosesizeavail)))
                                )
                        else
                                " "
    5   if( (($createormodify == "CREATE") and (row <= $durationtoplot)) or
            (($createormodify == "MODIFY") and (r8c2 >= 0.001)))
        then
            r7c5+r8c4 else " "
    6   if( (($createormodify == "CREATE") and (row <= $durationtoplot)) or
            (($createormodify == "MODIFY") and (r8c2 >= 0.001)))
        then
            row else " "
9   2   @if(($createormodify == "CREATE"),
            (if (row <= $durationtoplot)
                then ($firstdaytotaldose * (k ^ row))
                else " "),
            (if (($firstdaytotaldose * (k ^ row)) >= 0.001)
                then ($firstdaytotaldose * (k ^ row))
                else " "))
    3   @if(($createormodify == "CREATE"),
            (if (row <= $durationtoplot)
                then (r8c3 + r9c2)
                else " "),
            (if r9c2 > 0
                then (r8c3 + r9c2)
                else " "))
    4   if ( ($createormodify == "CREATE") and (row <= $durationtoplot)) then
            choose( (val(right($mathmodel,1))),
                "",
                (round((r9c2/$mindosesizeavail),0)*$mindosesizeavail),
                (round(((r9c3-r8c5)/$mindosesizeavail),0)*$mindosesizeavail),
                (min((r8c4),(round(((r9c3-r8c5)/$mindosesizeavail),0)*$mindosesizeavail)))
                )
            else
                if ( ($createormodify == "MODIFY") and
                     (((r8c4 > 0) or ($mathmodel=="Model_2")) ) then
                    choose( (val(right($mathmodel,1))),
                        " ",
                        (round((r9c2/$mindosesizeavail),0)*$mindosesizeavail),
                        (if ((round(((r9c3-r8c5)/$mindosesizeavail),0)*$mindosesizeavail)> 0) then
                            (round(((r9c3-r8c5)/$mindosesizeavail),0)*$mindosesizeavail)
                         else " "),
                        (min((r8c4),(round(((r9c3-r8c5)/$mindosesizeavail),0)*$mindosesizeavail)))
                        )
                else
                    " "
    5   if( (($createormodify == "CREATE") and (row <= $durationtoplot)) or
            (($createormodify == "MODIFY") and (r9c2 >= 0.001)))
        then
            r8c5+r9c4 else " "
    6   if( (($createormodify == "CREATE") and (row <= $durationtoplot)) or
            (($createormodify == "MODIFY") and (r9c2 >= 0.001)))
        then
            row else " "
10  2   @if(($createormodify == "CREATE"),
```

FORMULAS FOR WORKSHEET TAPERCAL

ROW COL FORMULA

```
            (if (row <= $durationtoplot)
              then ($firstdaytotaldose * (k ^ row))
              else " "),
            (if (($firstdaytotaldose * (k ^ row)) >= 0.001)
              then ($firstdaytotaldose * (k ^ row))
              else " "))
    3   @if(($createormodify == "CREATE"),
            (if (row <= $durationtoplot)
              then (r9c3 + r10c2)
              else " "),
            (if r10c2 > 0
              then (r9c3 + r10c2)
              else " "))
    4   if ( ($createormodify == "CREATE") and (row <= $durationtoplot)) then
            choose( (val(right($mathmodel,1))),
              " ",
              (round((r10c2/$mindosesizeavail),0)*$mindosesizeavail),
              (round(((r10c3-r9c5)/$mindosesizeavail),0)*$mindosesizeavail),
              (min((r9c4),(round(((r10c3-r9c5)/$mindosesizeavail),0)*$mindosesizeavail)))
            )
            else
              if ( ($createormodify == "MODIFY") and
                  ((r9c4 > 0) or ($mathmodel=="Model_2")) ) then
                choose( (val(right($mathmodel,1))),
                  " ",
                  (round((r10c2/$mindosesizeavail),0)*$mindosesizeavail),
                  (if ((round(((r10c3-r9c5)/$mindosesizeavail),0)*$mindosesizeavail)> 0) then
                    (round(((r10c3-r9c5)/$mindosesizeavail),0)*$mindosesizeavail)
                    else " "),
                  (min((r9c4),(round(((r10c3-r9c5)/$mindosesizeavail),0)*$mindosesizeavail)))
                )
                else
                  " "
    5   if( (($createormodify == "CREATE") and (row <= $durationtoplot)) or
            ($createormodify == "MODIFY") and (r10c2 >= 0.001))
            then
            r9c5+r10c4 else " "
    6   if( (($createormodify == "CREATE") and (row <= $durationtoplot)) or
            (($createormodify == "MODIFY") and (r10c2 >= 0.001)))
            then
            row else " "
```

FORMULAS FOR WORKSHEET TAPERDIS

| ROW | COL | FORMULA |
|---|---|---|
| 1 | 1 | if (tapercal.r1c[4]>0) then<br>tapercal.r1c[4]<br>else " " |
|  | 3 | if (select ((Stimespanforeachdose == "DAY"),tapercal.r15c[4]) else tapercal.r16c4 > 0)<br>then select ((Stimespanforeachdose == "DAY"),tapercal.r15c[4]) else tapercal.r16c4<br>else " " |
|  | 4 | select (Stimespanforeachdose=="WEEK","+") else "\|" |
|  | 5 | if (select (Stimespanforeachdose=="DAY",tapercal.r29c[4]) else tapercal.r31c[4]>0) then<br>select (Stimespanforeachdose=="DAY",tapercal.r29c[4]) else tapercal.r31c[4]<br>else " " |
|  | 7 | if (select (Stimespanforeachdose=="DAY",tapercal.r43c[4]) else tapercal.r46c[4]>0) then<br>select (Stimespanforeachdose=="DAY",tapercal.r43c[4]) else tapercal.r46c[4]<br>else " " |
|  | 9 | if (select (Stimespanforeachdose=="DAY",tapercal.r57c[4]) else tapercal.r61c[4]>0) then<br>select (Stimespanforeachdose=="DAY",tapercal.r57c[4]) else tapercal.r61c[4]<br>else " " |
|  | 11 | if (select (Stimespanforeachdose=="DAY",tapercal.r71c[4]) else tapercal.r76c[4]> 0) then<br>select (Stimespanforeachdose=="DAY",tapercal.r71c[4]) else tapercal.r76c[4]<br>else " " |
|  | 12 | select (Stimespanforeachdose=="WEEK","+") else "\|" |
|  | 13 | if(select (Stimespanforeachdose=="DAY",tapercal.r85c[4]) else tapercal.r91c[4]>0) then<br>select (Stimespanforeachdose=="DAY",tapercal.r85c[4]) else tapercal.r91c[4]<br>else " " |
| 2 | 1 | if (tapercal.r2c[4]>0) then<br>tapercal.r2c[4]<br>else " " |
|  | 3 | if (select ((Stimespanforeachdose == "DAY"),tapercal.r16c[4]) else tapercal.r17c4 > 0)<br>then select ((Stimespanforeachdose == "DAY"),tapercal.r16c[4]) else tapercal.r17c4<br>else " " |
|  | 5 | if (select (Stimespanforeachdose=="DAY",tapercal.r30c[4]) else tapercal.r32c[4]>0) then<br>select (Stimespanforeachdose=="DAY",tapercal.r30c[4]) else tapercal.r32c[4]<br>else " " |
|  | 6 | select (Stimespanforeachdose=="WEEK","+") else "\|" |
|  | 7 | if (select (Stimespanforeachdose=="DAY",tapercal.r44c[4]) else tapercal.r47c[4]>0) then<br>select (Stimespanforeachdose=="DAY",tapercal.r44c[4]) else tapercal.r47c[4]<br>else " " |
|  | 9 | if (select (Stimespanforeachdose=="DAY",tapercal.r58c[4]) else tapercal.r62c[4]>0) then<br>select (Stimespanforeachdose=="DAY",tapercal.r58c[4]) else tapercal.r62c[4]<br>else " " |
|  | 11 | if (select (Stimespanforeachdose=="DAY",tapercal.r72c[4]) else tapercal.r77c[4]> 0) then<br>select (Stimespanforeachdose=="DAY",tapercal.r72c[4]) else tapercal.r77c[4]<br>else " " |
|  | 13 | if(select (Stimespanforeachdose=="DAY",tapercal.r86c[4]) else tapercal.r92c[4]>0) then<br>select (Stimespanforeachdose=="DAY",tapercal.r86c[4]) else tapercal.r92c[4]<br>else " " |
|  | 14 | select (Stimespanforeachdose=="WEEK","+") else "\|" |
| 3 | 1 | if (tapercal.r3c[4]>0) then<br>tapercal.r3c[4]<br>else " " |
|  | 3 | if (select ((Stimespanforeachdose == "DAY"),tapercal.r17c[4]) else tapercal.r18c4 > 0)<br>then select ((Stimespanforeachdose == "DAY"),tapercal.r17c[4]) else tapercal.r18c4<br>else " " |
|  | 4 | select (Stimespanforeachdose == "HOUR","+")(Stimespanforeachdose=="MONTH","+") else "\|" |
|  | 5 | if (select (Stimespanforeachdose=="DAY",tapercal.r31c[4]) else tapercal.r33c[4]>0) then<br>select (Stimespanforeachdose=="DAY",tapercal.r31c[4]) else tapercal.r33c[4]<br>else " " |
|  | 7 | if (select (Stimespanforeachdose=="DAY",tapercal.r45c[4]) else tapercal.r48c[4]>0) then<br>select (Stimespanforeachdose=="DAY",tapercal.r45c[4]) else tapercal.r48c[4]<br>else " " |
|  | 8 | select (Stimespanforeachdose == "HOUR","<")(Stimespanforeachdose == "WEEK","+")<br>(Stimespanforeachdose == "MONTH","<") else "\|" |
|  | 9 | if (select (Stimespanforeachdose=="DAY",tapercal.r59c[4]) else tapercal.r63c[4]>0) then<br>select (Stimespanforeachdose=="DAY",tapercal.r59c[4]) else tapercal.r63c[4]<br>else " " |
|  | 11 | if (select (Stimespanforeachdose=="DAY",tapercal.r73c[4]) else tapercal.r78c[4]> 0) then<br>select (Stimespanforeachdose=="DAY",tapercal.r73c[4]) else tapercal.r78c[4]<br>else " " |

FORMULAS FOR WORKSHEET TAPERDIS

| ROW | COL | FORMULA |
|---|---|---|
| | | select ($timespanforeachdose=="DAY",tapercal.r87c[4]) else tapercal.r93c[4] else " " |
| 4 | 1 | if (tapercal.r4c[4]>0) then<br>tapercal.r4c[4]<br>else " " |
| | 2 | select ($timespanforeachdose=="WEEK","+") else "|" |
| | 3 | if (select (($timespanforeachdose == "DAY"),tapercal.r18c[4]) else tapercal.r19c4 > 0)<br>then select (($timespanforeachdose == "DAY"),tapercal.r18c[4]) else tapercal.r19c4<br>else " " |
| | 5 | if (select ($timespanforeachdose=="DAY",tapercal.r32c[4]) else tapercal.r34c[4]>0) then<br>select ($timespanforeachdose=="DAY",tapercal.r32c[4]) else tapercal.r34c[4]<br>else " " |
| | 7 | if (select ($timespanforeachdose=="DAY",tapercal.r46c[4]) else tapercal.r49c[4]>0) then<br>select ($timespanforeachdose=="DAY",tapercal.r46c[4]) else tapercal.r49c[4]<br>else " " |
| | 9 | if (select ($timespanforeachdose=="DAY",tapercal.r60c[4]) else tapercal.r64c[4]>0) then<br>select ($timespanforeachdose=="DAY",tapercal.r60c[4]) else tapercal.r64c[4]<br>else " " |
| | 10 | select ($timespanforeachdose=="WEEK","+") else "|" |
| | 11 | if (select ($timespanforeachdose=="DAY",tapercal.r74c[4]) else tapercal.r79c[4]> 0) then<br>select ($timespanforeachdose=="DAY",tapercal.r74c[4]) else tapercal.r79c[4]<br>else " " |
| | 13 | if(select ($timespanforeachdose=="DAY",tapercal.r88c[4]) else tapercal.r94c[4]>0) then<br>select ($timespanforeachdose=="DAY",tapercal.r88c[4]) else tapercal.r94c[4]<br>else " " |
| 5 | 1 | if (tapercal.r5c[4]>0) then<br>tapercal.r5c[4]<br>else " " |
| | 2 | select ($timespanforeachdose=="MINUTE","+") else "|" |
| | 3 | if (select (($timespanforeachdose == "DAY"),tapercal.r19c[4]) else tapercal.r20c4 > 0)<br>then select (($timespanforeachdose == "DAY"),tapercal.r19c[4]) else tapercal.r20c4<br>else " " |
| | 4 | select ($timespanforeachdose=="MINUTE","+")($timespanforeachdose=="WEEK","+") else "|" |
| | 5 | if (select ($timespanforeachdose=="DAY",tapercal.r33c[4]) else tapercal.r35c[4]>0) then<br>select ($timespanforeachdose=="DAY",tapercal.r33c[4]) else tapercal.r35c[4]<br>else " " |
| | 6 | select ($timespanforeachdose=="MINUTE","+") else "|" |
| | 7 | if (select ($timespanforeachdose=="DAY",tapercal.r47c[4]) else tapercal.r50c[4]>0) then<br>select ($timespanforeachdose=="DAY",tapercal.r47c[4]) else tapercal.r50c[4]<br>else " " |
| | 8 | select ($timespanforeachdose=="MINUTE","+") else "|" |
| | 9 | if (select ($timespanforeachdose=="DAY",tapercal.r61c[4]) else tapercal.r65c[4]>0) then<br>select ($timespanforeachdose=="DAY",tapercal.r61c[4]) else tapercal.r65c[4]<br>else " " |
| | 10 | select ($timespanforeachdose=="MINUTE","+") else "|" |
| | 11 | if (select ($timespanforeachdose=="DAY",tapercal.r75c[4]) else tapercal.r80c[4]> 0) then<br>select ($timespanforeachdose=="DAY",tapercal.r75c[4]) else tapercal.r80c[4]<br>else " " |
| | 12 | select ($timespanforeachdose=="MINUTE","+")($timespanforeachdose=="WEEK","+") else "|" |
| | 13 | if(select ($timespanforeachdose=="DAY",tapercal.r89c[4]) else tapercal.r95c[4]>0) then<br>select ($timespanforeachdose=="DAY",tapercal.r89c[4]) else tapercal.r95c[4]<br>else " " |
| | 14 | select ($timespanforeachdose=="MINUTE","+") else "|" |
| 6 | 1 | if (tapercal.r6c[4]>0) then<br>tapercal.r6c[4]<br>else " " |
| | 2 | select ($timespanforeachdose=="MONTH","+")($timespanforeachdose == "HOUR","+") else "|" |
| | 3 | if (select (($timespanforeachdose == "DAY"),tapercal.r20c[4]) else tapercal.r21c4 > 0)<br>then select (($timespanforeachdose == "DAY"),tapercal.r20c[4]) else tapercal.r21c4<br>else " " |
| | 5 | if (select ($timespanforeachdose=="DAY",tapercal.r34c[4]) else tapercal.r36c[4]>0) then<br>select ($timespanforeachdose=="DAY",tapercal.r34c[4]) else tapercal.r36c[4]<br>else " " |
| | 6 | select ($timespanforeachdose == "HOUR","+")($timespanforeachdose == "WEEK","+")<br>($timespanforeachdose == "MONTH","<") else "|" |
| | 7 | if (select ($timespanforeachdose=="DAY",tapercal.r48c[4]) else tapercal.r51c[4]>0) then<br>select ($timespanforeachdose=="DAY",tapercal.r48c[4]) else tapercal.r51c[4] |

FORMULAS FOR WORKSHEET TAPERDIS

| ROW | COL | FORMULA |
|---|---|---|
| | | select ($timespanforeachdose=="DAY",tapercal.r62c[4]) else tapercal.r66c[4] else " " |
| | 10 | select ($timespanforeachdose == "HOUR","+")($timespanforeachdose=="MONTH","+") else "|" |
| | 11 | if (select ($timespanforeachdose=="DAY",tapercal.r76c[4]) else tapercal.r81c[4]> 0) then select ($timespanforeachdose=="DAY",tapercal.r76c[4]) else tapercal.r81c[4] else " " |
| | 13 | if(select ($timespanforeachdose=="DAY",tapercal.r90c[4]) else tapercal.r96c[4]>0) then select ($timespanforeachdose=="DAY",tapercal.r90c[4]) else tapercal.r96c[4] else " " |
| | 14 | select ($timespanforeachdose=="HOUR","<")($timespanforeachdose=="WEEK","+")($timespanforeachdo else "|" |
| 7 | 1 | if (tapercal.r7c[4]>0) then tapercal.r7c[4] else " " |
| | 2 | select ($timespanforeachdose == "DAY","+") else "|" |
| | 3 | if (select (($timespanforeachdose == "DAY"),tapercal.r21c[4]) else tapercal.r22c4 > 0) then select (($timespanforeachdose == "DAY"),tapercal.r21c[4]) else tapercal.r22c4 else " " |
| | 4 | select ($timespanforeachdose == "DAY","+") else "|" |
| | 5 | if (select ($timespanforeachdose=="DAY",tapercal.r35c[4]) else tapercal.r37c[4]>0) then select ($timespanforeachdose=="DAY",tapercal.r35c[4]) else tapercal.r37c[4] else " " |
| | 6 | select ($timespanforeachdose == "DAY","+") else "|" |
| | 7 | if (select ($timespanforeachdose=="DAY",tapercal.r49c[4]) else tapercal.r52c[4]>0) then select ($timespanforeachdose=="DAY",tapercal.r49c[4]) else tapercal.r52c[4] else " " |
| | 8 | select ($timespanforeachdose == "DAY","+")($timespanforeachdose == "WEEK","<") else "|" |
| | 9 | if (select ($timespanforeachdose=="DAY",tapercal.r63c[4]) else tapercal.r67c[4]>0) then select ($timespanforeachdose=="DAY",tapercal.r63c[4]) else tapercal.r67c[4] else " " |
| | 10 | select ($timespanforeachdose == "DAY","+") else "|" |
| | 11 | if (select ($timespanforeachdose=="DAY",tapercal.r77c[4]) else tapercal.r82c[4]> 0) then select ($timespanforeachdose=="DAY",tapercal.r77c[4]) else tapercal.r82c[4] else " " |
| | 12 | select ($timespanforeachdose == "DAY","+") else "|" |
| | 13 | if(select ($timespanforeachdose=="DAY",tapercal.r91c[4]) else tapercal.r97c[4]>0) then select ($timespanforeachdose=="DAY",tapercal.r91c[4]) else tapercal.r97c[4] else " " |
| | 14 | select ($timespanforeachdose == "DAY","+") else "|" |
| 8 | 1 | if (tapercal.r8c[4]>0) then tapercal.r8c[4] else " " |
| | 2 | select ($timespanforeachdose=="WEEK","+") else "|" |
| | 3 | if (select (($timespanforeachdose == "DAY"),tapercal.r22c[4]) else tapercal.r23c4 > 0) then select (($timespanforeachdose == "DAY"),tapercal.r22c[4]) else tapercal.r23c4 else " " |
| | 5 | if (select ($timespanforeachdose=="DAY",tapercal.r36c[4]) else tapercal.r38c[4]>0) then select ($timespanforeachdose=="DAY",tapercal.r36c[4]) else tapercal.r38c[4] else " " |
| | 7 | if (select ($timespanforeachdose=="DAY",tapercal.r50c[4]) else tapercal.r53c[4]>0) then select ($timespanforeachdose=="DAY",tapercal.r50c[4]) else tapercal.r53c[4] else " " |
| | 9 | if (select ($timespanforeachdose=="DAY",tapercal.r64c[4]) else tapercal.r68c[4]>0) then select ($timespanforeachdose=="DAY",tapercal.r64c[4]) else tapercal.r68c[4] else " " |
| | 10 | select ($timespanforeachdose=="WEEK","+") else "|" |
| | 11 | if (select ($timespanforeachdose=="DAY",tapercal.r78c[4]) else tapercal.r83c[4]> 0) then select ($timespanforeachdose=="DAY",tapercal.r78c[4]) else tapercal.r83c[4] else " " |
| | 13 | if(select ($timespanforeachdose=="DAY",tapercal.r92c[4]) else tapercal.r98c[4]>0) then select ($timespanforeachdose=="DAY",tapercal.r92c[4]) else tapercal.r98c[4] else " " |
| 9 | 1 | if (tapercal.r9c[4]>0) then tapercal.r9c[4] else " " |
| | 3 | if (select (($timespanforeachdose == "DAY"),tapercal.r23c[4]) else tapercal.r24c4 > 0) then select (($timespanforeachdose == "DAY"),tapercal.r23c[4]) else tapercal.r24c4 |

FORMULAS FOR WORKSHEET TAPER01S

| ROW | COL | FORMULA |
|---|---|---|
| | | ($timespanforeachdose == "MONTH","<") else "|" |
| | 5 | if (select ($timespanforeachdose=="DAY",tapercal.r37c[4]) else tapercal.r39c[4]>0) then<br>select ($timespanforeachdose=="DAY",tapercal.r37c[4]) else tapercal.r39c[4]<br>else " " |
| | 7 | if (select ($timespanforeachdose=="DAY",tapercal.r51c[4]) else tapercal.r54c[4]>0) then<br>select ($timespanforeachdose=="DAY",tapercal.r51c[4]) else tapercal.r54c[4]<br>else " " |
| | 8 | select ($timespanforeachdose == "HOUR","+")($timespanforeachdose=="MONTH","+") else "|" |
| | 9 | if (select ($timespanforeachdose=="DAY",tapercal.r65c[4]) else tapercal.r69c[4]>0) then<br>select ($timespanforeachdose=="DAY",tapercal.r65c[4]) else tapercal.r69c[4]<br>else " " |
| | 11 | if (select ($timespanforeachdose=="DAY",tapercal.r79c[4]) else tapercal.r84c[4]> 0) then<br>select ($timespanforeachdose=="DAY",tapercal.r79c[4]) else tapercal.r84c[4]<br>else " " |
| | 12 | select ($timespanforeachdose == "HOUR","+")($timespanforeachdose=="WEEK","+")<br>($timespanforeachdose == "MONTH","<") else "|" |
| | 13 | if(select ($timespanforeachdose=="DAY",tapercal.r93c[4]) else tapercal.r99c[4]>0) then<br>select ($timespanforeachdose=="DAY",tapercal.r93c[4]) else tapercal.r99c[4]<br>else " " |
| 10 | 1 | if (tapercal.r10c[4]>0) then<br>tapercal.r10c[4]<br>else " " |
| | 2 | select ($timespanforeachdose=="MINUTE","+") else "|" |
| | 3 | if (select (($timespanforeachdose == "DAY"),tapercal.r24c[4]) else tapercal.r25c4 > 0)<br>then select (($timespanforeachdose == "DAY"),tapercal.r24c[4]) else tapercal.r25c4<br>else " " |
| | 4 | select ($timespanforeachdose=="MINUTE","+") else "|" |
| | 5 | if (select ($timespanforeachdose=="DAY",tapercal.r38c[4]) else tapercal.r40c[4]>0) then<br>select ($timespanforeachdose=="DAY",tapercal.r38c[4]) else tapercal.r40c[4]<br>else " " |
| | 6 | select ($timespanforeachdose=="MINUTE","+")($timespanforeachdose=="WEEK","+") else "|" |
| | 7 | if (select ($timespanforeachdose=="DAY",tapercal.r52c[4]) else tapercal.r55c[4]>0) then<br>select ($timespanforeachdose=="DAY",tapercal.r52c[4]) else tapercal.r55c[4]<br>else " " |
| | 8 | select ($timespanforeachdose=="MINUTE","+") else "|" |
| | 9 | if (select ($timespanforeachdose=="DAY",tapercal.r66c[4]) else tapercal.r70c[4]>0) then<br>select ($timespanforeachdose=="DAY",tapercal.r66c[4]) else tapercal.r70c[4]<br>else " " |
| | 10 | select ($timespanforeachdose=="MINUTE","+") else "|" |
| | 11 | if (select ($timespanforeachdose=="DAY",tapercal.r80c[4]) else tapercal.r85c[4]> 0) then<br>select ($timespanforeachdose=="DAY",tapercal.r80c[4]) else tapercal.r85c[4]<br>else " " |
| | 12 | select ($timespanforeachdose=="MINUTE","+") else "|" |
| | 13 | if(select ($timespanforeachdose=="DAY",tapercal.r94c[4]) else tapercal.r100c[4]>0) then<br>select ($timespanforeachdose=="DAY",tapercal.r94c[4]) else tapercal.r100c[4]<br>else " " |
| | 14 | select ($timespanforeachdose=="MINUTE","+")($timespanforeachdose=="WEEK","+") else "|" |
| 11 | 1 | if (tapercal.r11c[4]>0) then<br>tapercal.r11c[4]<br>else " " |
| | 3 | if (select (($timespanforeachdose == "DAY"),tapercal.r25c[4]) else tapercal.r26c4 > 0)<br>then select (($timespanforeachdose == "DAY"),tapercal.r25c[4]) else tapercal.r26c4<br>else " " |
| | 5 | if (select ($timespanforeachdose=="DAY",tapercal.r39c[4]) else tapercal.r41c[4]>0) then<br>select ($timespanforeachdose=="DAY",tapercal.r39c[4]) else tapercal.r41c[4]<br>else " " |
| | 7 | if (select ($timespanforeachdose=="DAY",tapercal.r53c[4]) else tapercal.r56c[4]>0) then<br>select ($timespanforeachdose=="DAY",tapercal.r53c[4]) else tapercal.r56c[4]<br>else " " |
| | 8 | select ($timespanforeachdose=="WEEK","+") else "|" |
| | 9 | if (select ($timespanforeachdose=="DAY",tapercal.r67c[4]) else tapercal.r71c[4]>0) then<br>select ($timespanforeachdose=="DAY",tapercal.r67c[4]) else tapercal.r71c[4]<br>else " " |
| | 11 | if (select ($timespanforeachdose=="DAY",tapercal.r81c[4]) else tapercal.r86c[4]> 0) then<br>select ($timespanforeachdose=="DAY",tapercal.r81c[4]) else tapercal.r86c[4]<br>else " " |
| | 13 | if(select ($timespanforeachdose=="DAY",tapercal.r95c[4]) else tapercal.r101c[4]>0) then |

FORMULAS FOR WORKSHEET TAPERDIS

| ROW | COL | FORMULA |
|---|---|---|
| 12 | 1 | if (tapercal.r12c[4]>0) then<br>    tapercal.r12c[4]<br>    else " " |
|  | 2 | select ($timespanforeachdose == "HOUR","+")($timespanforeachdose=="WEEK","+")($timespanforeach<br>    else "\|" |
|  | 3 | if (select (($timespanforeachdose == "DAY"),tapercal.r26c[4]) else tapercal.r27c4 > 0)<br>    then select (($timespanforeachdose == "DAY"),tapercal.r26c[4]) else tapercal.r27c4<br>    else " " |
|  | 5 | if (select ($timespanforeachdose=="DAY",tapercal.r40c[4]) else tapercal.r42c[4]>0) then<br>    select ($timespanforeachdose=="DAY",tapercal.r40c[4]) else tapercal.r42c[4]<br>    else " " |
|  | 6 | select ($timespanforeachdose == "HOUR","+")($timespanforeachdose=="MONTH","+") else "\|" |
|  | 7 | if (select ($timespanforeachdose=="DAY",tapercal.r54c[4]) else tapercal.r57c[4]>0) then<br>    select ($timespanforeachdose=="DAY",tapercal.r54c[4]) else tapercal.r57c[4]<br>    else " " |
|  | 9 | if (select ($timespanforeachdose=="DAY",tapercal.r68c[4]) else tapercal.r72c[4]>0) then<br>    select ($timespanforeachdose=="DAY",tapercal.r68c[4]) else tapercal.r72c[4]<br>    else " " |
|  | 10 | select ($timespanforeachdose == "HOUR","<") ($timespanforeachdose=="WEEK","+")<br>    ($timespanforeachdose == "MONTH","<") else "\|" |
|  | 11 | if (select ($timespanforeachdose=="DAY",tapercal.r82c[4]) else tapercal.r87c[4]> 0) then<br>    select ($timespanforeachdose=="DAY",tapercal.r82c[4]) else tapercal.r87c[4]<br>    else " " |
|  | 13 | if(select ($timespanforeachdose=="DAY",tapercal.r96c[4]) else tapercal.r102c[4]>0) then<br>    select ($timespanforeachdose=="DAY",tapercal.r96c[4]) else tapercal.r102c[4]<br>    else " " |
|  | 14 | select ($timespanforeachdose == "HOUR","+")($timespanforeachdose == "MONTH","+") else "\|" |
| 13 | 1 | if (tapercal.r13c[4]>0) then<br>    tapercal.r13c[4]<br>    else " " |
|  | 3 | if (select (($timespanforeachdose == "DAY"),tapercal.r27c[4]) else tapercal.r28c4 > 0)<br>    then select (($timespanforeachdose == "DAY"),tapercal.r27c[4]) else tapercal.r28c4<br>    else " " |
|  | 4 | select ($timespanforeachdose=="WEEK","+") else "\|" |
|  | 5 | if (select ($timespanforeachdose=="DAY",tapercal.r41c[4]) else tapercal.r43c[4]>0) then<br>    select ($timespanforeachdose=="DAY",tapercal.r41c[4]) else tapercal.r43c[4]<br>    else " " |
|  | 7 | if (select ($timespanforeachdose=="DAY",tapercal.r55c[4]) else tapercal.r58c[4]>0) then<br>    select ($timespanforeachdose=="DAY",tapercal.r55c[4]) else tapercal.r58c[4]<br>    else " " |
|  | 9 | if (select ($timespanforeachdose=="DAY",tapercal.r69c[4]) else tapercal.r73c[4]>0) then<br>    select ($timespanforeachdose=="DAY",tapercal.r69c[4]) else tapercal.r73c[4]<br>    else " " |
|  | 11 | if (select ($timespanforeachdose=="DAY",tapercal.r83c[4]) else tapercal.r88c[4]> 0) then<br>    select ($timespanforeachdose=="DAY",tapercal.r83c[4]) else tapercal.r88c[4]<br>    else " " |
|  | 12 | select ($timespanforeachdose=="WEEK","+") else "\|" |
|  | 13 | if(select ($timespanforeachdose=="DAY",tapercal.r97c[4]) else tapercal.r103c[4]>0) then<br>    select ($timespanforeachdose=="DAY",tapercal.r97c[4]) else tapercal.r103c[4]<br>    else " " |
| 14 | 1 | if (tapercal.r14c[4]>0) then<br>    tapercal.r14c[4]<br>    else " " |
|  | 2 | select ($timespanforeachdose == "DAY","+") else "\|" |
|  | 3 | if (select (($timespanforeachdose == "DAY"),tapercal.r28c[4]) else tapercal.r29c4 > 0)<br>    then select (($timespanforeachdose == "DAY"),tapercal.r28c[4]) else tapercal.r29c4<br>    else " " |
|  | 4 | select ($timespanforeachdose == "DAY","+") else "\|" |
|  | 5 | if (select ($timespanforeachdose=="DAY",tapercal.r42c[4]) else tapercal.r44c[4]>0) then<br>    select ($timespanforeachdose=="DAY",tapercal.r42c[4]) else tapercal.r44c[4]<br>    else " " |
|  | 6 | select ($timespanforeachdose == "DAY","+")($timespanforeachdose=="WEEK","+") else "\|" |
|  | 7 | if (select ($timespanforeachdose=="DAY",tapercal.r56c[4]) else tapercal.r59c[4]>0) then<br>    select ($timespanforeachdose=="DAY",tapercal.r56c[4]) else tapercal.r59c[4]<br>    else " " |
|  | 8 | select ($timespanforeachdose == "DAY","+") else "\|" |
|  | 9 | if (select ($timespanforeachdose=="DAY",tapercal.r70c[4]) else tapercal.r74c[4]>0) then |

```
FORMULAS FOR WORKSHEET TAPERDIS
ROW  COL  FORMULA
     10   select ($timespanforeachdose == "DAY","+") else "|"
     11   if (select ($timespanforeachdose=="DAY",tapercal.r84c[4]) else tapercal.r89c[4]> 0) then
            select ($timespanforeachdose=="DAY",tapercal.r84c[4]) else tapercal.r89c[4]
            else " "
     12   select ($timespanforeachdose == "DAY","+") else "|"
     13   if(select ($timespanforeachdose=="DAY",tapercal.r98c[4]) else tapercal.r104c[4]>0) then
            select ($timespanforeachdose=="DAY",tapercal.r98c[4]) else tapercal.r104c[4]
            else " "
     14   select ($timespanforeachdose == "DAY","+")($timespanforeachdose=="WEEK","<") else "|"
15   1    if ($timespanforeachdose == "DAY") then " " else
            ( if ( tapercal.r15c[4]>0) then
              tapercal.r15c[4] else " ")
     2    select ($timespanforeachdose=="DAY","")($timespanforeachdose=="MINUTE","+") else "|"
     3    if ($timespanforeachdose == "DAY") then " " else
            ( if ( tapercal.r30c[4]>0) then
              tapercal.r30c[4] else " ")
     4    select ($timespanforeachdose=="DAY","")($timespanforeachdose="MINUTE","+")($timespanforeachdo
            ($timespanforeachdose=="MONTH","+") else "|"
     5    if ($timespanforeachdose == "DAY") then " " else
            ( if ( tapercal.r45c[4]>0) then
              tapercal.r45c[4] else " ")
     6    select ($timespanforeachdose=="DAY","")($timespanforeachdose=="MINUTE","+") else "|"
     7    if ($timespanforeachdose == "DAY") then " " else
            ( if ( tapercal.r60c[4]>0) then
              tapercal.r60c[4] else " ")
     8    select ($timespanforeachdose=="DAY","")($timespanforeachdose=="MINUTE","+")($timespanforeachdo
            ($timespanforeachdose=="WEEK","+")($timespanforeachdose=="MONTH","<") else "|"
     9    if ($timespanforeachdose == "DAY") then " " else
            ( if ( tapercal.r75c[4]>0) then
              tapercal.r75c[4] else " ")
     10   select ($timespanforeachdose=="DAY","")($timespanforeachdose=="MINUTE","+") else "|"
     11   if ($timespanforeachdose == "DAY") then " " else
            ( if ( tapercal.r90c[4]>0) then
              tapercal.r90c[4] else " ")
     12   select ($timespanforeachdose=="DAY","")($timespanforeachdose=="MINUTE","+")($timespanforeachdo
            ($timespanforeachdose=="MONTH","+") else "|"
     13   if ($timespanforeachdose == "DAY") then " " else
            ( if ( tapercal.r105c[4]>0) then
              tapercal.r105c[4] else " ")
     14   select ($timespanforeachdose=="DAY","")($timespanforeachdose=="MINUTE","+") else "|"
16   1    "Values represent doses for each" & $timespanforeachdose
19   13   $mathmodel
```

| Taper cal Total Dose | dates | exact dosage 7 AM | exact dosage 12 Noon | exact dosage 5 PM | exact dosage 10 PM |
|---|---|---|---|---|---|
| 500.000 | 04/19/1990 | 125.000 | 125.000 | 125.000 | 125.000 |
| 315.000 | 04/20/1990 | 80.000 | 75.000 | 80.000 | 80.000 |
| 250.000 | 04/21/1990 | 65.000 | 60.000 | 60.000 | 65.000 |
| 200.000 | 04/22/1990 | 50.000 | 50.000 | 50.000 | 50.000 |
| 160.000 | 04/23/1990 | 40.000 | 40.000 | 40.000 | 40.000 |
| 125.000 | 04/24/1990 | 30.000 | 30.000 | 30.000 | 35.000 |
| 100.000 | 04/25/1990 | 25.000 | 25.000 | 25.000 | 25.000 |
| 80.000 | 04/26/1990 | 20.000 | 20.000 | 20.000 | 20.000 |
| 65.000 | 04/27/1990 | 15.000 | 15.000 | 15.000 | 20.000 |
| 50.000 | 04/28/1990 | 15.000 | 10.000 | 10.000 | 15.000 |

| | | |
|---|---|---|
| 100.000 | 25.000 | 0.000 |
| 63.000 | 15.750 | 3.000 |
| 50.000 | 12.500 | 2.000 |
| 40.000 | 10.000 | 0.000 |
| 32.000 | 8.000 | 0.000 |
| 25.000 | 6.250 | 1.000 |
| 20.000 | 5.000 | 0.000 |
| 16.000 | 4.000 | 0.000 |
| 13.000 | 3.250 | 1.000 |
| 10.000 | 2.500 | 2.000 |

| Total Dose | | 7 AM | 12 Noon | 5 PM | 10 PM |
|---|---|---|---|---|---|
| 500.000 | 04/19/1990 | 125.000 | 125.000 | 125.000 | 125.000 |
| 315.000 | 04/20/1990 | 80.000 | 75.000 | 80.000 | 80.000 |
| 250.000 | 04/21/1990 | 65.000 | 60.000 | 60.000 | 65.000 |
| 200.000 | 04/22/1990 | 50.000 | 50.000 | 50.000 | 50.000 |
| 160.000 | 04/23/1990 | 40.000 | 40.000 | 40.000 | 40.000 |
| 125.000 | 04/24/1990 | 30.000 | 30.000 | 30.000 | 35.000 |
| 100.000 | 04/25/1990 | 25.000 | 25.000 | 25.000 | 25.000 |
| 80.000 | 04/26/1990 | 20.000 | 20.000 | 20.000 | 20.000 |
| 65.000 | 04/27/1990 | 15.000 | 15.000 | 15.000 | 20.000 |
| 50.000 | 04/28/1990 | 15.000 | 10.000 | 10.000 | 15.000 |

FORMULAS FOR WORKSHEET Schedule

| ROW | COL | FORMULA |
|---|---|---|
| 1 | 3 | $timefordose_1 |
|  | 5 | if $nrdosespertimeunit >= 3 then $timefordose_3 else " " |
|  | 6 | if $nrdosespertimeunit >= 4 then $timefordose_4 else " " |
|  | 7 | if $nrdosespertimeunit >= 5 then $timefordose_5 else " " |
|  | 8 | if $nrdosespertimeunit >= 6 then $timefordose_6 else " " |
| 3 | 1 | tapercal.r1c4 |
|  | 2 | if (r3c[10] > 0) then<br>( if $timespanforeachdose == "MINUTE" then addminutes($dateforfirstdose,row-4)<br>else if $timespanforeachdose == "HOUR" then addhours($dateforfirstdose,row-4)<br>else if $timespanforeachdose == "DAY" then adddays($dateforfirstdose,row-4)<br>else if $timespanforeachdose == "WEEK" then adddays($dateforfirstdose,7*(row-4))<br>else if $timespanforeachdose == "MONTH" then addmonths($dateforfirstdose,row-4)<br>else " " )<br>else " " |
|  | 3 | if (r3c[10] > 0) then<br>choose( $nrdosespertimeunit,<br>" ",<br>(int(r3c[10]))*$mindosesizeavail,<br>(int(r3c[10]))*$mindosesizeavail,<br>(int(r3c[10]) + choose (r3c[11], 0, 0, 1, 0, 0, 0))*$mindosesizeavail,<br>(int(r3c[10]) + choose (r3c[11], 0, 0, 1, 1, 0, 0))*$mindosesizeavail,<br>(int(r3c[10]) + choose (r3c[11], 0, 0, 1, 1, 1, 0))*$mindosesizeavail,<br>(int(r3c[10]) + choose (r3c[11], 0, 0, 1, 1, 1, 1))*$mindosesizeavail)<br>else " " |
|  | 4 | if (r3c[10] > 0 and $nrdosespertimeunit >= 2) then<br>choose( $nrdosespertimeunit,<br>" ",<br>0,<br>(int(r3c[10]) + choose (r3c[11], 0, 1, 0, 0, 0, 0))*$mindosesizeavail,<br>(int(r3c[10]))*$mindosesizeavail,<br>(int(r3c[10]))*$mindosesizeavail,<br>(int(r3c[10]))*$mindosesizeavail,<br>(int(r3c[10]))*$mindosesizeavail)<br>else " " |
|  | 5 | if (r3c[10] > 0 and $nrdosespertimeunit >= 3) then<br>choose( $nrdosespertimeunit,<br>" ",<br>0,<br>0,<br>(int(r3c[10]) + choose (r3c[11], 0, 1, 1, 0, 0, 0))*$mindosesizeavail,<br>(int(r3c[10]) + choose (r3c[11], 0, 0, 0, 1, 0, 0))*$mindosesizeavail,<br>(int(r3c[10]) + choose (r3c[11], 0, 0, 0, 1, 1, 0))*$mindosesizeavail,<br>(int(r3c[10]) + choose (r3c[11], 0, 0, 0, 1, 1, 1))*$mindosesizeavail)<br>else " " |
|  | 6 | if (r3c[10] > 0 and $nrdosespertimeunit >= 4) then<br>choose( $nrdosespertimeunit,<br>" ",<br>0,<br>0,<br>0,<br>(int(r3c[10]) + choose (r3c[11], 0, 1, 1, 1, 0, 0))*$mindosesizeavail,<br>(int(r3c[10]) + choose (r3c[11], 0, 0, 0, 0, 1, 0))*$mindosesizeavail,<br>(int(r3c[10]) + choose (r3c[11], 0, 0, 0, 0, 0, 1))*$mindosesizeavail)<br>else " " |
|  | 7 | if (r3c[10] > 0 and $nrdosespertimeunit >= 5) then<br>choose( $nrdosespertimeunit,<br>" ",<br>0,<br>0,<br>0,<br>0,<br>(int(r3c[10]) + choose (r3c[11], 0, 1, 1, 1, 1, 0))*$mindosesizeavail,<br>(int(r3c[10]) + choose (r3c[11], 0, 0, 0, 0, 1, 1))*$mindosesizeavail)<br>else " " |
|  | 8 | if (r3c[10] > 0 and $nrdosespertimeunit >= 6) then<br>choose( $nrdosespertimeunit,<br>" ",<br>0, |

FORMULAS FOR WORKSHEET SchedDis

| ROW | COL | FORMULA |
|---|---|---|

```
                          0,
                          0,
                          0,
                          0,
                          (int(r3c[10]) + choose (r3c[11], 0, 1, 1, 1, 1, 1))*$mindosesizeavail)
                      else " "
      9    If (r3c1/$mindosesizeavail> 0) then (r3c1/$mindosesizeavail) else " "
     10    If (r3c9/$nrdosespertimeunit > 0) then
                          (r3c9/$nrdosespertimeunit) else " "
     11    If (r3c10 > 0) then
                          r3c9 - ( int(r3c10) * $nrdosespertimeunit)
                      else " "
 4    1    tapercal.r2c4
      2    if (r4c[10] > 0) then
                      ( If $timespanforeachdose == "MINUTE" then addminutes($dateforfirstdose,row-4)
                        else if $timespanforeachdose == "HOUR" then addhours($dateforfirstdose,row-4)
                        else if $timespanforeachdose == "DAY" then adddays($dateforfirstdose,row-4)
                        else if $timespanforeachdose == "WEEK" then adddays($dateforfirstdose,7*(row-4))
                        else if $timespanforeachdose == "MONTH" then addmonths($dateforfirstdose,row-4)
                        else " " )
                      else " "
      3    If (r4c[10] > 0) then
                      choose( $nrdosespertimeunit,
                          " ",
                          (int(r4c[10]))*$mindosesizeavail,
                          (int(r4c[10]))*$mindosesizeavail,
                          (int(r4c[10]) + choose (r4c[11], 0, 0, 1, 0, 0, 0))*$mindosesizeavail,
                          (int(r4c[10]) + choose (r4c[11], 0, 0, 1, 1, 0, 0))*$mindosesizeavail,
                          (int(r4c[10]) + choose (r4c[11], 0, 0, 1, 1, 1, 0))*$mindosesizeavail,
                          (int(r4c[10]) + choose (r4c[11], 0, 0, 1, 1, 1, 1))*$mindosesizeavail)
                      else " "
      4    If (r4c[10] > 0 and $nrdosespertimeunit >= 2) then
                      choose( $nrdosespertimeunit,
                          " ",
                          0,
                          (int(r4c[10]) + choose (r4c[11], 0, 1, 0, 0, 0, 0))*$mindosesizeavail,
                          (int(r4c[10]))*$mindosesizeavail,
                          (int(r4c[10]))*$mindosesizeavail,
                          (int(r4c[10]))*$mindosesizeavail,
                          (int(r4c[10]))*$mindosesizeavail)
                      else " "
      5    If (r4c[10] > 0 and $nrdosespertimeunit >= 3) then
                      choose( $nrdosespertimeunit,
                          " ",
                          0,
                          0,
                          (int(r4c[10]) + choose (r4c[11], 0, 1, 1, 0, 0, 0))*$mindosesizeavail,
                          (int(r4c[10]) + choose (r4c[11], 0, 0, 0, 1, 0, 0))*$mindosesizeavail,
                          (int(r4c[10]) + choose (r4c[11], 0, 0, 0, 1, 1, 0))*$mindosesizeavail,
                          (int(r4c[10]) + choose (r4c[11], 0, 0, 0, 1, 1, 1))*$mindosesizeavail)
                      else " "
      6    If (r4c[10] > 0 and $nrdosespertimeunit >= 4) then
                      choose( $nrdosespertimeunit,
                          " ",
                          0,
                          0,
                          0,
                          (int(r4c[10]) + choose (r4c[11], 0, 1, 1, 1, 0, 0))*$mindosesizeavail,
                          (int(r4c[10]) + choose (r4c[11], 0, 0, 0, 0, 1, 0))*$mindosesizeavail,
                          (int(r4c[10]) + choose (r4c[11], 0, 0, 0, 0, 0, 1))*$mindosesizeavail)
                      else " "
      7    If (r4c[10] > 0 and $nrdosespertimeunit >= 5) then
                      choose( $nrdosespertimeunit,
                          " ",
                          0,
                          0,
                          0,
                          0,
                          (int(r4c[10]) + choose (r4c[11], 0, 1, 1, 1, 1, 0))*$mindosesizeavail,
```

FORMULAS FOR WORKSHEET Schedule

| ROW | COL | FORMULA |
|---|---|---|

```
                    (int(r4c[10]) + choose (r4c[11], 0, 0, 0, 0, 1, 1))*$mindosesizeavail)
            else " "
     8    if (r4c[10] > 0 and $nrdosespertimeunit >= 6) then
              choose( $nrdosespertimeunit,
                     " ",
                     0,
                     0,
                     0,
                     0,
                     0,
                     (int(r4c[10]) + choose (r4c[11], 0, 1, 1, 1, 1, 1))*$mindosesizeavail)
            else " "
     9    if (r4c1/$mindosesizeavail> 0) then (r4c1/$mindosesizeavail) else " "
    10    if (r4c9/$nrdosespertimeunit > 0) then
              (r4c9/$nrdosespertimeunit) else " "
    11    if (r4c10 > 0) then
              r4c9 - ( int(r4c10) * $nrdosespertimeunit)
            else " "
5    1    tapercal.r3c4
     2    if (r5c[10] > 0) then
              (   if $timespanforeachdose == "MINUTE" then addminutes($dateforfirstdose,row-4)
                  else if $timespanforeachdose == "HOUR" then addhours($dateforfirstdose,row-4)
                  else if $timespanforeachdose == "DAY" then adddays($dateforfirstdose,row-4)
                  else if $timespanforeachdose == "WEEK" then adddays($dateforfirstdose,7*(row-4))
                  else if $timespanforeachdose == "MONTH" then addmonths($dateforfirstdose,row-4)
                  else " " )
            else " "
     3    if (r5c[10] > 0) then
              choose( $nrdosespertimeunit,
                     " ",
                     (int(r5c[10]))*$mindosesizeavail,
                     (int(r5c[10]))*$mindosesizeavail,
                     (int(r5c[10]) + choose (r5c[11], 0, 0, 1, 0, 0, 0))*$mindosesizeavail,
                     (int(r5c[10]) + choose (r5c[11], 0, 0, 1, 1, 0, 0))*$mindosesizeavail,
                     (int(r5c[10]) + choose (r5c[11], 0, 0, 1, 1, 1, 0))*$mindosesizeavail,
                     (int(r5c[10]) + choose (r5c[11], 0, 0, 1, 1, 1, 1))*$mindosesizeavail)
            else " "
     4    if (r5c[10] > 0 and $nrdosespertimeunit >= 2) then
              choose( $nrdosespertimeunit,
                     " ",
                     0,
                     (int(r5c[10]) + choose (r5c[11], 0, 1, 0, 0, 0, 0))*$mindosesizeavail,
                     (int(r5c[10]))*$mindosesizeavail,
                     (int(r5c[10]))*$mindosesizeavail,
                     (int(r5c[10]))*$mindosesizeavail,
                     (int(r5c[10]))*$mindosesizeavail)
            else " "
     5    if (r5c[10] > 0 and $nrdosespertimeunit >= 3) then
              choose( $nrdosespertimeunit,
                     " ",
                     0,
                     0,
                     (int(r5c[10]) + choose (r5c[11], 0, 1, 1, 0, 0, 0))*$mindosesizeavail,
                     (int(r5c[10]) + choose (r5c[11], 0, 0, 0, 1, 0, 0))*$mindosesizeavail,
                     (int(r5c[10]) + choose (r5c[11], 0, 0, 0, 1, 1, 0))*$mindosesizeavail,
                     (int(r5c[10]) + choose (r5c[11], 0, 0, 0, 1, 1, 1))*$mindosesizeavail)
            else " "
     6    if (r5c[10] > 0 and $nrdosespertimeunit >= 4) then
              choose( $nrdosespertimeunit,
                     " ",
                     0,
                     0,
                     0,
                     (int(r5c[10]) + choose (r5c[11], 0, 1, 1, 1, 0, 0))*$mindosesizeavail,
                     (int(r5c[10]) + choose (r5c[11], 0, 0, 0, 0, 1, 0))*$mindosesizeavail,
                     (int(r5c[10]) + choose (r5c[11], 0, 0, 0, 0, 0, 1))*$mindosesizeavail)
            else " "
     7    if (r5c[10] > 0 and $nrdosespertimeunit >= 5) then
              choose( $nrdosespertimeunit,
```

FORMULAS FOR WORKSHEET Schedule

| ROW | COL | FORMULA |
|---|---|---|

```
                    " ",
                    0,
                    0,
                    0,
                    0,
                    (int(r5c[10]) + choose (r5c[11], 0, 1, 1, 1, 1, 0))*$mindosesizeavail,
                    (int(r5c[10]) + choose (r5c[11], 0, 0, 0, 0, 1, 1))*$mindosesizeavail)
            else " "
    8   If (r5c[10] > 0 and $nrdosespertimeunit >= 6) then
            choose( $nrdosespertimeunit,
                    " ",
                    0,
                    0,
                    0,
                    0,
                    0,
                    (int(r5c[10]) + choose (r5c[11], 0, 1, 1, 1, 1, 1))*$mindosesizeavail)
            else " "
    9   If (r5c1/$mindosesizeavail> 0) then (r5c1/$mindosesizeavail) else " "
    10  If (r5c9/$nrdosespertimeunit > 0) then
            (r5c9/$nrdosespertimeunit) else " "
    11  If (r5c10 > 0) then
            r5c9 - ( int(r5c10) * $nrdosespertimeunit)
            else " "
6   1   tapercal.r4c4
    2   If (r6c[10] > 0) then
            (
            if $timespanforeachdose == "MINUTE" then addminutes($dateforfirstdose,row-4)
            else if $timespanforeachdose == "HOUR" then addhours($dateforfirstdose,row-4)
            else if $timespanforeachdose == "DAY" then adddays($dateforfirstdose,row-4)
            else if $timespanforeachdose == "WEEK" then adddays($dateforfirstdose,7*(row-4))
            else if $timespanforeachdose == "MONTH" then addmonths($dateforfirstdose,row-4)
            else " " )
            else " "
    3   If (r6c[10] > 0) then
            choose( $nrdosespertimeunit,
                    " ",
                    (int(r6c[10]))*$mindosesizeavail,
                    (int(r6c[10]))*$mindosesizeavail,
                    (int(r6c[10]) + choose (r6c[11], 0, 0, 1, 0, 0, 0))*$mindosesizeavail,
                    (int(r6c[10]) + choose (r6c[11], 0, 0, 1, 1, 0, 0))*$mindosesizeavail,
                    (int(r6c[10]) + choose (r6c[11], 0, 0, 1, 1, 1, 0))*$mindosesizeavail,
                    (int(r6c[10]) + choose (r6c[11], 0, 0, 1, 1, 1, 1))*$mindosesizeavail)
            else " "
    4   If (r6c[10] > 0 and $nrdosespertimeunit >= 2) then
            choose( $nrdosespertimeunit,
                    " ",
                    0,
                    (int(r6c[10]) + choose (r6c[11], 0, 1, 0, 0, 0, 0))*$mindosesizeavail,
                    (int(r6c[10]))*$mindosesizeavail,
                    (int(r6c[10]))*$mindosesizeavail,
                    (int(r6c[10]))*$mindosesizeavail,
                    (int(r6c[10]))*$mindosesizeavail)
            else " "
    5   If (r6c[10] > 0 and $nrdosespertimeunit >= 3) then
            choose( $nrdosespertimeunit,
                    " ",
                    0,
                    0,
                    (int(r6c[10]) + choose (r6c[11], 0, 1, 1, 0, 0, 0))*$mindosesizeavail,
                    (int(r6c[10]) + choose (r6c[11], 0, 0, 0, 1, 0, 0))*$mindosesizeavail,
                    (int(r6c[10]) + choose (r6c[11], 0, 0, 0, 1, 1, 0))*$mindosesizeavail,
                    (int(r6c[10]) + choose (r6c[11], 0, 0, 0, 1, 1, 1))*$mindosesizeavail)
            else " "
    6   If (r6c[10] > 0 and $nrdosespertimeunit >= 4) then
            choose( $nrdosespertimeunit,
                    " ",
                    0,
                    0,
                    0,
```

FORMULAS FOR WORKSHEET SchedDis

| ROW | COL | FORMULA |
|---|---|---|

```
                        (int(r6c[10]) + choose (r6c[11], 0, 1, 1, 1, 0, 0))*$mindosesizeavail,
                        (int(r6c[10]) + choose (r6c[11], 0, 0, 0, 0, 1, 0))*$mindosesizeavail,
                        (int(r6c[10]) + choose (r6c[11], 0, 0, 0, 0, 0, 1))*$mindosesizeavail)
                   else " "
      7   If (r6c[10] > 0 and $nrdosespertimeunit >= 5) then
                   choose( $nrdosespertimeunit,
                        " ",
                        0,
                        0,
                        0,
                        0,
                        (int(r6c[10]) + choose (r6c[11], 0, 1, 1, 1, 1, 0))*$mindosesizeavail,
                        (int(r6c[10]) + choose (r6c[11], 0, 0, 0, 0, 1, 1))*$mindosesizeavail)
                   else " "
      8   If (r6c[10] > 0 and $nrdosespertimeunit >= 6) then
                   choose( $nrdosespertimeunit,
                        " ",
                        0,
                        0,
                        0,
                        0,
                        0,
                        (int(r6c[10]) + choose (r6c[11], 0, 1, 1, 1, 1, 1))*$mindosesizeavail)
                   else " "
      9   If (r6c1/$mindosesizeavail> 0) then (r6c1/$mindosesizeavail) else " "
     10   If (r6c9/$nrdosespertimeunit > 0) then
                   (r6c9/$nrdosespertimeunit) else " "
     11   If (r6c10 > 0) then
                   r6c9 - ( int(r6c10) * $nrdosespertimeunit)
                   else " "
  7   1   tapercal.r5c4
      2   If (r7c[10] > 0) then
                 (  If $timespanforeachdose == "MINUTE" then addminutes($dateforfirstdose,row-4)
                    else if $timespanforeachdose == "HOUR" then addhours($dateforfirstdose,row-4)
                    else if $timespanforeachdose == "DAY" then adddays($dateforfirstdose,row-4)
                    else if $timespanforeachdose == "WEEK" then adddays($dateforfirstdose,7*(row-4))
                    else if $timespanforeachdose == "MONTH" then addmonths($dateforfirstdose,row-4)
                    else " " )
                 else " "
      3   If (r7c[10] > 0) then
                   choose( $nrdosespertimeunit,
                        " ",
                        (int(r7c[10]))*$mindosesizeavail,
                        (int(r7c[10]))*$mindosesizeavail,
                        (int(r7c[10]) + choose (r7c[11], 0, 0, 1, 0, 0, 0))*$mindosesizeavail,
                        (int(r7c[10]) + choose (r7c[11], 0, 0, 1, 1, 0, 0))*$mindosesizeavail,
                        (int(r7c[10]) + choose (r7c[11], 0, 0, 1, 1, 1, 0))*$mindosesizeavail,
                        (int(r7c[10]) + choose (r7c[11], 0, 0, 1, 1, 1, 1))*$mindosesizeavail)
                   else " "
      4   If (r7c[10] > 0 and $nrdosespertimeunit >= 2) then
                   choose( $nrdosespertimeunit,
                        " ",
                        0,
                        (int(r7c[10]) + choose (r7c[11], 0, 1, 0, 0, 0, 0))*$mindosesizeavail,
                        (int(r7c[10]))*$mindosesizeavail,
                        (int(r7c[10]))*$mindosesizeavail,
                        (int(r7c[10]))*$mindosesizeavail,
                        (int(r7c[10]))*$mindosesizeavail)
                   else " "
      5   If (r7c[10] > 0 and $nrdosespertimeunit >= 3) then
                   choose( $nrdosespertimeunit,
                        " ",
                        0,
                        0,
                        (int(r7c[10]) + choose (r7c[11], 0, 1, 1, 0, 0, 0))*$mindosesizeavail,
                        (int(r7c[10]) + choose (r7c[11], 0, 0, 0, 1, 0, 0))*$mindosesizeavail,
                        (int(r7c[10]) + choose (r7c[11], 0, 0, 0, 1, 1, 0))*$mindosesizeavail,
                        (int(r7c[10]) + choose (r7c[11], 0, 0, 0, 1, 1, 1))*$mindosesizeavail)
                   else " "
```

FORMULAS FOR WORKSHEET $schedis

| ROW | COL | FORMULA |
|---|---|---|
| | 6 | if (r7c[10] > 0 and $nrdosespertimeunit >= 4) then<br>    choose( $nrdosespertimeunit,<br>        " ",<br>        0,<br>        0,<br>        0,<br>        (int(r7c[10]) + choose (r7c[11], 0, 1, 1, 1, 0, 0))*$mindosesizeavail,<br>        (int(r7c[10]) + choose (r7c[11], 0, 0, 0, 0, 1, 0))*$mindosesizeavail,<br>        (int(r7c[10]) + choose (r7c[11], 0, 0, 0, 0, 0, 1))*$mindosesizeavail)<br>    else " " |
| | 7 | if (r7c[10] > 0 and $nrdosespertimeunit >= 5) then<br>    choose( $nrdosespertimeunit,<br>        " ",<br>        0,<br>        0,<br>        0,<br>        0,<br>        (int(r7c[10]) + choose (r7c[11], 0, 1, 1, 1, 1, 0))*$mindosesizeavail,<br>        (int(r7c[10]) + choose (r7c[11], 0, 0, 0, 0, 1, 1))*$mindosesizeavail)<br>    else " " |
| | 8 | if (r7c[10] > 0 and $nrdosespertimeunit >= 6) then<br>    choose( $nrdosespertimeunit,<br>        " ",<br>        0,<br>        0,<br>        0,<br>        0,<br>        0,<br>        (int(r7c[10]) + choose (r7c[11], 0, 1, 1, 1, 1, 1))*$mindosesizeavail)<br>    else " " |
| | 9 | if (r7c1/$mindosesizeavail> 0) then (r7c1/$mindosesizeavail) else " " |
| | 10 | if (r7c9/$nrdosespertimeunit > 0) then<br>    (r7c9/$nrdosespertimeunit) else " " |
| | 11 | if (r7c10 > 0) then<br>    r7c9 - ( int(r7c10) * $nrdosespertimeunit)<br>    else " " |
| 8 | 1 | tapercal.r6c4 |
| | 2 | if (r8c[10] > 0) then<br>    ( if $timespanforeachdose == "MINUTE" then addminutes($dateforfirstdose,row-4)<br>      else if $timespanforeachdose == "HOUR" then addhours($dateforfirstdose,row-4)<br>      else if $timespanforeachdose == "DAY" then adddays($dateforfirstdose,row-4)<br>      else if $timespanforeachdose == "WEEK" then adddays($dateforfirstdose,7*(row-4))<br>      else if $timespanforeachdose == "MONTH" then addmonths($dateforfirstdose,row-4)<br>      else " " )<br>    else " " |
| | 3 | if (r8c[10] > 0) then<br>    choose( $nrdosespertimeunit,<br>        " ",<br>        (int(r8c[10]))*$mindosesizeavail,<br>        (int(r8c[10]))*$mindosesizeavail,<br>        (int(r8c[10]) + choose (r8c[11], 0, 0, 1, 0, 0, 0))*$mindosesizeavail,<br>        (int(r8c[10]) + choose (r8c[11], 0, 0, 1, 1, 0, 0))*$mindosesizeavail,<br>        (int(r8c[10]) + choose (r8c[11], 0, 0, 1, 1, 1, 0))*$mindosesizeavail,<br>        (int(r8c[10]) + choose (r8c[11], 0, 0, 1, 1, 1, 1))*$mindosesizeavail)<br>    else " " |
| | 4 | if (r8c[10] > 0 and $nrdosespertimeunit >= 2) then<br>    choose( $nrdosespertimeunit,<br>        " ",<br>        0,<br>        (int(r8c[10]) + choose (r8c[11], 0, 1, 0, 0, 0, 0))*$mindosesizeavail,<br>        (int(r8c[10]))*$mindosesizeavail,<br>        (int(r8c[10]))*$mindosesizeavail,<br>        (int(r8c[10]))*$mindosesizeavail,<br>        (int(r8c[10]))*$mindosesizeavail)<br>    else " " |
| | 5 | if (r8c[10] > 0 and $nrdosespertimeunit >= 3) then<br>    choose( $nrdosespertimeunit,<br>        " ",<br>        0, |

FORMULAS FOR WORKSHEET ScheoDle

| ROW | COL | FORMULA |
|---|---|---|

```
                        0,
                        (int(r8c[10]) + choose (r8c[11], 0, 1, 1, 0, 0, 0))*$mindosesizeavail,
                        (int(r8c[10]) + choose (r8c[11], 0, 0, 0, 1, 0, 0))*$mindosesizeavail,
                        (int(r8c[10]) + choose (r8c[11], 0, 0, 0, 1, 1, 0))*$mindosesizeavail,
                        (int(r8c[10]) + choose (r8c[11], 0, 0, 0, 1, 1, 1))*$mindosesizeavail)
                else " "
        6   if (r8c[10] > 0 and $nrdosespertimeunit >= 4) then
                choose( $nrdosespertimeunit,
                        " ",
                        0,
                        0,
                        0,
                        (int(r8c[10]) + choose (r8c[11], 0, 1, 1, 1, 0, 0))*$mindosesizeavail,
                        (int(r8c[10]) + choose (r8c[11], 0, 0, 0, 0, 1, 0))*$mindosesizeavail,
                        (int(r8c[10]) + choose (r8c[11], 0, 0, 0, 0, 0, 1))*$mindosesizeavail)
                else " "
        7   if (r8c[10] > 0 and $nrdosespertimeunit >= 5) then
                choose( $nrdosespertimeunit,
                        " ",
                        0,
                        0,
                        0,
                        0,
                        (int(r8c[10]) + choose (r8c[11], 0, 1, 1, 1, 1, 0))*$mindosesizeavail,
                        (int(r8c[10]) + choose (r8c[11], 0, 0, 0, 0, 1, 1))*$mindosesizeavail)
                else " "
        8   if (r8c[10] > 0 and $nrdosespertimeunit >= 6) then
                choose( $nrdosespertimeunit,
                        " ",
                        0,
                        0,
                        0,
                        0,
                        0,
                        (int(r8c[10]) + choose (r8c[11], 0, 1, 1, 1, 1, 1))*$mindosesizeavail)
                else " "
        9   if (r8c1/$mindosesizeavail> 0) then (r8c1/$mindosesizeavail) else " "
       10   if (r8c9/$nrdosespertimeunit > 0) then
                (r8c9/$nrdosespertimeunit) else " "
       11   if (r8c10 > 0) then
                r8c9 - ( int(r8c10) * $nrdosespertimeunit)
                else " "
 9      1   taporcal.r7c4
        2   if (r9c[10] > 0) then
                (   if $timespanforeachdose == "MINUTE" then addminutes($dateforfirstdose,row-4)
                    else if $timespanforeachdose == "HOUR" then addhours($dateforfirstdose,row-4)
                    else if $timespanforeachdose == "DAY" then adddays($dateforfirstdose,row-4)
                    else if $timespanforeachdose == "WEEK" then adddays($dateforfirstdose,7*(row-4))
                    else if $timespanforeachdose == "MONTH" then addmonths($dateforfirstdose,row-4)
                    else " " )
                else " "
        3   if (r9c[10] > 0) then
                choose( $nrdosespertimeunit,
                        " ",
                        (int(r9c[10]))*$mindosesizeavail,
                        (int(r9c[10]))*$mindosesizeavail,
                        (int(r9c[10]) + choose (r9c[11], 0, 0, 1, 0, 0, 0))*$mindosesizeavail,
                        (int(r9c[10]) + choose (r9c[11], 0, 0, 1, 1, 0, 0))*$mindosesizeavail,
                        (int(r9c[10]) + choose (r9c[11], 0, 0, 1, 1, 1, 0))*$mindosesizeavail,
                        (int(r9c[10]) + choose (r9c[11], 0, 0, 1, 1, 1, 1))*$mindosesizeavail)
                else " "
        4   if (r9c[10] > 0 and $nrdosespertimeunit >= 2) then
                choose( $nrdosespertimeunit,
                        " ",
                        0,
                        (int(r9c[10]) + choose (r9c[11], 0, 1, 0, 0, 0, 0))*$mindosesizeavail,
                        (int(r9c[10]))*$mindosesizeavail,
                        (int(r9c[10]))*$mindosesizeavail,
                        (int(r9c[10]))*$mindosesizeavail,
```

FORMULAS FOR WORKSHEET SchedDis

| ROW | COL | FORMULA |
|---|---|---|
| | | |

```
                                   (int(r9c[10]))*$mindosesizeavail)
                              else " "
       5    If (r9c[10] > 0 and $nrdosespertimeunit >= 3) then
                 choose( $nrdosespertimeunit,
                         " ",
                         0,
                         0,
                         (int(r9c[10]) + choose (r9c[11], 0, 1, 1, 0, 0, 0))*$mindosesizeavail,
                         (int(r9c[10]) + choose (r9c[11], 0, 0, 0, 1, 0, 0))*$mindosesizeavail,
                         (int(r9c[10]) + choose (r9c[11], 0, 0, 0, 1, 1, 0))*$mindosesizeavail,
                         (int(r9c[10]) + choose (r9c[11], 0, 0, 0, 1, 1, 1))*$mindosesizeavail)
                              else " "
       6    If (r9c[10] > 0 and $nrdosespertimeunit >= 4) then
                 choose( $nrdosespertimeunit,
                         " ",
                         0,
                         0,
                         0,
                         (int(r9c[10]) + choose (r9c[11], 0, 1, 1, 1, 0, 0))*$mindosesizeavail,
                         (int(r9c[10]) + choose (r9c[11], 0, 0, 0, 0, 1, 0))*$mindosesizeavail,
                         (int(r9c[10]) + choose (r9c[11], 0, 0, 0, 0, 0, 1))*$mindosesizeavail)
                              else " "
       7    If (r9c[10] > 0 and $nrdosespertimeunit >= 5) then
                 choose( $nrdosespertimeunit,
                         " ",
                         0,
                         0,
                         0,
                         0,
                         (int(r9c[10]) + choose (r9c[11], 0, 1, 1, 1, 1, 0))*$mindosesizeavail,
                         (int(r9c[10]) + choose (r9c[11], 0, 0, 0, 0, 1, 1))*$mindosesizeavail)
                              else " "
       8    If (r9c[10] > 0 and $nrdosespertimeunit >= 6) then
                 choose( $nrdosespertimeunit,
                         " ",
                         0,
                         0,
                         0,
                         0,
                         0,
                         (int(r9c[10]) + choose (r9c[11], 0, 1, 1, 1, 1, 1))*$mindosesizeavail)
                              else " "
       9    If (r9c1/$mindosesizeavail> 0) then (r9c1/$mindosesizeavail) else " "
      10    If (r9c9/$nrdosespertimeunit > 0) then
                 (r9c9/$nrdosespertimeunit) else " "
      11    If (r9c10 > 0) then
                 r9c9 - ( int(r9c10) * $nrdosespertimeunit)
                              else " "
10     1    tapercal.r8c4
       2    If (r10c[10] > 0) then
                 ( if $timespanforeachdose == "MINUTE" then addminutes($dateforfirstdose,row-4)
                   else if $timespanforeachdose == "HOUR" then addhours($dateforfirstdose,row-4)
                   else if $timespanforeachdose == "DAY" then adddays($dateforfirstdose,row-4)
                   else if $timespanforeachdose == "WEEK" then adddays($dateforfirstdose,7*(row-4))
                   else if $timespanforeachdose == "MONTH" then addmonths($dateforfirstdose,row-4)
                   else " " )
                              else " "
       3    If (r10c[10] > 0) then
                 choose( $nrdosespertimeunit,
                         " ",
                         (int(r10c[10]))*$mindosesizeavail,
                         (int(r10c[10]))*$mindosesizeavail,
                         (int(r10c[10]) + choose (r10c[11], 0, 0, 1, 0, 0, 0))*$mindosesizeavail,
                         (int(r10c[10]) + choose (r10c[11], 0, 0, 1, 1, 0, 0))*$mindosesizeavail,
                         (int(r10c[10]) + choose (r10c[11], 0, 0, 1, 1, 1, 0))*$mindosesizeavail,
                         (int(r10c[10]) + choose (r10c[11], 0, 0, 1, 1, 1, 1))*$mindosesizeavail)
                              else " "
       4    If (r10c[10] > 0 and $nrdosespertimeunit >= 2) then
                 choose( $nrdosespertimeunit,
```

FORMULAS FOR WORKSHEET SchedDis

| ROW | COL | FORMULA |
|---|---|---|
| | | `" ",`<br>`0,`<br>`(int(r10c[10]) + choose (r10c[11], 0, 1, 0, 0, 0, 0))*$mindosesizeavail,`<br>`(int(r10c[10]))*$mindosesizeavail,`<br>`(int(r10c[10]))*$mindosesizeavail,`<br>`(int(r10c[10]))*$mindosesizeavail,`<br>`(int(r10c[10]))*$mindosesizeavail)`<br>`else " "` |
| | 5 | `If (r10c[10] > 0 and $nrdosespertimeunit >= 3) then`<br>`  choose( $nrdosespertimeunit,`<br>`    " ",`<br>`    0,`<br>`    0,`<br>`    (int(r10c[10]) + choose (r10c[11], 0, 1, 1, 0, 0, 0))*$mindosesizeavail,`<br>`    (int(r10c[10]) + choose (r10c[11], 0, 0, 0, 1, 0, 0))*$mindosesizeavail,`<br>`    (int(r10c[10]) + choose (r10c[11], 0, 0, 0, 1, 1, 0))*$mindosesizeavail,`<br>`    (int(r10c[10]) + choose (r10c[11], 0, 0, 0, 1, 1, 1))*$mindosesizeavail)`<br>`else " "` |
| | 6 | `If (r10c[10] > 0 and $nrdosespertimeunit >= 4) then`<br>`  choose( $nrdosespertimeunit,`<br>`    " ",`<br>`    0,`<br>`    0,`<br>`    0,`<br>`    (int(r10c[10]) + choose (r10c[11], 0, 1, 1, 1, 0, 0))*$mindosesizeavail,`<br>`    (int(r10c[10]) + choose (r10c[11], 0, 0, 0, 0, 1, 0))*$mindosesizeavail,`<br>`    (int(r10c[10]) + choose (r10c[11], 0, 0, 0, 0, 0, 1))*$mindosesizeavail)`<br>`else " "` |
| | 7 | `If (r10c[10] > 0 and $nrdosespertimeunit >= 5) then`<br>`  choose( $nrdosespertimeunit,`<br>`    " ",`<br>`    0,`<br>`    0,`<br>`    0,`<br>`    0,`<br>`    (int(r10c[10]) + choose (r10c[11], 0, 1, 1, 1, 1, 0))*$mindosesizeavail,`<br>`    (int(r10c[10]) + choose (r10c[11], 0, 0, 0, 0, 1, 1))*$mindosesizeavail)`<br>`else " "` |
| | 8 | `If (r10c[10] > 0 and $nrdosespertimeunit >= 6) then`<br>`  choose( $nrdosespertimeunit,`<br>`    " ",`<br>`    0,`<br>`    0,`<br>`    0,`<br>`    0,`<br>`    0,`<br>`    (int(r10c[10]) + choose (r10c[11], 0, 1, 1, 1, 1, 1))*$mindosesizeavail)`<br>`else " "` |
| | 9 | `If (r10c1/$mindosesizeavail> 0) then (r10c1/$mindosesizeavail) else " "` |
| | 10 | `If (r10c9/$nrdosespertimeunit > 0) then`<br>`  (r10c9/$nrdosespertimeunit) else " "` |
| | 11 | `If (r10c10 > 0) then`<br>`  r10c9 - ( int(r10c10) * $nrdosespertimeunit)`<br>`else " "` |
| 11 | 1 | `tapercal.r9c4` |
| | 2 | `If (r11c[10] > 0) then`<br>`  (   if $timespanforeachdose == "MINUTE" then addminutes($dateforfirstdose,row-4)`<br>`    else if $timespanforeachdose == "HOUR" then addhours($dateforfirstdose,row-4)`<br>`    else if $timespanforeachdose == "DAY" then adddays($dateforfirstdose,row-4)`<br>`    else if $timespanforeachdose == "WEEK" then adddays($dateforfirstdose,7*(row-4))`<br>`    else if $timespanforeachdose == "MONTH" then addmonths($dateforfirstdose,row-4)`<br>`    else " " )`<br>`else " "` |
| | 3 | `If (r11c[10] > 0) then`<br>`  choose( $nrdosespertimeunit,`<br>`    " ",`<br>`    (int(r11c[10]))*$mindosesizeavail,`<br>`    (int(r11c[10]))*$mindosesizeavail,`<br>`    (int(r11c[10]) + choose (r11c[11], 0, 0, 1, 0, 0, 0))*$mindosesizeavail,` |

FORMULAS FOR WORKSHEET $schedDis

| ROW | COL | FORMULA |
|---|---|---|

```
                    (int(r11c[10]) + choose (r11c[11], 0, 0, 1, 1, 0, 0))*$mindosesizeavail,
                    (int(r11c[10]) + choose (r11c[11], 0, 0, 1, 1, 1, 0))*$mindosesizeavail,
                    (int(r11c[10]) + choose (r11c[11], 0, 0, 1, 1, 1, 1))*$mindosesizeavail)
            else " "
    4   If (r11c[10] > 0 and $nrdosespertimeunit >= 2) then
            choose( $nrdosespertimeunit,
                    " ",
                    0,
                    (int(r11c[10]) + choose (r11c[11], 0, 1, 0, 0, 0, 0))*$mindosesizeavail,
                    (int(r11c[10]))*$mindosesizeavail,
                    (int(r11c[10]))*$mindosesizeavail,
                    (int(r11c[10]))*$mindosesizeavail,
                    (int(r11c[10]))*$mindosesizeavail)
            else " "
    5   If (r11c[10] > 0 and $nrdosespertimeunit >= 3) then
            choose( $nrdosespertimeunit,
                    " ",
                    0,
                    0,
                    (int(r11c[10]) + choose (r11c[11], 0, 1, 1, 0, 0, 0))*$mindosesizeavail,
                    (int(r11c[10]) + choose (r11c[11], 0, 0, 0, 1, 0, 0))*$mindosesizeavail,
                    (int(r11c[10]) + choose (r11c[11], 0, 0, 0, 1, 1, 0))*$mindosesizeavail,
                    (int(r11c[10]) + choose (r11c[11], 0, 0, 0, 1, 1, 1))*$mindosesizeavail)
            else " "
    6   If (r11c[10] > 0 and $nrdosespertimeunit >= 4) then
            choose( $nrdosespertimeunit,
                    " ",
                    0,
                    0,
                    0,
                    (int(r11c[10]) + choose (r11c[11], 0, 1, 1, 1, 0, 0))*$mindosesizeavail,
                    (int(r11c[10]) + choose (r11c[11], 0, 0, 0, 0, 1, 0))*$mindosesizeavail,
                    (int(r11c[10]) + choose (r11c[11], 0, 0, 0, 0, 0, 1))*$mindosesizeavail)
            else " "
    7   If (r11c[10] > 0 and $nrdosespertimeunit >= 5) then
            choose( $nrdosespertimeunit,
                    " ",
                    0,
                    0,
                    0,
                    0,
                    (int(r11c[10]) + choose (r11c[11], 0, 1, 1, 1, 1, 0))*$mindosesizeavail,
                    (int(r11c[10]) + choose (r11c[11], 0, 0, 0, 0, 1, 1))*$mindosesizeavail)
            else " "
    8   If (r11c[10] > 0 and $nrdosespertimeunit >= 6) then
            choose( $nrdosespertimeunit,
                    " ",
                    0,
                    0,
                    0,
                    0,
                    0,
                    (int(r11c[10]) + choose (r11c[11], 0, 1, 1, 1, 1, 1))*$mindosesizeavail)
            else " "
    9   If (r11c1/$mindosesizeavail> 0) then (r11c1/$mindosesizeavail) else " "
    10  If (r11c9/$nrdosespertimeunit > 0) then
            (r11c9/$nrdosespertimeunit) else " "
    11  If (r11c10 > 0) then
            r11c9 - ( int(r11c10) * $nrdosespertimeunit)
            else " "
12  1   tapercal.r10c4
    2   If (r12c[10] > 0) then
            ( If $timespanforeachdose == "MINUTE" then addminutes($dateforfirstdose,row-4)
              else If $timespanforeachdose == "HOUR" then addhours($dateforfirstdose,row-4)
              else if $timespanforeachdose == "DAY" then adddays($dateforfirstdose,row-4)
              else if $timespanforeachdose == "WEEK" then adddays($dateforfirstdose,7*(row-4))
              else if $timespanforeachdose == "MONTH" then addmonths($dateforfirstdose,row-4)
              else " " )
            else " "
```

FORMULAS FOR WORKSHEET SchedDis

| ROW | COL | FORMULA |
|---|---|---|
| | 3 | ```
if (r12c[10] > 0) then
    choose( $nrdosespertimeunit,
        " ",
        (int(r12c[10]))*$mindosesizeavail,
        (int(r12c[10]))*$mindosesizeavail,
        (int(r12c[10]) + choose (r12c[11], 0, 0, 1, 0, 0, 0))*$mindosesizeavail,
        (int(r12c[10]) + choose (r12c[11], 0, 0, 1, 1, 0, 0))*$mindosesizeavail,
        (int(r12c[10]) + choose (r12c[11], 0, 0, 1, 1, 1, 0))*$mindosesizeavail,
        (int(r12c[10]) + choose (r12c[11], 0, 0, 1, 1, 1, 1))*$mindosesizeavail)
    else " "
``` |
| | 4 | ```
if (r12c[10] > 0 and $nrdosespertimeunit >= 2) then
    choose( $nrdosespertimeunit,
        " ",
        0,
        (int(r12c[10]) + choose (r12c[11], 0, 1, 0, 0, 0, 0))*$mindosesizeavail,
        (int(r12c[10]))*$mindosesizeavail,
        (int(r12c[10]))*$mindosesizeavail,
        (int(r12c[10]))*$mindosesizeavail,
        (int(r12c[10]))*$mindosesizeavail)
    else " "
``` |
| | 5 | ```
if (r12c[10] > 0 and $nrdosespertimeunit >= 3) then
    choose( $nrdosespertimeunit,
        " ",
        0,
        0,
        (int(r12c[10]) + choose (r12c[11], 0, 1, 1, 0, 0, 0))*$mindosesizeavail,
        (int(r12c[10]) + choose (r12c[11], 0, 0, 0, 1, 0, 0))*$mindosesizeavail,
        (int(r12c[10]) + choose (r12c[11], 0, 0, 0, 1, 1, 0))*$mindosesizeavail,
        (int(r12c[10]) + choose (r12c[11], 0, 0, 0, 1, 1, 1))*$mindosesizeavail)
    else " "
``` |
| | 6 | ```
if (r12c[10] > 0 and $nrdosespertimeunit >= 4) then
    choose( $nrdosespertimeunit,
        " ",
        0,
        0,
        0,
        (int(r12c[10]) + choose (r12c[11], 0, 1, 1, 1, 0, 0))*$mindosesizeavail,
        (int(r12c[10]) + choose (r12c[11], 0, 0, 0, 0, 1, 0))*$mindosesizeavail,
        (int(r12c[10]) + choose (r12c[11], 0, 0, 0, 0, 0, 1))*$mindosesizeavail)
    else " "
``` |
| | 7 | ```
if (r12c[10] > 0 and $nrdosespertimeunit >= 5) then
    choose( $nrdosespertimeunit,
        " ",
        0,
        0,
        0,
        0,
        (int(r12c[10]) + choose (r12c[11], 0, 1, 1, 1, 1, 0))*$mindosesizeavail,
        (int(r12c[10]) + choose (r12c[11], 0, 0, 0, 0, 1, 1))*$mindosesizeavail)
    else " "
``` |
| | 8 | ```
if (r12c[10] > 0 and $nrdosespertimeunit >= 6) then
    choose( $nrdosespertimeunit,
        " ",
        0,
        0,
        0,
        0,
        0,
        (int(r12c[10]) + choose (r12c[11], 0, 1, 1, 1, 1, 1))*$mindosesizeavail)
    else " "
``` |
| | 9 | if (r12c1/$mindosesizeavail> 0) then (r12c1/$mindosesizeavail) else " " |
| | 10 | if (r12c9/$nrdosespertimeunit > 0) then (r12c9/$nrdosespertimeunit) else " " |
| | 11 | ```
if (r12c10 > 0) then
    r12c9 - ( int(r12c10) * $nrdosespertimeunit)
    else " "
``` |

I claim:

1. A method of tapering a patient from a medicament, comprising:
   a. predetermining the initial dose of said medicament as a first parameter;
   b. predetermining at least one of the parameters selected from the group consisting of an intermediate dose of said medicament, the final dose of said medicament, the duration of said taper, and the percent decrement between said initial dose and said final dose as a second parameter;
   c. calculating a tapering schedule in accordance with the algorithm $$G(t)=Rnd[a,M]$$

wherein $G(t)$ is the amount of said medicament given at time t, Rnd is a rounding function which rounds a to the nearest multiple of M; a is $K_1 k_2'$, wherein $k_1$ is the initial dose of said medicament, $k_2$ is said second parameter, and t is time, and M is the minimum dosage size available;
   d. administering said medicament to said patient in a dosage amount in accordance with said calculated tapering schedule;
   e. observing the clinical response of said patient to said administration;
   f. modifying said dosage amount if said response indicates that said dosage amount is too high or too low, until the response of said patient to said modified dosage amount is stable;
   g. recalculating a tapering schedule in accordance with the algorithm in part (c) using as said first parameter said initial dose and as said second parameter said modified dosage amount; and,
   h. administering said medicament to said patient in a dosage amount in accordance with said recalculated tapering schedule.

* * * * *